(12) United States Patent
Mahr et al.

(10) Patent No.: US 10,272,114 B1
(45) Date of Patent: Apr. 30, 2019

(54) PEPTIDES AND SCAFFOLDS FOR USE IN IMMUNOTHERAPY AGAINST HEAD AND NECK SQUAMOUS CELL CARCINOMA AND OTHER CANCERS

(71) Applicant: Immatics Biotechnologies GmbH, Tuebingen (DE)

(72) Inventors: Andrea Mahr, Tuebingen (DE); Toni Weinschenk, Aichwald (DE); Anita Wiebe, Ruebgarten (DE); Colette Song, Ostfildern (DE); Oliver Schoor, Tuebingen (DE); Jens Fritsche, Dusslingen (DE); Harpreet Singh, Muenchen Schwabing (DE)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 0 days.

(21) Appl. No.: 16/235,147

(22) Filed: Dec. 28, 2018

Related U.S. Application Data

(63) Continuation of application No. 16/162,337, filed on Oct. 16, 2018, now Pat. No. 10,195,232, which is a continuation of application No. 15/686,679, filed on Aug. 25, 2017.

(60) Provisional application No. 62/379,864, filed on Aug. 26, 2016.

(30) Foreign Application Priority Data

Aug. 26, 2016 (DE) .................... 10 2016 115 974

(51) Int. Cl.
| | | |
|---|---|---|
| *A61K 35/17* | (2015.01) | |
| *C07K 14/74* | (2006.01) | |
| *C07K 16/30* | (2006.01) | |
| *A61K 39/00* | (2006.01) | |
| *C12N 5/0783* | (2010.01) | |
| *C07K 14/47* | (2006.01) | |
| *C07K 16/28* | (2006.01) | |
| *C07K 16/18* | (2006.01) | |
| *C12N 15/115* | (2010.01) | |

(52) U.S. Cl.
CPC .......... *A61K 35/17* (2013.01); *A61K 39/0011* (2013.01); *C07K 14/4748* (2013.01); *C07K 14/70539* (2013.01); *C07K 16/2833* (2013.01); *C07K 16/3053* (2013.01); *C12N 5/0636* (2013.01); *C07K 16/18* (2013.01); *C12N 15/115* (2013.01)

(58) Field of Classification Search
CPC ................................ A61K 35/17; A61K 38/00
See application file for complete search history.

(56) References Cited

FOREIGN PATENT DOCUMENTS

| WO | 2003/062391 A2 | 7/2003 |
|---|---|---|
| WO | 2011/113872 A1 | 9/2011 |
| WO | 2015/169945 A2 | 11/2015 |
| WO | 2015/193359 A2 | 12/2015 |

OTHER PUBLICATIONS

Varilla et al. (Expert Opin Biol Ther. Sep. 2013; 13 (9): 1241-56).
International Search Reporting for PCT/EP2017/071347 dated Jan. 17, 2018.
"Human structural and cytoskeleton-associated protein (SCAP) #20." Retrieved from EBI accession No. GSP: ADE15641. Jan. 29, 2004.
"Human keratin 6B protein, SEQ 4." XP002774546, retrieved from EBI accession No. GSP:BBP53541. Dec. 4, 2014.
"Human keratin, type I cytoskeletal 17 (Cytokeratin 17) SEQ:114." XP002774547, retrieved from EBI accession No. GSP:BAF31682. Dec. 20, 2012.
"Human cytokeratin 12 antigen." XP002774548, retrieved from EBI accession No. GSP:BBC42354. Apr. 10, 2014.
B. Perez-Ordonez. "Molecular biology of squamous cell carcinoma of the head and neck." Journal of Clinical Pathology. vol. 59(5): 445-453, Feb. 16, 2006. DOI: 10.1136/jcp.2003.007641.

*Primary Examiner* — Stephen L Rawlings
(74) *Attorney, Agent, or Firm* — McBee Moore Woodward & Vanik IP, LLC; Susan McBee

(57) ABSTRACT

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

17 Claims, 23 Drawing Sheets

Specification includes a Sequence Listing.

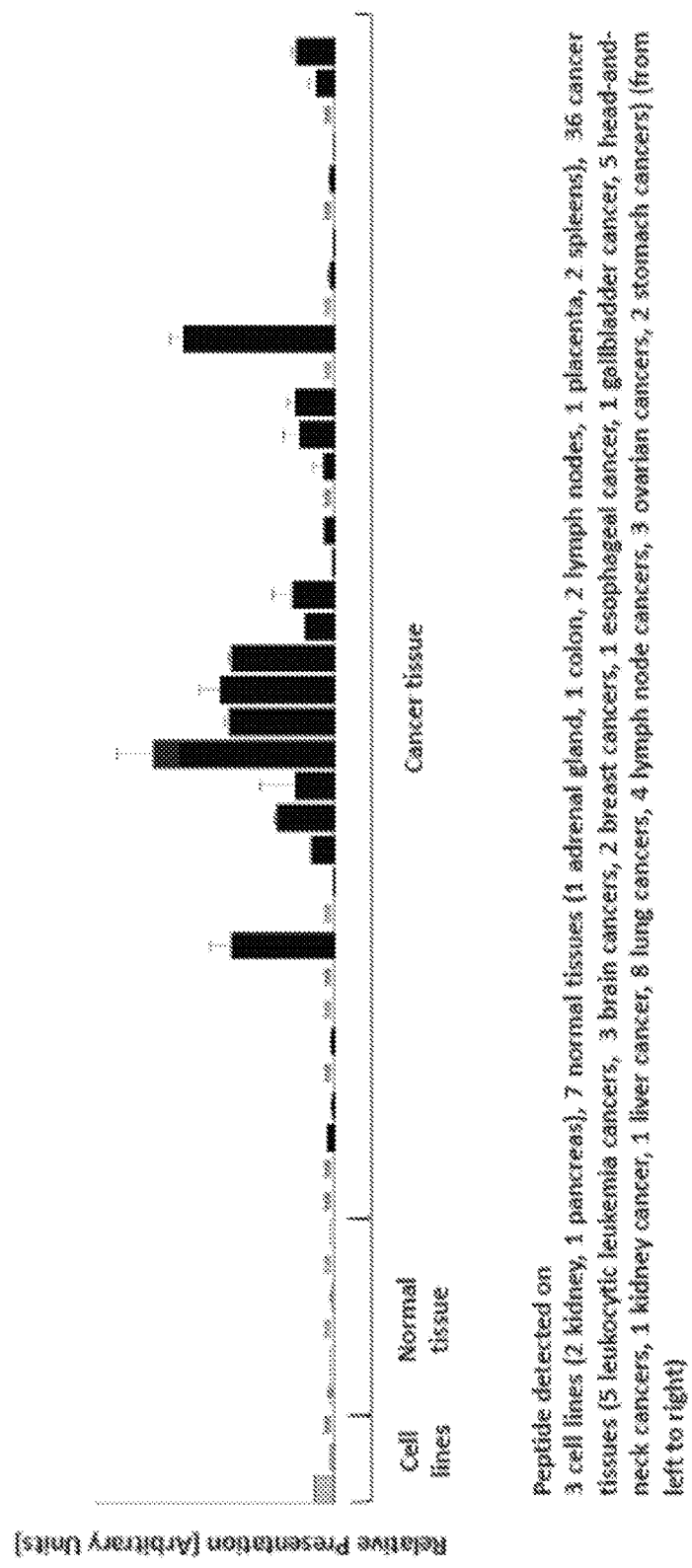

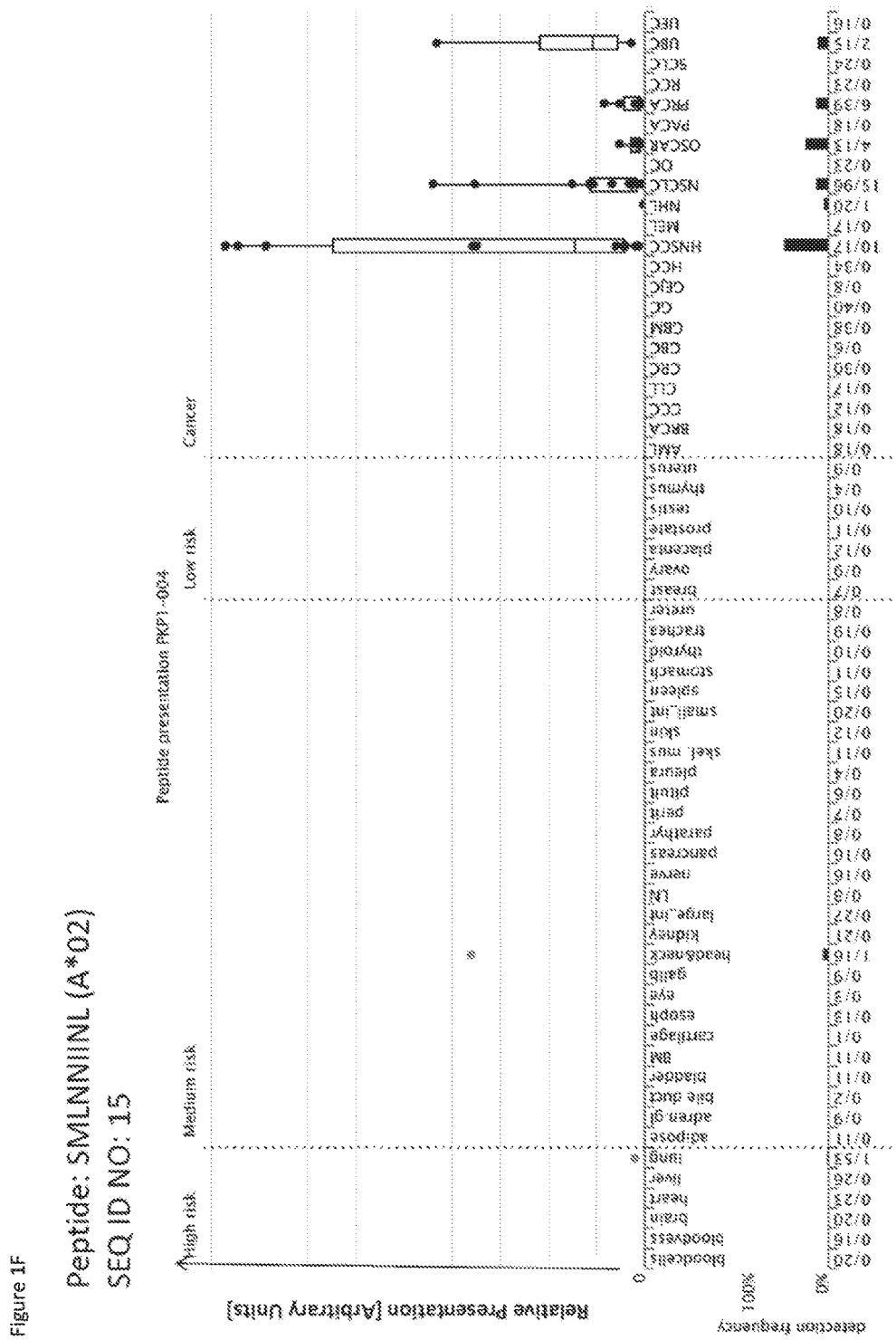

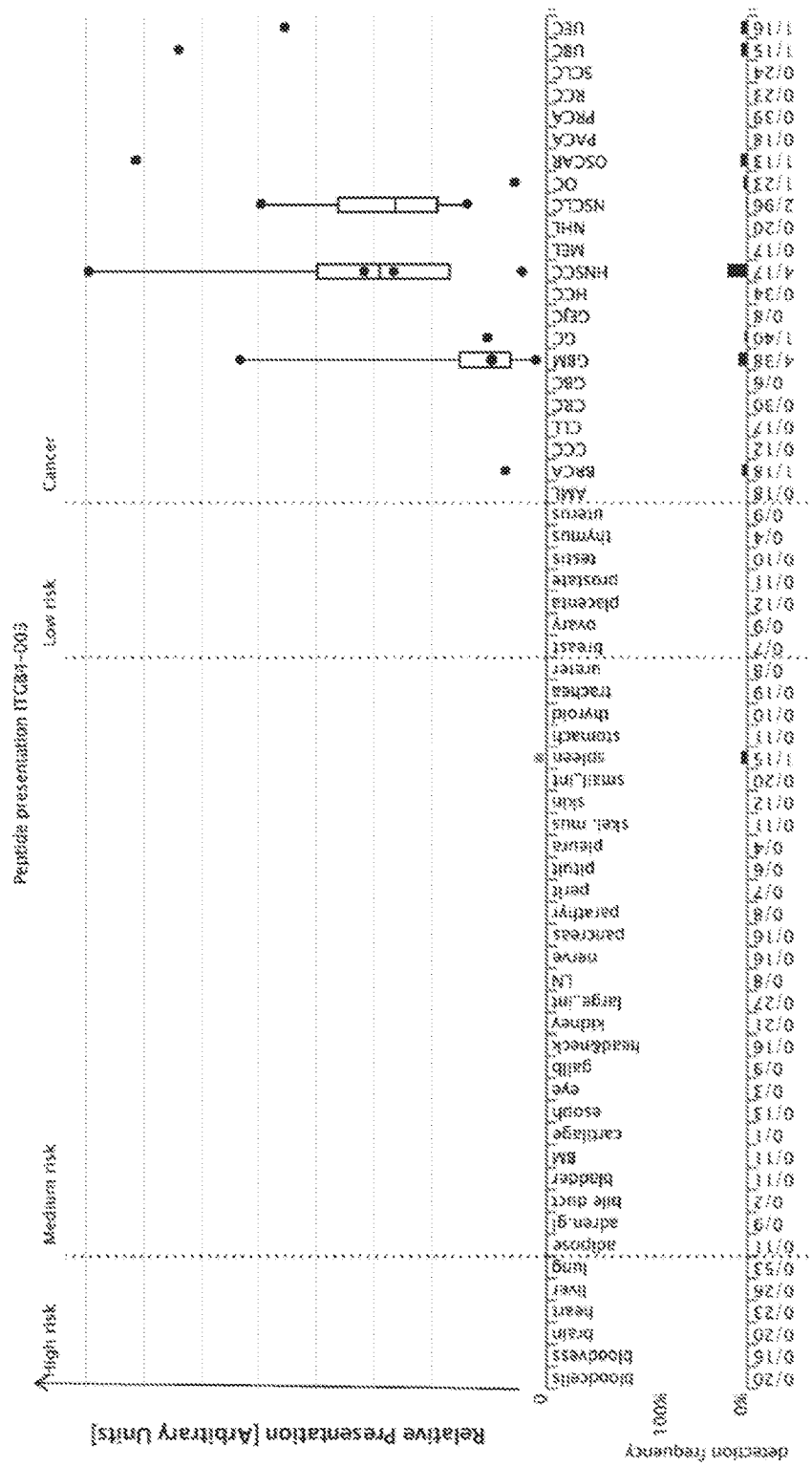

Peptide: QLLQVVVNL (A*02)
SEQ ID NO: 83

Peptide: TLNDGVVVQV (A*02)
SEQ ID NO: 90

Gene: PGLYRP4
Peptide: AIYEGVGWNV
SEQ ID NO: 33

Gene: PAPL
Peptide: KLLPGVQVV
SEQ ID NO: 38

Genes: LGALS7, LGALS7B
Peptide: RLVEVGGDVQL
SEQ ID NO: 53

PEPTIDES AND SCAFFOLDS FOR USE IN IMMUNOTHERAPY AGAINST HEAD AND NECK SQUAMOUS CELL CARCINOMA AND OTHER CANCERS

CROSS REFERENCE TO RELATED APPLICATIONS

This application is a continuation of U.S. patent application Ser. No. 16/162,337, filed 16 Oct. 2018, which is a continuation of U.S. patent application Ser. No. 15/686,679, filed 25 Aug. 2017, which claims the benefit of U.S. Provisional Application Ser. No. 62/379,864, filed 26 Aug. 2016, and German Application No. 102016115974.3, filed 26 Aug. 2016, the content of each of these applications is herein incorporated by reference in their entirety.

This application also is related to PCT/EP2017/071347 filed 24 Aug. 2017, the content of which is incorporated herein by reference in its entirety.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2912919-075004_ST25.txt" created on 28 Dec. 2018, and 25,156 bytes in size) is submitted concurrently with the instant application, and the entire contents of the Sequence Listing are incorporated herein by reference.

FIELD

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

The present invention relates to several novel peptide sequences and their variants derived from HLA class I molecules of human tumor cells that can be used in vaccine compositions for eliciting anti-tumor immune responses, or as targets for the development of pharmaceutically/immunologically active compounds and cells.

BACKGROUND OF THE INVENTION

Head and neck squamous cell carcinomas (HNSCC) are heterogeneous tumors with differences in epidemiology, etiology and treatment (Economopoulou et al., 2016). These tumors are categorized by the area in which they begin. They include cancers of the oral cavity (lips, front two-thirds of the tongue, gums, lining inside the cheeks and lips, floor of the mouth, hard palate), the pharynx (nasopharynx, oropharynx including soft palate, base of the tongue, tonsils, hypopharynx), larynx, paranasal sinuses and nasal cavity and salivary glands (National Cancer Institute, 2015).

HNSCC is the sixth most common malignancy in the world and accounts for about 6% of all cancer cases diagnosed worldwide (Economopoulou et al., 2016). HNSCC is characterized by a wide geographical variation in the incidence and anatomic distribution (Vigneswaran and Williams, 2014). High risk countries are located in South and Southeast Asia (i.e. India, Sri Lanka, Bangladesh, Pakistan). In these regions, squamous cell carcinoma of the oral cavity (OSCC) is the most common cancer in men and the third most common cancer in women (Vigneswaran and Williams, 2014). In Europe, high incidence rates of OSCC are found in regions of France, Hungary, Slovakia and Slovenia. In the United States, HNSCC is the eighths most common cancer among men.

Major risk factors for HNSCC are alcohol and tobacco use. Other HNSCC risk factors include consumption of maté, but also of preserved or salted foods, use of *betel* quid, occupational exposure to wood dust, asbestos and synthetic fibers, radiation exposure, infection with cancer-causing types of human papillomavirus (HPV) or Epstein-Barr virus (EBV) and ancestry (particularly Chinese ancestry in nasopharyngeal SCC) (National Cancer Institute, 2015).

While OSCC and laryngeal SCC have decreased in developed countries, the incidence of oropharyngeal SCC has increased. This is attributed to a change in the biologic driver of SCC (HPV-related SCC instead of smoking-related SCC). HPV-related oropharyngeal cancers have increased by 225% from 1988 to 2004 (National Cancer Institute, 2015). HPV-positive HNSCC may represent a distinct disease entity. Those tumors are associated with significantly improved survivals.

Rates of incidence depend on gender: male to female ratio ranges from 2:1 to 4:1 (2014 Review of cancer Medicines on the WHO list of essential medicines). The five-year overall survival rate of patients with HNSCC is 40-50% (World Health Organization, 2014). While early cancers (T1, T2) have cure rates of 70%-95% (Nat Cancer Inst), the majority of patients with HNSCC present with locally advanced disease (Bauml et al., 2016).

Treatment for early HNSCC involves single-modality therapy with either surgery or radiation (World Health Organization, 2014). Advanced cancers are treated by a combination of chemotherapy with surgery and/or radiation therapy.

Chemotherapy includes mostly cisplatin or drug combinations that contain cisplatin like docetaxel, cisplatin, fluorouracil (5-FU) or cisplatin, epirubicin, bleomycin or cisplatin, 5-FU. Isotretinoin (13-cis-retinoic acid) is used in oral cavity SCC and laryngeal SCC, daily for 1 year to reduce the incidence of second tumors (National Cancer Institute, 2015).

HNSCC is considered an immunosuppressive disease, characterized by the dysregulation of immunocompetent cells and impaired cytokine secretion (Economopoulou et al., 2016). Immunotherapeutic strategies differ between HPV-negative and HPV-positive tumors.

In HPV-positive tumors, the viral oncoproteins E6 and E7 represent good targets, as they are continuously expressed by tumor cells and are essential to maintain the transformation status of HPV-positive cancer cells. Several vaccination therapies are currently under investigation in HPV-positive HNSCC, including DNA vaccines, peptide vaccines and vaccines involving dendritic cells (DCs). Additionally, an ongoing phase II clinical trial investigates the efficacy of lymphodepletion followed by autologous infusion of TILs in patients with HPV-positive tumors (Economopoulou et al., 2016).

In HPV-negative tumors, several immunotherapeutic strategies are currently used and under investigation. The chimeric IgG1 anti-EGFR monoclonal antibody cetuximab has been approved by the FDA in combination with chemotherapy as standard first line treatment for recurring/metastatic HNSCC. Other anti-EGFR monoclonal antibodies, including panitumumab, nimotuzumab and zalutumumab, are evaluated in HNSCC. Several immune checkpoint inhibitors are investigated in clinical trials for their use in HNSCC. They include the following antibodies: Ipilimumab (anti-CTLA-4), tremelimumab (anti-CTLA-4), pembrolizumab (anti-PD-1), nivolumab (anti-PD-1), durvalumab (anti-PD-1), anti-KIR, urelumab (anti-CD137), and anti-LAG-3.

Two clinical studies with HNSCC patients evaluated the use of DCs loaded with p53 peptides or apoptotic tumor cells. The immunological responses were satisfactory and side effects were acceptable.

Several studies have been conducted using adoptive T cell therapy (ACT). T cells were induced against either irradiated autologous tumor cells or EBV. Results in disease control and overall survival were promising (Economopoulou et al., 2016).

Considering the severe side-effects and expense associated with treating cancer, there is a need to identify factors that can be used in the treatment of cancer in general and head and neck squamous cell carcinoma in particular. There is also a need to identify factors representing biomarkers for cancer in general and head and neck squamous cell carcinoma in particular, leading to better diagnosis of cancer, assessment of prognosis, and prediction of treatment success.

Immunotherapy of cancer represents an option of specific targeting of cancer cells while minimizing side effects. Cancer immunotherapy makes use of the existence of tumor associated antigens.

The current classification of tumor associated antigens (TAAs) comprises the following major groups:
a) Cancer-testis antigens: The first TAAs ever identified that can be recognized by T cells belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T cells in normal tissues and can therefore be considered as immunologically tumor-specific. Well-known examples for CT antigens are the MAGE family members and NY-ESO-1.
b) Differentiation antigens: These TAAs are shared between tumors and the normal tissue from which the tumor arose. Most of the known differentiation antigens are found in melanomas and normal melanocytes. Many of these melanocyte lineage-related proteins are involved in biosynthesis of melanin and are therefore not tumor specific but nevertheless are widely used for cancer immunotherapy. Examples include, but are not limited to, tyrosinase and Melan-A/MART-1 for melanoma or PSA for prostate cancer.
c) Over-expressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their over-expression in tumor cells can trigger an anticancer response by breaking previously established tolerance. Prominent examples for this class of TAAs are Her-2/neu, survivin, telomerase, or WT1.
d) Tumor-specific antigens: These unique TAAs arise from mutations of normal genes (such as μ-catenin, CDK4, etc.). Some of these molecular changes are associated with neoplastic transformation and/or progression. Tumor-specific antigens are generally able to induce strong immune responses without bearing the risk for autoimmune reactions against normal tissues. On the other hand, these TAAs are in most cases only relevant to the exact tumor on which they were identified and are usually not shared between many individual tumors. Tumor-specificity (or -association) of a peptide may also arise if the peptide originates from a tumor-(-associated) exon in case of proteins with tumor-specific (-associated) isoforms. e) TAAs arising from abnormal post-translational modifications: Such TAAs may arise from proteins which are neither specific nor overexpressed in tumors but nevertheless become tumor associated by post-translational processes primarily active in tumors. Examples for this class arise from altered glycosylation patterns leading to novel epitopes in tumors as for MUC1 or events like protein splicing during degradation which may or may not be tumor specific.
f) Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

T-cell based immunotherapy targets peptide epitopes derived from tumor-associated or tumor-specific proteins, which are presented by molecules of the major histocompatibility complex (MHC). The antigens that are recognized by the tumor specific T lymphocytes, that is, the epitopes thereof, can be molecules derived from all protein classes, such as enzymes, receptors, transcription factors, etc. which are expressed and, as compared to unaltered cells of the same origin, usually up-regulated in cells of the respective tumor.

There are two classes of MHC-molecules, MHC class I and MHC class II. MHC class I molecules are composed of an alpha heavy chain and beta-2-microglobulin, MHC class II molecules of an alpha and a beta chain. Their three-dimensional conformation results in a binding groove, which is used for non-covalent interaction with peptides.

MHC class I molecules can be found on most nucleated cells. They present peptides that result from proteolytic cleavage of predominantly endogenous proteins, defective ribosomal products (DRIPs) and larger peptides. However, peptides derived from endosomal compartments or exogenous sources are also frequently found on MHC class I molecules.

This non-classical way of class I presentation is referred to as cross-presentation in the literature (Brossart and Bevan, 1997; Rock et al., 1990). MHC class II molecules can be found predominantly on professional antigen presenting cells (APCs), and primarily present peptides of exogenous or transmembrane proteins that are taken up by APCs e.g. during endocytosis, and are subsequently processed.

Complexes of peptide and MHC class I are recognized by CD8-positive T cells bearing the appropriate T-cell receptor (TCR), whereas complexes of peptide and MHC class II molecules are recognized by CD4-positive-helper-T cells bearing the appropriate TCR. It is well known that the TCR, the peptide and the MHC are thereby present in a stoichiometric amount of 1:1:1.

CD4-positive helper T cells play an important role in inducing and sustaining effective responses by CD8-positive cytotoxic T cells. The identification of CD4-positive T-cell epitopes derived from tumor associated antigens (TAA) is of immense importance for the development of pharmaceutical products for triggering anti-tumor immune responses (Gnjatic et al., 2003). At the tumor site, T helper cells, support a cytotoxic T cell- (CTL-) friendly cytokine milieu (Mortara et al., 2006) and attract effector cells, e.g. CTLs, natural killer (NK) cells, macrophages, and granulocytes (Hwang et al., 2007).

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have been found to express MHC class II molecules (Dengjel et al., 2006). Elongated (longer) peptides of the invention can act as MHC class II active epitopes.

T-helper cells, activated by MHC class II epitopes, play an important role in orchestrating the effector function of CTLs in anti-tumor immunity. T-helper cell epitopes that trigger a T-helper cell response of the TH1 type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

It was shown in mammalian animal models, e.g., mice, that even in the absence of CD8-positive T lymphocytes, CD4-positive T cells are sufficient for inhibiting manifestation of tumors via inhibition of angiogenesis by secretion of interferon-gamma (IFNγ) (Beatty and Paterson, 2001; Mumberg et al., 1999). There is evidence for CD4 T cells as direct anti-tumor effectors (Braumuller et al., 2013; Tran et al., 2014).

Since the constitutive expression of HLA class II molecules is usually limited to immune cells, the possibility of isolating class II peptides directly from primary tumors was previously not considered possible. However, Dengjel et al. were successful in identifying a number of MHC Class II epitopes directly from tumors (WO 2007/028574, EP 1 760 088 B1).

Since both types of response, CD8 and CD4 dependent, contribute jointly and synergistically to the anti-tumor effect, the identification and characterization of tumor-associated antigens recognized by either CD8+ T cells (ligand: MHC class I molecule+peptide epitope) or by CD4-positive T-helper cells (ligand: MHC class II molecule+peptide epitope) is important in the development of tumor vaccines.

For an MHC class I peptide to trigger (elicit) a cellular immune response, it also must bind to an MHC-molecule. This process is dependent on the allele of the MHC-molecule and specific polymorphisms of the amino acid sequence of the peptide. MHC-Class-1-binding peptides are usually 8-12 amino acid residues in length and usually contain two conserved residues ("anchors") in their sequence that interact with the corresponding binding groove of the MHC-molecule. In this way, each MHC allele has a "binding motif" determining which peptides can bind specifically to the binding groove.

In the MHC class I dependent immune reaction, peptides not only have to be able to bind to certain MHC class I molecules expressed by tumor cells, they subsequently also have to be recognized by T cells bearing specific T cell receptors (TCR).

For proteins to be recognized by T-lymphocytes as tumor-specific or -associated antigens, and to be used in a therapy, particular prerequisites must be fulfilled. The antigen should be expressed mainly by tumor cells and not, or in comparably small amounts, by normal healthy tissues. In a preferred embodiment, the peptide should be over-presented by tumor cells as compared to normal healthy tissues. It is furthermore desirable that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to their function, e.g. in cell cycle control or suppression of apoptosis. Additionally, downstream targets of the proteins directly causative for a transformation may be up-regulated and thus may be indirectly tumor-associated. Such indirect tumor-associated antigens may also be targets of a vaccination approach (Singh-Jasuja et al., 2004). It is essential that epitopes are present in the amino acid sequence of the antigen, in order to ensure that such a peptide ("immunogenic peptide"), being derived from a tumor associated antigen, leads to an in vitro or in vivo T-cell-response.

Basically, any peptide able to bind an MHC molecule may function as a T-cell epitope. A prerequisite for the induction of an in vitro or in vivo T-cell-response is the presence of a T cell having a corresponding TCR and the absence of immunological tolerance for this particular epitope.

Therefore, TAAs are a starting point for the development of a T cell based therapy including but not limited to tumor vaccines. The methods for identifying and characterizing the TAAs are usually based on the use of T-cells that can be isolated from patients or healthy subjects, or they are based on the generation of differential transcription profiles or differential peptide expression patterns between tumors and normal tissues. However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and the immunological tolerance for this particular epitope needs to be absent or minimal. In a very preferred embodiment of the invention it is therefore important to select only those over- or selectively presented peptides against which a functional and/or a proliferating T cell can be found. Such a functional T cell is defined as a T cell, which upon stimulation with a specific antigen can be clonally expanded and is able to execute effector functions ("effector T cell").

In case of targeting peptide-MHC by specific TCRs (e.g. soluble TCRs) and antibodies or other binding molecules (scaffolds) according to the invention, the immunogenicity of the underlying peptides is secondary. In these cases, the presentation is the determining factor.

SUMMARY OF THE INVENTION

In a first aspect of the present invention, the present invention relates to a peptide comprising an amino acid sequence selected from the group consisting of SEQ ID NO: 1 to SEQ ID NO: 91 or a variant sequence thereof which is at least 77%, preferably at least 88%, homologous (preferably at least 77% or at least 88% identical) to SEQ ID NO: 1 to SEQ ID NO: 91, wherein said variant binds to MHC and/or induces T cells cross-reacting with said peptide, or a pharmaceutical acceptable salt thereof, wherein said peptide is not the underlying full-length polypeptide.

The present invention further relates to a peptide of the present invention comprising a sequence that is selected from the group consisting of SEQ ID NO: 1 to SEQ ID NO: 91 or a variant thereof, which is at least 77%, preferably at least 88%, homologous (preferably at least 77% or at least 88% identical) to SEQ ID NO: 1 to SEQ ID NO: 91, wherein said peptide or variant thereof has an overall length of between 8 and 100, preferably between 8 and 30, and most preferred of between 8 and 14 amino acids.

The following tables show the peptides according to the present invention, their respective SEQ ID NOs, and the prospective source (underlying) genes for these peptides. All peptides in Table 1 and Table 2 bind to HLA-A*02. The peptides in Table 2 have been disclosed before in large listings as results of high-throughput screenings with high error rates or calculated using algorithms, but have not been associated with cancer at all before. The peptides in Table 3 are additional peptides that may be useful in combination with the other peptides of the invention. The peptides in Table 4A and B are furthermore useful in the diagnosis and/or treatment of various other malignancies that involve an over-expression or over-presentation of the respective underlying polypeptide.

TABLE 1

Peptides according to the present invention.

| SEQ ID No. | Sequence | Gene ID(s) | Official Gene Symbol(s) |
|---|---|---|---|
| 1 | GLAGGFGGPGFPV | 286887, 3853, 3854 | KRT6C, KRT6A, KRT6B |
| 2 | PVCPPGGIQEV | 286887, 3848, 3852, 3853, 3854, 9119 | KRT6C, KRT1, KRT5, KRT6A, KRT6B, KRT75 |
| 3 | SLYGLGGSKRISI | 286887, 3853, 3854 | KRT6C, KRT6A, KRT6B |
| 4 | ILDINDNPPV | 100653137, 1830, 64072 | DSG3, CDH23 |
| 5 | VCPPGGIQEV | 286887, 3848, 3852, 3853, 3854, 9119 | KRT6C, KRT1, KRT5, KRT6A, KRT6B, KRT75 |
| 6 | ALYDAELSQM | 286887, 3853, 3854 | KRT6C, KRT6A, KRT6B |
| 7 | ALEEANADLEV | 3860, 3861, 3866, 3868, 400578, 644945, 729252 | KRT13, KRT14, KRT15, KRT16, KRT16P2, KRT16P3, KRT16P1 |
| 8 | AQLNIGNVLPV | 6132 | RPL8 |
| 9 | STASAITPSV | 3852 | KRT5 |
| 10 | TLWPATPPKA | 647024 | C6orf132 |
| 11 | VLFSSPPVI | 5621 | PRNP |
| 12 | TLTDEINFL | 286887, 3853, 3854 | KRT6C, KRT6A, KRT6B |
| 13 | SLVSYLDKV | | unknown gene |
| 14 | RIMEGIPTV | 242 | ALOX12B |
| 15 | SMLNNIINL | 5317 | PKP1 |
| 16 | ALKDSVQRA | 10765 | KDM5B |
| 17 | SIWPALTQV | 100381270 | ZBED6 |
| 18 | YLYPDLSRL | 6538 | SLC6A11 |
| 19 | ALAKLLPLL | 5655 | KLK10 |
| 20 | YLINEIDRIRA | 667 | DST |
| 21 | FLHEPFSSV | 122665, 84659 | RNASE8, RNASE7 |
| 22 | KLPEPCPSTV | 6707 | SPRR3 |
| 23 | SLPESGLLSV | 2178 | FANCE |
| 24 | LLIAINPQV | 9635 | CLCA2 |

TABLE 1-continued

Peptides according to the present invention.

| SEQ ID No. | Sequence | Gene ID(s) | Official Gene Symbol(s) |
|---|---|---|---|
| 25 | SLCPPGGIQEV | 196374 | KRT78 |
| 26 | TLVDENQSWYL | 341208 | HEPHL1 |
| 27 | YLAEPQWAV | 2196 | FAT2 |
| 28 | AVDPVSGSLYV | 57451 | TENM2 |
| 29 | RLLPDLDEV | 121551 | BTBD11 |
| 30 | TLASLGYAVV | 91039 | DPP9 |
| 31 | HLATVKLLV | 54101 | RIPK4 |
| 32 | IQDAEGAIHEV | 165904 | XIRP1 |
| 33 | AIYEGVGWNV | 57115 | PGLYRP4 |
| 34 | ALDTFSVQV | 171177 | RHOV |
| 35 | ALVGDVILTV | 2196 | FAT2 |
| 36 | GLWSSIFSL | 123745 | PLA2G4E |
| 37 | ILLEDVFQL | 285973 | ATG9B |
| 38 | KLLPGVQYV | 390928 | PAPL |
| 39 | LLPEDDTRDNV | 1001 | CDH3 |
| 40 | LLTPLNLQI | 286887, 3852, 3853, 3854 | KRT6C, KRT5, KRT6A, KRT6B |
| 41 | RLNGEGVGQVNISV | 3853, 3854 | KRT6A, KRT6B |
| 42 | ALYTSGHLL | 5653 | KLK6 |
| 43 | AVLGGKLYV | 9903 | KLHL21 |
| 44 | GLGDDSFPI | 2125 | EVPL |
| 45 | GLIEWLENTV | 5591 | PRKDC |
| 46 | GLISSIEAQL | 3860 | KRT13 |
| 47 | QLLEGELETL | 5493 | PPL |
| 48 | YLLDYPNNL | 26057 | ANKRD17 |
| 49 | YLWEAHTNI | 729830 | FAM160A1 |
| 50 | ALSNVVHKV | 5268 | SERPINB5 |
| 51 | FLIPSIIFA | 150696 | PROM2 |
| 52 | LLFTGLVSGV | 284434 | NWD1 |
| 53 | RLVEVGGDVQL | 3963, 653499 | LGALS7, LGALS7B |
| 54 | RLSGEGVGPV | 3852 | KRT5 |
| 55 | VLNVGVAEV | 285848 | PNPLA1 |
| 56 | FLQLETEQV | 64426 | SUDS3 |
| 57 | AILGFALSEA | 516, 517, 518 | ATP5G1, ATP5G2, ATP5G3 |
| 58 | SLSDIQPCL | 3691 | ITGB4 |
| 59 | YLQNEVFGL | 1832 | DSP |
| 60 | SLGNFKDDLL | 23650 | TRIM29 |
| 61 | FVAGYIAGV | 5250 | SLC25A3 |
| 62 | ILSSACYTV | 5317 | PKP1 |
| 63 | ALMDEINFMKM | 3852 | KRT5 |
| 64 | KILEJLFVJL | | unknown gene |
| 65 | ALWGFFPVLL | 56851 | EMC7 |
| 66 | TLLSEIAEL | 84629 | TNRC18 |
| 67 | AQLNLIWQL | 80381 | CD276 |
| 68 | KILEMDDPRA | 6512 | SLC1A7 |
| 69 | YVMESMTYL | 28976 | ACAD9 |
| 70 | FLFPAFLTA | 2150 | F2RL1 |
| 71 | SLFPYVVLI | 55117 | SLC6A15 |
| 72 | SLDGNPLAV | 25987 | TSKU |
| 73 | YIDPYKLLPL | 54433 | GAR1 |
| 74 | SLTSFLISL | 101060198, 7851 | MALL |
| 75 | ALASAPTSV | 80004 | ESRP2 |
| 76 | ILFDEVLTFA | 83666 | PARP9 |
| 77 | SLRAFLMPI | 79901 | CYBRD1 |
| 78 | VLYGDVEEL | 10970 | CKAP4 |
| 79 | GLHQDFPSVVL | 51056 | LAP3 |
| 80 | GLYGIKDDVFL | 3939 | LDHA |

J = phospho-serine

TABLE 2

Additional peptides according to the present invention with no prior known cancer association.

| SEQ ID No. | Sequence | Gene ID(s) | Official Gene Symbol(s) |
|---|---|---|---|
| 81 | VLAENPDIFAV | 6541 | SLC7A1 |
| 82 | VLDINDNPPV | 120114, 1828, 2195 | FAT3, DSG1, FAT1 |
| 83 | QLLQYVYNL | 4173 | MCM4 |
| 84 | ALMAGCIQEA | 1026 | CDKN1A |
| 85 | QLIEKITQV | 114827 | FHAD1 |
| 86 | SLQERQVFL | 9333 | TGM5 |
| 87 | ALPEPSPAA | 5339 | PLEC |
| 88 | LMAPAPSTV | 7071 | KLF10 |
| 89 | VLDEGLTSV | 25909, 285116 | AHCTF1, AHCTF1P1 |
| 90 | TLNDGVVVQV | 10146 | G3BP1 |
| 91 | MLFENMGAYTV | 4953 | ODC1 |

TABLE 3

Peptides useful for e.g. personalized cancer therapies.

| SEQ ID No. | Sequence | Gene ID(s) | Official Gene Symbol(s) |
|---|---|---|---|
| 92 | ILLDVKTRL | 3728, 3861, 3868, 3872 | JUP, KRT14, KRT16, KRT17 |
| 93 | ALSNVIHKV | 5268 | SERPINB5 |
| 94 | SIFEGLLSGV | 2709 | GJB5 |
| 95 | SLDENSDQQV | 6273 | S100A2 |
| 96 | FQLDPSSGVLVTV | 2196 | FAT2 |
| 97 | LILESIPVV | 5597 | MAPK6 |
| 98 | SLYKGLLSV | 25788 | RAD54B |
| 99 | TASAITPSV | 3852 | KRT5 |
| 100 | VLVSDGVHSV | 1952 | CELSR2 |
| 101 | GLLPSAESIKL | 132989 | C4orf36 |
| 102 | TLAELQPPVQL | 157922 | CAMSAP1 |
| 103 | VLAEGGEGV | 10630 | PDPN |
| 104 | SLSPVILGV | 26525 | IL36RN |
| 105 | STYGGGLSV | 3861, 3868 | KRT14, KRT16 |
| 106 | VLVDQSWVL | 5655 | KLK10 |
| 107 | YLEEDVYQL | 23255 | SOGA2 |
| 108 | SLYNLGGSKRISI | 3852 | KRT5 |
| 109 | KIQEILTQV | 10643 | IGF2BP3 |
| 110 | LLPPPPPPA | 9509 | ADAMTS2 |
| 111 | SLAPGDVVRQV | 79729 | SH3D21 |
| 112 | ALLDGGSEAYWRV | 84985 | FAM83A |
| 113 | NLMASQPQL | 5317 | PKP1 |
| 114 | VLVPYEPPQV | 8626 | TP63 |
| 115 | VTAAYMDTVSL | 7498 | XDH |
| 116 | SLWPSPEQL | 90480 | GADD45GIP1 |
| 117 | GLAFSLYQA | 871 | SERPINH1 |
| 118 | TLLQEQGTKTV | 286887, 3852, 3853, 3854 | KRT6C, KRT5, KRT6A, KRT6B |
| 119 | GLLDPSVFHV | 79050 | NOC4L |
| 120 | YLVAKLVEV | 10277 | UBE4B |
| 121 | SLYGYLRGA | 9790 | BMS1 |
| 122 | ILDEAGVKYFL | 113828 | FAM83F |
| 123 | LLSGDLIFL | 2709 | GJB5 |
| 124 | YMLDIFHEV | 3038 | HAS3 |
| 125 | ALNPEIVSV | 5277 | PIGA |
| 126 | ILVDWLVEV | 85417, 890, 8900 | CCNB3, CCNA2, CCNA1 |
| 127 | SLFGKKYIL | 2274 | FHL2 |
| 128 | TLHRETFYL | 9134 | CCNE2 |
| 129 | SLSGEIILHSV | 121441 | NEDD1 |
| 130 | TLDGAAVNQV | 3918 | LAMC2 |
| 131 | LQLDKEFQL | 24140 | FTSJ1 |
| 132 | TLYPGRFDYV | 338322 | NLRP10 |
| 133 | LLLPLQILL | 5650 | KLK7 |
| 134 | ILIGETIKI | 5742, 5743 | PTGS1, PTGS2 |
| 135 | GLFSQHFNL | 1789 | DNMT3B |
| 136 | SLMEPPAVLLL | 8900 | CCNA1 |
| 137 | GLAPFLLNAV | 101060689, 154761, 285966 | FAM115C |
| 138 | ALLTGIISKA | 23165 | NUP205 |
| 139 | QLGPVPVTI | 285966 | FAM115C |
| 140 | YLFENISQL | 57115 | PGLYRP4 |
| 141 | FLNPDEVHAI | 81610 | FAM83D |
| 142 | SLVSEQLEPA | 11187 | PKP3 |
| 143 | YVYQNNIYL | 2191 | FAP |
| 144 | KISTITPQI | 996 | CDC27 |
| 145 | LLYGKYVSV | 84065 | TMEM222 |
| 146 | GLLEELVTV | 642475 | MROH6 |
| 147 | ILMDPSPEYA | 1786 | DNMT1 |
| 148 | LLFDAPDLRL | 55561 | CDC42BPG |
| 149 | VLLNINGIDL | 222484 | LNX2 |
| 150 | ILAEEPIYIRV | 55655 | NLRP2 |
| 151 | QLCDLNAEL | 3833 | KIFC1 |
| 152 | SLWQDIPDV | 128272 | ARHGEF19 |
| 153 | VLFLGKLLV | 204962 | SLC44A5 |
| 154 | KMWEELPEVV | 622 | BDH1 |
| 155 | GLLDNPELRV | 26263 | FBXO22 |
| 156 | ALINDILGELVKL | 85463 | ZC3H12C |

The present invention furthermore generally relates to the peptides according to the present invention for use in the treatment of proliferative diseases, such as, for example, acute myelogenous leukemia, breast cancer, bile duct cancer, brain cancer, chronic lymphocytic leukemia, colorectal carcinoma, esophageal cancer, gallbladder cancer, gastric cancer, hepatocellular cancer, melanoma, non-Hodgkin lymphoma, non-small cell lung cancer, ovarian cancer, pancreatic cancer, prostate cancer, renal cell cancer, small cell lung cancer, urinary bladder cancer and uterine cancer.

Particularly preferred are the peptides—alone or in combination—according to the present invention selected from the group consisting of SEQ ID NO: 1 to SEQ ID NO: 91. More preferred are the peptides—alone or in combination—selected from the group consisting of SEQ ID NO: 1 to SEQ ID NO: 31 (see Table 1), and their uses in the immunotherapy of head and neck squamous cell carcinoma, acute myelogenous leukemia, breast cancer, bile duct cancer, brain cancer, chronic lymphocytic leukemia, colorectal carcinoma, esophageal cancer, gallbladder cancer, gastric cancer, hepatocellular cancer, melanoma, non-Hodgkin lymphoma, non-small cell lung cancer, ovarian cancer, pancreatic cancer, prostate cancer, renal cell cancer, small cell lung cancer, urinary bladder cancer, uterine cancer, and preferably head and neck squamous cell carcinoma.

As shown in the following Table 4, many of the peptides according to the present invention are also found on other tumor types and can, thus, also be used in the immunotherapy of other indications. Also refer to FIGS. 1A-1Q and Example 1.

TABLE 4A

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation as tested were: adipose tissue, adrenal gland, bile duct, blood cells, blood vessel, bone marrow, brain, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thymus, thyroid gland, trachea, ureter, urinary bladder.

| SEQ ID No | Sequence | Other relevant organs/diseases |
|---|---|---|
| 1 | GLAGGFGGPGFPV | Gallbladder Cancer, Bile Duct Cancer |
| 2 | PVCPPGGIQEV | NSCLC, SCLC |
| 3 | SLYGLGGSKRISI | Esophageal Cancer, Urinary bladder cancer |
| 4 | ILDINDNPPV | BRCA, Esophageal Cancer, Urinary bladder cancer |
| 7 | ALEEANADLEV | Esophageal Cancer, Urinary bladder cancer |
| 8 | AQLNIGNVLPV | Melanoma, Esophageal Cancer |
| 9 | STASAITPSV | Melanoma |
| 10 | TLWPATPPKA | Gallbladder Cancer, Bile Duct Cancer |
| 11 | VLFSSPPVI | Melanoma |
| 15 | SMLNNIINL | Urinary bladder cancer |
| 16 | ALKDSVQRA | AML, BRCA, Melanoma, Esophageal Cancer, Urinary bladder cancer, Uterine Cancer |
| 17 | SIWPALTQV | SCLC, AML, BRCA, Melanoma, Uterine Cancer, Gallbladder Cancer, Bile Duct Cancer |
| 18 | YLYPDLSRL | Brain Cancer |
| 19 | ALAKLLPLL | Esophageal Cancer, Urinary bladder cancer, Uterine Cancer |
| 20 | YLINEIDRIRA | NSCLC, Urinary bladder cancer |
| 21 | FLHEPFSSV | Urinary bladder cancer |
| 23 | SLPESGLLSV | Esophageal Cancer |
| 24 | LLIAINPQV | AML, Urinary bladder cancer |
| 27 | YLAEPQWAV | Esophageal Cancer, Urinary bladder cancer |
| 29 | RLLPDLDEV | AML |
| 31 | HLATVKLLV | Urinary bladder cancer, Uterine Cancer |
| 32 | IQDAEGAIHEV | NHL, Melanoma, Esophageal Cancer, Urinary bladder cancer |
| 37 | ILLEDVFQL | Gallbladder Cancer, Bile Duct Cancer |
| 39 | LLPEDDTRDNV | BRCA, Esophageal Cancer, Urinary bladder cancer |
| 41 | RLNGEGVGQVNISV | Esophageal Cancer |
| 42 | ALYTSGHLL | Esophageal Cancer, Gallbladder Cancer, Bile Duct Cancer |
| 43 | AVLGGKLYV | CLL, NHL, AML, Melanoma, Uterine Cancer |
| 45 | GLIEWLENTV | SCLC, OC, Urinary bladder cancer |
| 46 | GLISSIEAQL | Esophageal Cancer, Urinary bladder cancer, Uterine Cancer |
| 47 | QLLEGELETL | Urinary bladder cancer, Uterine Cancer |
| 48 | YLLDYPNNL | NHL, BRCA, Melanoma, Esophageal Cancer, Urinary bladder cancer, Uterine Cancer, Gallbladder Cancer, Bile Duct Cancer |
| 49 | YLWEAHTNI | Esophageal Cancer, Uterine Cancer |
| 50 | ALSNVVHKV | GC, BRCA, Esophageal Cancer, Urinary bladder cancer |
| 51 | FLIPSIIFA | Urinary bladder cancer, Uterine Cancer |
| 52 | LLFTGLVSGV | Esophageal Cancer |
| 53 | RLVEVGGDVQL | Esophageal Cancer, Urinary bladder cancer |
| 54 | RLSGEGVGPV | Esophageal Cancer |
| 56 | FLQLETEQV | BRCA, Melanoma, Urinary bladder cancer, Uterine Cancer |
| 57 | AILGFALSEA | AML, BRCA, Melanoma, Uterine Cancer, Gallbladder Cancer, Bile Duct Cancer |
| 58 | SLSDIQPCL | Brain Cancer, BRCA, Esophageal Cancer, Urinary bladder cancer, Uterine Cancer |
| 59 | YLQNEVFGL | SCLC, NHL |
| 60 | SLGNFKDDLL | NHL, Esophageal Cancer, Urinary bladder cancer |
| 61 | FVAGYIAGV | NSCLC, SCLC, RCC, Brain Cancer, GC, CLL, NHL, Esophageal Cancer, Gallbladder Cancer, Bile Duct Cancer |
| 62 | ILSSACYTV | RCC, BRCA, Esophageal Cancer |
| 63 | ALMDEINFMKM | NSCLC, SCLC, NHL |
| 64 | KILEJLFVJL | NSCLC, Urinary bladder cancer, Gallbladder Cancer, Bile Duct Cancer |
| 65 | ALWGFFPVLL | CLL, Melanoma |
| 66 | TLLSEIAEL | CLL, NHL, AML, Melanoma, OC, Uterine Cancer |
| 67 | AQLNLIWQL | SCLC, Melanoma, OC, Uterine Cancer, Gallbladder Cancer, Bile Duct Cancer |
| 69 | YVMESMTYL | Urinary bladder cancer, Gallbladder Cancer, Bile Duct Cancer |
| 70 | FLFPAFLTA | AML, Gallbladder Cancer, Bile Duct Cancer |
| 71 | SLFPYVVLI | Melanoma |
| 72 | SLDGNPLAV | Esophageal Cancer, Uterine Cancer, Gallbladder Cancer, Bile Duct Cancer |
| 73 | YIDPYKLLPL | CLL, NHL, AML, Melanoma |
| 74 | SLTSFLISL | Urinary bladder cancer |
| 75 | ALASAPTSV | BRCA, Esophageal Cancer, Uterine Cancer, Gallbladder Cancer, Bile Duct Cancer |
| 76 | ILFDEVLTFA | CLL, NHL, AML, BRCA, Uterine Cancer, Gallbladder Cancer, Bile Duct Cancer |
| 77 | SLRAFLMPI | AML |
| 78 | VLYGDVEEL | CLL, Urinary bladder cancer, Gallbladder Cancer, Bile Duct Cancer |
| 79 | GLHQDFPSVVL | NHL, BRCA, Uterine Cancer |
| 81 | VLAENPDIFAV | SCLC, MCC, Melanoma, Urinary bladder cancer |
| 82 | VLDINDNPPV | Melanoma |
| 83 | QLLQYVYNL | SCLC, NHL, AML, Uterine Cancer |
| 85 | QLIEKITQV | SCLC, NHL, Melanoma, Urinary bladder cancer, Gallbladder Cancer, Bile Duct Cancer |
| 86 | SLQERQVFL | NHL, Urinary bladder cancer |
| 87 | ALPEPSPAA | RCC, NHL, Melanoma, Gallbladder Cancer, Bile Duct Cancer |
| 88 | LMAPAPSTV | Brain Cancer, Esophageal Cancer, Urinary bladder cancer |
| 89 | VLDEGLTSV | SCLC, RCC, CLL, NHL, BRCA, Melanoma, Urinary bladder cancer, Uterine Cancer |
| 90 | TLNDGVVVQV | RCC, CLL, NHL, Esophageal Cancer, Urinary bladder cancer, Uterine Cancer |
| 91 | MLFENMGAYTV | SCLC, CLL, NHL, Uterine Cancer |

NSCLC = non-small cell lung cancer, SCLC = small cell lung cancer, RCC = kidney cancer, CRC = colon or rectum cancer, GC = stomach cancer, HCC = liver cancer, PC = pancreatic cancer, PrC = prostate cancer, leukemia, BRCA = breast cancer, OC = ovarian cancer, NHL = non-Hodgkin lymphoma, AML = acute myelogenous leukemia, CLL = chronic lymphatic leukemia

TABLE 4B

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, esophagus, eye, gallbladder, heart, kidney, liver, lung, lymph node, white blood cells, pancreas, parathyroid gland, peripheral nerve, peritoneum, pituitary, pleura, rectum, salivary gland, skeletal muscle, skin, small intestine, spleen, stomach, thymus, thyroid gland, trachea, ureter, urinary bladder, vein.

| SEQ ID No | Sequence | Additional Entities |
|---|---|---|
| 2 | PVCPPGGIQEV | Esophageal Cancer |
| 6 | ALYDAELSQM | Esophageal Cancer |
| 8 | AQLNIGNVLPV | Urinary bladder cancer |
| 9 | STASAITPSV | Esophageal Cancer |
| 16 | ALKDSVQRA | HCC |
| 43 | AVLGGKLYV | RCC, GC, HCC |
| 45 | GLIEWLENTV | HCC |
| 47 | QLLEGELETL | OC |
| 50 | ALSNVVHKV | NSCLC |
| 51 | FLIPSIIFA | OC |
| 56 | FLQLETEQV | OC |
| 57 | AILGFALSEA | HCC |
| 60 | SLGNFKDDLL | NSCLC |
| 61 | FVAGYIAGV | HCC |
| 65 | ALWGFFPVLL | HCC |
| 66 | TLLSEIAEL | HCC |
| 73 | YIDPYKLLPL | BRCA, Urinary bladder cancer |
| 75 | ALASAPTSV | HCC |
| 88 | LMAPAPSTV | Melanoma |
| 89 | VLDEGLTSV | GC |

NSCLC = non-small cell lung cancer, HCC = liver cancer, BRCA = breast cancer, RCC = renal cell carcinoma, GC = gastric cancer, OC = ovarian cancer.

Thus, another aspect of the present invention relates to the use of at least one peptide according to the present invention according to any one of SEQ ID No. 1, 10, 17, 37, 42, 48, 57, 61, 67, 69, 70, 72, 75, 76, 78, and 87 for the—in one preferred embodiment combined—treatment of gallbladder cancer and/or bile duct cancer.

Thus, another aspect of the present invention relates to the use of at least one peptide according to the present invention according to any one of SEQ ID No. 2, 20, 50, 60, 61, 63, and 64 for the—in one preferred embodiment combined—treatment of NSCLC.

Thus, another aspect of the present invention relates to the use of at least one peptide according to the present invention according to any one of SEQ ID No. 2, 17, 45, 59, 61, 63, 67, 81, 83, 85, 89, and 91 for the—in one preferred embodiment combined—treatment of SCLC.

Thus, another aspect of the present invention relates to the use of at least one peptide according to the present invention according to any one of SEQ ID No. 2, 3, 4, 6, 7, 8, 9, 16, 19, 23, 27, 32, 39, 41, 42, 46, 48, 49, 50, 52, 53, 54, 58, 60, 61, 62, 72, 75, 88, and 90 for the—in one preferred embodiment combined—treatment of esophageal cancer.

Thus, another aspect of the present invention relates to the use of at least one peptide according to the present invention according to any one of SEQ ID No. 3, 4, 7, 8, 15, 16, 19, 20, 21, 24, 27, 31, 32, 39, 45, 46, 47, 48, 50, 51, 53, 56, 58, 60, 64, 69, 73, 74, 78, 81, 85, 86, 88, 89, and 90 for the—in one preferred embodiment combined—treatment of urinary bladder cancer.

Thus, another aspect of the present invention relates to the use of at least one peptide according to the present invention according to any one of SEQ ID No. 4, 16, 17, 39, 48, 50, 56, 57, 58, 62, 73, 75, 76, 79, and 89, for the—in one preferred embodiment combined—treatment of BRCA.

Thus, another aspect of the present invention relates to the use of at least one peptide according to the present invention according to any one of SEQ ID No. 8, 9, 11, 16, 17, 32, 43, 48, 56, 57, 65, 66, 67, 71, 73, 81, 82, 85, 87, 88, and 89 for the—in one preferred embodiment combined—treatment of melanoma.

Thus, another aspect of the present invention relates to the use of at least one peptide according to the present invention according to any one of SEQ ID No. 16, 17, 24, 29, 43, 57, 66, 70, 73, 76, 77, and 83 for the—in one preferred embodiment combined—treatment of AML.

Thus, another aspect of the present invention relates to the use of at least one peptide according to the present invention according to any one of SEQ ID No. 16, 17, 19, 31, 43, 46, 47, 48, 49, 51, 56, 57, 58, 66, 67, 72, 75, 76, 79, 83, 89, 90, and 91 for the—in one preferred embodiment combined—treatment of uterine cancer.

Thus, another aspect of the present invention relates to the use of at least one peptide according to the present invention according to any one of SEQ ID No. 18, 58, 61, and 88 for the—in one preferred embodiment combined—treatment of brain cancer.

Thus, another aspect of the present invention relates to the use of at least one peptide according to the present invention according to any one of SEQ ID No. 32, 43, 48, 59, 60, 61, 63, 66, 73, 76, 79, 83, 85, 86, 87, 89, 90, and 91 for the—in one preferred embodiment combined—treatment of NHL.

Thus, another aspect of the present invention relates to the use of at least one peptide according to the present invention according to any one of SEQ ID No. 43, 61, 65, 66, 73, 76, 78, 89, 90, and 91 for the—in one preferred embodiment combined—treatment of CLL.

Thus, another aspect of the present invention relates to the use of at least one peptide according to the present invention according to any one of SEQ ID No. 45, 47, 51, 56, 66, and 67 for the—in one preferred embodiment combined—treatment of OC.

Thus, another aspect of the present invention relates to the use of at least one peptide according to the present invention according to any one of SEQ ID No. 43, 50, 89, and 61 for the—in one preferred embodiment combined—treatment of GC.

Thus, another aspect of the present invention relates to the use of at least one peptide according to the present invention according to any one of SEQ ID No. 16, 43, 45, 57, 61, 65, 66, and 75 for the—in one preferred embodiment combined—treatment of HCC.

Thus, another aspect of the present invention relates to the use of at least one peptide according to the present invention according to any one of SEQ ID No. 43, 61, 62, 87, 89, and 90 for the—in one preferred embodiment combined—treatment of RCC.

Thus, another aspect of the present invention relates to the use of the peptides according to the present invention for the—preferably combined—treatment of a proliferative disease selected from the group of head and neck squamous cell carcinoma, acute myelogenous leukemia, breast cancer, bile duct cancer, brain cancer, chronic lymphocytic leukemia, colorectal carcinoma, esophageal cancer, gallbladder cancer, gastric cancer, hepatocellular cancer, melanoma, non-Hodgkin lymphoma, non-small cell lung cancer, ovarian cancer, pancreatic cancer, prostate cancer, renal cell cancer, small cell lung cancer, urinary bladder cancer and uterine cancer.

The present invention furthermore relates to peptides according to the present invention that have the ability to bind to a molecule of the human major histocompatibility complex (MHC) Class-I or—in an elongated form, such as a length-variant—MHC class-II.

The present invention further relates to the peptides according to the present invention wherein said peptides (each) consist or consist essentially of an amino acid sequence according to SEQ ID NO: 1 to SEQ ID NO: 91.

The present invention further relates to the peptides according to the present invention, wherein said peptide is modified and/or includes non-peptide bonds.

The present invention further relates to the peptides according to the present invention, wherein said peptide is part of a fusion protein, in particular fused to the N-terminal amino acids of the HLA-DR antigen-associated invariant chain (Ii), or fused to (or into the sequence of) an antibody, such as, for example, an antibody that is specific for dendritic cells.

The present invention further relates to a nucleic acid, encoding the peptides according to the present invention. The present invention further relates to the nucleic acid according to the present invention that is DNA, cDNA, PNA, RNA or combinations thereof.

The present invention further relates to an expression vector capable of expressing and/or expressing a nucleic acid according to the present invention.

The present invention further relates to a peptide according to the present invention, a nucleic acid according to the present invention or an expression vector according to the present invention for use in the treatment of diseases and in medicine, in particular in the treatment of cancer.

The present invention further relates to antibodies that are specific against the peptides according to the present invention or complexes of said peptides according to the present invention with MHC, and methods of making these.

The present invention further relates to T-cell receptors (TCRs), in particular soluble TCR (sTCRs) and cloned TCRs engineered into autologous or allogeneic T cells, and methods of making these, as well as NK cells or other cells bearing said TCR or cross-reacting with said TCRs.

The antibodies and TCRs are additional embodiments of the immunotherapeutic use of the peptides according to the invention at hand.

The present invention further relates to a host cell comprising a nucleic acid according to the present invention or an expression vector as described before. The present invention further relates to the host cell according to the present invention that is an antigen presenting cell, and preferably is a dendritic cell.

The present invention further relates to a method for producing a peptide according to the present invention, said method comprising culturing the host cell according to the present invention, and isolating the peptide from said host cell or its culture medium.

The present invention further relates to said method according to the present invention, wherein the antigen is loaded onto class I or II MHC molecules expressed on the surface of a suitable antigen-presenting cell or artificial antigen-presenting cell by contacting a sufficient amount of the antigen with an antigen-presenting cell.

The present invention further relates to the method according to the present invention, wherein the antigen-presenting cell comprises an expression vector capable of expressing or expressing said peptide containing SEQ ID No. 1 to SEQ ID No.: 91, preferably containing SEQ ID No. 1 to SEQ ID No. 31, or a variant amino acid sequence.

The present invention further relates to activated T cells, produced by the method according to the present invention, wherein said T cell selectively recognizes a cell which expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as produced according to the present invention.

The present invention further relates to the use of any peptide as described, the nucleic acid according to the present invention, the expression vector according to the present invention, the cell according to the present invention, the activated T lymphocyte, the T cell receptor or the antibody or other peptide- and/or peptide-MHC-binding molecules according to the present invention as a medicament or in the manufacture of a medicament. Preferably, said medicament is active against cancer.

Preferably, said medicament is a cellular therapy, a vaccine or a protein based on a soluble TCR or antibody.

The present invention further relates to a use according to the present invention, wherein said cancer cells are head and neck squamous cell carcinoma, acute myelogenous leukemia, breast cancer, bile duct cancer, brain cancer, chronic lymphocytic leukemia, colorectal carcinoma, esophageal cancer, gallbladder cancer, gastric cancer, hepatocellular cancer, melanoma, non-Hodgkin lymphoma, non-small cell lung cancer, ovarian cancer, pancreatic cancer, prostate cancer, renal cell cancer, small cell lung cancer, urinary bladder cancer, uterine cancer, and preferably head and neck squamous cell carcinoma cells.

The present invention further relates to biomarkers based on the peptides according to the present invention, herein called "targets" that can be used in the diagnosis of cancer, preferably head and neck squamous cell carcinoma. The marker can be over-presentation of the peptide(s) themselves, or over-expression of the corresponding gene(s). The markers may also be used to predict the probability of success of a treatment, preferably an immunotherapy, and most preferred an immunotherapy targeting the same target that is identified by the biomarker. For example, an antibody or soluble TCR can be used to stain sections of the tumor to detect the presence of a peptide of interest in complex with MHC.

Optionally the antibody carries a further effector function such as an immune stimulating domain or toxin.

The present invention also relates to the use of the inventive novel targets in the context of cancer treatment.

ALOX12B is involved in terminal skin differentiation and epidermal barrier function (Furstenberger et al., 2007; Epp et al., 2007). ALOX12B is an immunosuppressive factor amplified in cancer (Rooney et al., 2015). Cisplatin induces and ATM phosphorylates (p)-DeltaNp63alpha. Subsequently, it up-regulates mi R-185-5p which down-regulates let7-5p resulting in the modulation of ALOX12B expression in squamous cell carcinoma (Ratovitski, 2013). ALOX12B is associated with breast cancer and lung cancer risk (Lee et al., 2009; Shen et al., 2009).

ANKRD17 mRNA levels are widely down-regulated in colorectal carcinomas and make this protein a potential marker for multi-target assay panels for colorectal cancer detection (Ioana et al., 2010). Through the phosphorylation of ANKRD17 by cyclin E/CdK2 the protein is involved in cell cycle regulation. Over-expression promotes S phase entry, whereas depletion of expression inhibits DNA replication, blocks cell cycle progression and up-regulates the expression of the tumor suppressors p53 and p21 (Deng et al., 2009).

ATP5G1 is enriched in the oxidative phosphorylation pathway in gastric cancer (Song et al., 2016). ATP5G1 expression is reduced in head and neck squamous cell carcinoma (Koc et al., 2015). Knock-out of augmenter of liver regeneration (ALR) results in accelerated development of steatohepatitis and hepatocellular carcinoma in mice. Further, ATP5G1 expression is reduced in ALR knock-down mice (Gandhi et al., 2015).

ATP5G2 is more methylated in high-grade bladder cancer tumors compared to low-intermediate-grade tumors (Kitchen et al., 2016). RIZ1 is a tumor suppressor whose depletion results in altered ATP5G2 expression (Xie et al., 2016b). ATP5G2 is highly expressed upon estrogen and progesterone treatment in endometrial Ishikawa cancer cell line (Tamm-Rosenstein et al., 2013). ATP5G2 promoter is methylated in primary renal cell carcinoma (Morris et al., 2011).

ATP5G3 is enriched in the oxidative phosphorylation pathway in gastric cancer (Song et al., 2016). ATP5G3 is up-regulated upon PPARalpha activation which is negatively correlated with tumor progression and which suppresses cell migration (Huang and Chang, 2016). ATP5G3 may be a radiation susceptibility gene (Tsuji et al., 2005).

BTBD11 encodes BTB domain containing 11 and is located on chromosome 12q23.3 (RefSeq, 2002). BTBD11 is differentially expressed in papillary thyroid cancer (Qu et al., 2016). BTBD11 is a TGF-beta target gene (Sawada et al., 2016). BTBD11 is mutated in gastric cancer (Leiserson et al., 2015; Leiserson et al., 2016).

Prognostic association of CD276 differs between smoking and non-smoking patients with lung adenocarcinoma. High CD276 expression is linked to smoking (Inamura et al., 2017). CD276 is hyper-methylated in prostate cancer (Wang et al., 2016b). CD276 is regulated by miR-124 which is down-regulated in osteosarcoma. TGF-beta1 up-regulates miR-155 through SMAD 3 and 4 signaling resulting in miR-143 attenuation by CEBPB inhibition which causes CD276 accumulation. CD276 is regulated by miR-187 which is down-regulated in colorectal cancer (Wang et al., 2016e; Trojandt et al., 2016; Zhou et al., 2016; Wang et al., 2016a). CD276 mediates abnormal lipid metabolism in lung cancer by affecting SREBP-1/FASN signaling. Soluble CD276 mediates pancreatic cancer invasion and metastasis through TLR4/NF-kappaB signaling (Xie et al., 2016a; Luo et al., 2016). CD276 is an immune checkpoint which may be a promising target in cancer therapy. It may be targeted during tumor growth to suppress anti-tumor immunity providing immune evasion for the emerging tumor (Leung and Suh, 2014; Swatler and Kozlowska, 2016; Janakiram et al., 2016). CD276 is expressed by most high-risk neuroblastomas, is over-expressed in tumor vasculature and plays an important role in tumor survival and invasiveness (Bottino et al., 2014). Knock-down of CD276 increases chemo sensitivity and decreases metastatic potential. Knock-down of CD276 results in increased apoptotic marker expression and STAT3 phosphorylation. Astragaloside IV treatment reduces cell growth and increases chemo sensitivity to cisplatin by inhibiting CD276 in non-small cell lung cancer cells (Nygren et al., 2011; He et al., 2016). CD276 is over-expressed in esophageal cancer, breast cancer, gallbladder cancer, prostate cancer, and ovarian cancer (Barach et al., 2011; Janakiram et al., 2012; Fauci et al., 2012; Chen et al., 2016; Liu et al., 2016). CD276 over-expression is correlated with poor survival, prognosis, and tumor grade. CD276 promotes cancer invasion and progression. However, CD276 may also have anti-tumor effects. High CD276 expression is an indicator of lymph node metastasis and advanced TNM stage in non-small cell lung cancer (Yi and Chen, 2009; Loos et al., 2010; Nygren et al., 2011; Fauci et al., 2012; Wang et al., 2014a; Ye et al., 2016; Benzon et al., 2016; Wu et al., 2016). CD276 down-regulates natural killer cells cytotoxicity supporting cancer immune evasion (Bottino et al., 2014).

CDH23 encodes cadherin related 23 which is a member of the cadherin superfamily, whose genes encode calcium dependent cell-cell adhesion glycoproteins. The encoded protein is thought to be involved in stereocilia organization and hair bundle formation. The gene is located in a region containing the human deafness loci DFNB12 and USH1D. Usher syndrome 1D and nonsyndromic autosomal recessive deafness DFNB12 are caused by allelic mutations of this cadherin-like gene. Up-regulation of this gene may also be associated with breast cancer (RefSeq, 2002). TMPRSS3 is a poor prognostic factor in breast cancer and can interact with CDH23 (Rui et al., 2015). CDH23 is up-regulated upon leptin treatment in ERalpha expressing breast cancer cells (Binai et al., 2013). CDH23 is up-regulated in breast cancer and may be involved in early stage metastasis (Apostolopoulou and Ligon, 2012). Loss of CDH23 can be observed in pancreatic cancer cell lines (Suzuki et al., 2008).

CDH3 is involved in oncogenic signaling and activates integrins, receptor tyrosine kinases, small molecule GTPases, EMT transcription factors, and other cadherin family members. CDH3 signaling induces invasion and metastasis (Albergaria et al., 2011; Paredes et al., 2012; Bryan, 2015; Vieira and Paredes, 2015). Oncogenic activation of CDH3 is involved in gastric carcinogenesis (Resende et al., 2011). CDH3 over-expression promotes breast cancer, bladder cancer, ovarian cancer, prostate cancer, endometrial cancer, skin cancer, gastric cancer, pancreas cancer, and colon cancer (Albergaria et al., 2011; Paredes et al., 2007; Bryan and Tselepis, 2010; Reyes et al., 2013; Vieira and Paredes, 2015). CDH3 is a basal epithelial marker expressed in basal-like breast cancer. BRCA1 carcinomas are characterized by the expression of basal markers like CDH3 and show a high-grade, highly proliferating, ER-negative, and HER3-negative phenotype (Honrado et al., 2006; Palacios et al., 2008; Rastelli et al., 2010; Dewar et al., 2011). CDH3 is a tumor suppressor in melanoma and oral squamous cell carcinoma (Haass et al., 2005; Vieira and Paredes, 2015). CDH3 may be used as EMT marker. There is a shift from E-cadherin to N-cadherin and CDH3 expression during tumor formation and progression (Piura et al., 2005; Bonitsis et al., 2006; Bryan and Tselepis, 2010; Ribeiro and Paredes, 2014). Competitive interaction between CDH3 and beta-catenin causes impaired intercellular interactions and metastases in gastric cancer (Moskvina and Mal'kov, 2010). CDH3 may be an early marker of cancer formation in colon cancer (Alrawi et al., 2006). Dys-regulation of CDH3 is a marker for poor prognosis and increased malignancy (Knudsen and Wheelock, 2005).

Over-expression of CLCA2 down-regulates beta-catenin and beta-catenin-activated genes (Ramena et al., 2016). CLCA2 strongly interacts with EVA1 which is also inducible by p53 and p63, frequently down-regulated in breast cancer causing EMT, and important for epithelial differentiation. Both proteins interact with E-cadherin (Ramena et al., 2016). There is an AML1-CLCA2 and a RUNX1-CLCA2 gene fusion product in adult acute myeloid leukemia (Giguere and Hebert, 2010; Jiang et al., 2013). CLCA2 is inducible by p73, p53, and p63 upon DNA damage and acts as an inhibitor of proliferation (Walia et al., 2009; Sasaki et al., 2012; Yu et al., 2013; Ramena et al., 2016). CLCA2 expression is elevated in circulating tumor cells from patients with lung adenocarcinoma and increased detection is associated with shortened patient survival (Hayes et al., 2006; Man et al., 2014). CLCA2 is higher expressed in squamous cell carcinoma of the lung compared to adenocarcinoma and is associated with histological tumor grade. CLCA2 expression may be used to detect non-small cell lung carcinoma and small cell lung carcinoma (Hayes et al., 2006; Shinmura et al., 2014). Knock-down of CLCA2 causes epithelial-to-mesenchymal transition, cancer cell migration, and invasion. Under normal condition, CLCA2 is thought to suppress migration and invasion through inhibition of the FAK signaling pathway. CLCA2 mediates lung metastasis in association with beta(4) integrin (Abdel-Ghany et al., 2001; Walia et al., 2012; Sasaki et al., 2012; Ramena et al., 2016). CLCA2 is down-regulated in breast cancer because of promotor hyper-methylation and is down-regulated in colorectal cancer. CLCA2 is differentially expressed in bladder carcinoma and during the metastatic transformation of melanoma. There are copy number losses for CLCA2 in mantle cell lymphoma (Gruber and Pauli, 1999; Bustin et al., 2001; Li et al., 2004; Balakrishnan et al., 2006; Riker et al., 2008; Walia et al., 2012; Matin et al., 2014; Ramena et al., 2016).

DSG1 is over-expressed in keratocystic odontogenic tumors and shows high rates of expression in oral intra-epithelial neoplasms (Aizawa et al., 2014; Heikinheimo et al., 2015). DSG1 expression is lost in acantholytic squamous cell carcinoma and down-regulated in chondrosarcoma, oral squamous cell carcinoma, and lung cancer (Xin et al., 2014; Saaber et al., 2015; Galoian et al., 2015; Jurcic et al., 2015). DSG1 expression is regulated by GRHL1 and GRHL1-negative mice treated with a standard chemical skin carcinogenesis protocol develop fewer papilloma but more squamous cell carcinomas (Mlacki et al., 2014). DSG1, which is a downstream target of Rhoda and GEF Bcr, is a keratinocyte differentiation marker (Dubash et al., 2013). KLK5 cleaves DSG1 which may be associated with metastases formation in oral squamous cell carcinoma. Reduced levels of DSG1 might be involved in pancreatic cancer invasion (Ramani et al., 2008; Jiang et al., 2011). Negative DSG1 staining is associated with improved anal cancer-specific survival and positive staining is associated with large tumor size and lymph node metastases. Loss of DSG1 is linked to bad prognosis in head and neck squamous cell carcinoma (Wong et al., 2008; Myklebust et al., 2012). Autoantibodies against DSG1 can be detected in paraneoplastic pemphigus (Seishima et al., 2004).

DSG3 expression in esophageal squamous cell carcinoma was shown to be highly correlated with histological grade and to have an impact on survival in esophageal squamous cell carcinoma, with negative DSG3 expression indicating worse survival. Thus, DSG3 may be involved in the progression of esophageal squamous cell carcinoma and may serve as a prognostic marker (Fang et al., 2014). In primary lung tumors, higher expression of DSG3 and DSG2 was shown to be correlated to the diagnosis of squamous cell lung carcinoma, while a lower expression of DSG3 was shown to be significantly linked to higher tumor grade. Thus, DSG3 may serve as a potential diagnostic marker for squamous cell lung carcinoma and a potential differentiation marker for lung cancer (Saaber et al., 2015). DSG3 was described as a negative prognostic biomarker in resected pancreatic ductal adenocarcinoma as high DSG3 expression was shown to be associated with poor overall survival and poor tumor-specific survival. Thus, DSG3 and its downstream signaling pathways may be possible therapeutic targets in DSG3-expressing pancreatic ductal adenocarcinoma (Ormanns et al., 2015).

Reduced expression of DSP is correlated with the tumor progression of several cancers including breast, lung and cervical cancer (Schmitt-Graeff et al., 2007; Davies et al., 1999; Yang et al., 2012b). Expression of DSP significantly suppresses cell proliferation, anchorage-independent growth, migration and invasion in lung cancer cells through inhibiting the Wnt/beta-catenin signaling pathway (Yang et al., 2012b).

DST may be related to breast cancer metastasis (Sun et al., 2006). Autoantibodies against DST can be found in lymphocytic leukemia and follicular lymphomas (Aisa et al., 2005; Taintor et al., 2007). DST is up-regulated in 5-8F cells (high tumorigenic and metastatic ability) in comparison to 6-10B cells (tumorigenic, but lacking metastatic ability) in nasopharyngeal carcinoma (Fang et al., 2005). DST is highly expressed in head and neck squamous cell carcinoma (Lin et al., 2004). There are autoantibodies against DST in paraneoplastic pemphigus which is associated with neoplasms (Yong and Tey, 2013; Wang et al., 2005; Preisz and Karpati, 2007; Zhu and Zhang, 2007). DST expression in prostate cancer is strongly inverse correlated with progression (Vanaja et al., 2003). Anti-DST autoantibodies are a promising marker for the diagnosis of melanoma (Shimbo et al., 2010). DST can be found in the urine of cachectic cancer patients (Skipworth et al., 2010). DST is differentially expressed in adenocarcinomas and squamous cell carcinomas of the lung (McDoniels-Silvers et al., 2002). DST is distinctly up-regulated with the onset of invasive cell growth (Herold-Mende et al., 2001).

EMC7 encodes ER membrane protein complex subunit 7 and is located on chromosome 15q14 (RefSeq, 2002). EMC7 may be a novel druggable target and diagnostic biomarker in cancer (Delgado et al., 2014). EMC7 is down-regulated in a pingyangmycin-resistant tongue squamous cell carcinoma cell line (Zheng et al., 2010).

ESRP2 encodes an epithelial cell-type-specific splicing regulator (RefSeq, 2002). ESRP2 inhibits cancer cell motility in different cancer types including lung and breast cancer cells. ESRP2 is down-regulated by TGF-beta in invasive fronts, leading to an increased expression of epithelial-mesenchymal transition-associated transcription factors (Gemmill et al., 2011; Horiguchi et al., 2012; Ishii et al., 2014).

A mutation in the PH-domain binding motif of F2RL1 is sufficient to decrease breast tumor growth (Bar-Shavit et al., 2016). F2RL1 is over-expressed in gastric cancer and is inversely correlated with overall survival of patients (Sedda et al., 2014). Tryptase is a mediator of angiogenesis released by mast cells which activates F2RL1 resulting in cancer cell proliferation, invasion, and metastasis (Marech et al., 2014; Ammendola et al., 2014). F2RL1 is affected by differentially expressed and mutated genes in cancer (D'Asti et al., 2014). F2RL1 is involved in cancer progression, invasion, and metastasis (Wojtukiewicz et al., 2015; Canto et al., 2012; Lima and Monteiro, 2013; Gieseler et al., 2013). F2RL1 is expressed in adenocarcinomas, melanomas, osteosarcomas, glioblastomas, meningiomas, leukemias, and squamous cell carcinomas (Elste and Petersen, 2010). F2RL1 regulates the expression of ALKS which is a TGF-beta type I receptor. F2RL1 activates MAP kinases (Oikonomopoulou et al., 2010; Witte et al., 2016). Up-regulation of tissue factor and integrins mediate F2RL1 signaling promoting metastasis (Kasthuri et al., 2009; Ruf et al., 2011; Kocaturk and Versteeg, 2012; Ruf, 2012; Kocaturk and Versteeg, 2013). Trypsin and PAR2 form an autocrine loop promoting proliferation, invasion, and metastasis. Trypsin stimulation may result in MAPK-ERK pathway activation through MMP- and PAR2-dependent activation of epidermal growth factor receptor (Soreide et al., 2006).

FAM160A1 encodes family with sequence similarity 160 member A1 and is located on chromosome 4q31.3 (RefSeq, 2002). FAM160A1 expression is altered upon DY131 binding to estrogen related receptor beta in prostate cancer (Lu et al., 2015b). There is a NFKB-FAM160A1 gene fusion product in prostate cancer (Teles, I et al., 2015). FAM160A1 is up-regulated in ovarian cancer compared to benign tumors (Li et al., 2012a). A deletion in FAM160A1 can be found in familial and early-onset breast cancer (Krepischi et al., 2012). FAM160A1 is down-regulated in colorectal cancer (Li et al., 2012b).

FANCE is associated with esophageal squamous cell carcinoma risk (Li et al., 2013). Rare down-regulation of FANCE can be observed in head and neck squamous cell carcinoma (Wreesmann et al., 2007). Chk1 mediates the phosphorylation of FANCE upon DNA crosslinking (Wang et al., 2007). Familial colorectal cancer shows a heterozygous genotype for FANCE. Fanconi anemia DNA damage repair may be linked to inherited pre-disposition to colorectal cancer. An indel mutation might be involved in inherited esophageal squamous cell carcinoma. A missense variant in FANCE was found in one family with breast cancer (Akbari et al., 2011; Seal et al., 2003; Esteban-Jurado et al., 2016). FANCE is involved in the regulation of cisplatin sensitivity (Taniguchi et al., 2003).

FAT1 was described as being significantly mutated in squamous-cell cancer of the head and neck, frequently mutated in cervical adenocarcinoma, bladder cancer, early T-cell precursor acute lymphoblastic leukemia, fludarabine refractoriness chronic lymphocytic leukemia, glioblastoma and colorectal cancer and mutated in esophageal squamous cell carcinoma (Gao et al., 2014; Neumann et al., 2013; Morris et al., 2013; Messina et al., 2014; Mountzios et al., 2014; Cazier et al., 2014; Chung et al., 2015). FAT1 was described as being repressed in oral cancer and preferentially down-regulated in invasive breast cancer (Katoh, 2012). FAT1 was described as being up-regulated in leukemia which is associated with a poor prognosis in preB-acute lymphoblastic leukemia (Katoh, 2012). FAT1 was shown to be up-regulated in pancreatic adenocarcinoma and hepatocellular carcinoma (Valletta et al., 2014; Wojtalewicz et al., 2014). FAT1 was described to suppress tumor growth via activation of Hippo signaling and to promote tumor migration via induction of actin polymerization (Katoh, 2012). FAT1 was shown to be a candidate cancer driver gene in cutaneous squamous cell carcinoma (Pickering et al., 2014). FAT1 was described as a tumor suppressor which is associated with Wnt signaling and tumorigenesis (Morris et al., 2013).

FAT3 was shown to be down-regulated in TAXOL resistant ovarian carcinoma cell lines upon silencing of androgen receptor, resulting in increased sensitization to Taxol in these cell lines. Thus, FAT3 may be a candidate gene associated with Taxol resistance (Sun et al., 2015b). FAT3 was shown to be mutated in esophageal squamous cell carcinoma, resulting in dysregulation of the Hippo signaling pathway (Gao et al., 2014). FAT3 was shown to be mutated recurrently in early T-cell precursor acute lymphoblastic leukemia (Neumann et al., 2013). FAT3 was described as a gene with signatures specific for meningothelial meningiomas, therefore being associated with tumorigenesis in this subtype of benign meningiomas (Fevre-Montange et al., 2009). FAT3 was described as a tumor suppressor which is repressed upon lung cancer development from dysplastic cells (Rohrbeck and Borlak, 2009).

FHAD1 is down-regulated upon NFE2 knock-down which is involved in oxidative stress response (Williams et al., 2016). CpG methylation of FHAD1 may be used as biomarker in metastatic-lethal prostate cancer (Zhao et al., 2017). FHAD1 is down-regulated in esophageal squamous cell carcinoma and may contribute to chemoresistance against cisplatin (Tsutsui et al., 2015). FHAD1 may be a tumor suppressor gene in breast cancer (Iorns et al., 2012).

G3BP1 encodes G3BP stress granule assembly factor 1 which is one of the DNA-unwinding enzymes which prefers partially unwound 3'-tailed substrates and can also unwind partial RNA/DNA and RNA/RNA duplexes in an ATP-dependent fashion (RefSeq, 2002). G3BP1 may be used as biomarker for drug response in HER2+ breast cancer (Chien et al., 2016). miR-193a-3p, which inhibits the progression and metastasis of lung cancer in vitro and in vivo, down-regulates G3BP1 (Deng et al., 2015). G3BP1 is a direct target of resveratrol. Depletion of G3BP1 reduces the resveratrol-induced p53 expression and apoptosis. G3BP1 is a negative regulator of p53 by interacting with USP10, a p53-specific deubiquitinase (Oi et al., 2015). G3BP1 is recruited by MYCNOS to the promotor region of MYCN to regulate its expression. G3BP1 negatively regulates PMP22 to increase proliferation in breast cancer (Winslow et al., 2013; Vadie et al., 2015). G3BP1 may be the target of a bi-functional peptide consisting of a cancer recognition peptide and a pro-apoptotic peptide (Meschenmoser et al., 2013). Late-stage oral squamous cell carcinomas are sensitive to G3BP1 knock-down causing increased apoptosis (Xu et al., 2013). G3BP1 is up-regulated in breast cancer, oral squamous cell carcinoma, colon cancer, pancreas cancer, hepatocellular carcinoma and gastric cancer and is correlated with poor patient prognosis, tumor size, vascular invasion, T classification, lymph node metastasis, TNM stage, and reduced overall survival (Lo et al., 2012; Winslow et al., 2013; Min et al., 2015; Dou et al., 2016). Y-box binding protein 1 binds to the 5'UTR of G3BP1 mRNA to regulate the availability of the G3BP1 stress granule nucleator for stress granule assembly. Down-regulation of either YB-1 or G3BP1 results in reduced stress granule formation and tumor invasion (Ward et al., 2011; Annibaldi et al., 2011; Somasekharan et al., 2015). G3BP1 controls the activity of the H+-ATPase and the translation of beta-F1-ATPase mRNA (Willers and Cuezva, 2011). G3BP1 co-localizes with promyelocytic leukemia nuclear bodies before and after ionizing radiation (Liu et al., 2010).

Epigallocatechin gallate, the major compound of green tea, suppresses lung tumorigenesis by binding to G3BP1. G3BP1 expression is affected by lovostatin (Klawitter et al., 2010; Shim et al., 2010). G3BP1 is involved in cancer cell growth, apoptosis, motility, migration, invasion, and metastasis by up-regulating Slug. Knock-down of G3BP1 decreases Slug expression and increases the epithelial marker E-cadherin. Up-regulation of G3BP1 in breast cancer activates epithelial-to-mesenchymal transition via the Smad signaling pathway. G3BP1 is involved in Ras and NF-kappaB signaling, ubiquitin proteasome pathway, and RNA processing (French et al., 2002; Zhang et al., 2015; Dou et al., 2016). Forced G3BP1 expression promotes cell migration in hepatocellular carcinoma (Dou et al., 2016).

GAR1 is able to activate p53 (Zhang et al., 2012). GAR1 is involved in the telomerase complex (Zhu et al., 2004; Rashid et al., 2006; Tomlinson et al., 2008; Pigullo et al., 2009; Low and Tergaonkar, 2013; Heidenreich et al., 2014). GAR1 is important for cell viability (Lubben et al., 1995).

ITGB4 is associated with prostate cancer, gastric cancer, breast cancer, oral squamous cell carcinoma and ovarian cancer and was shown to be up-regulated in pancreatic ductal adenocarcinoma (Chen et al., 2014; Xin et al., 2014; Zubor et al., 2015; Masugi et al., 2015; Gao et al., 2015; Kawakami et al., 2015). ITGB4 (also called CD104) tends to associate with the alpha 6 subunit and is likely to play a pivotal role in the biology of several invasive carcinoma such as esophageal squamous cell carcinoma, bladder and ovarian carcinoma (Kwon et al., 2013; Pereira et al., 2014; Chen et al., 2014). A single nucleotide polymorphism in ITGB4 seems to influence tumor aggressiveness and survival and may have prognostic value for breast cancer patients (Brendle et al., 2008).

KDM5B encodes the protein JARID1 B, a lysine-specific histone demethylase that is capable of repressing certain tumor suppressor genes by de-methylating lysine 4 of histone H3 (RefSeq, 2002). As epigenetic factor, KDM5B supports proliferation, migration and invasion of human OSCC, head and neck squamous cell carcinoma (HNSCC), breast cancer and lung cancer by suppressing p53 expression (Shen et al., 2015; Tang et al., 2015a; Zhao and Liu, 2015; Lin et al., 2015). Also, known as JARID1 B, KDM5B promotes metastasis an epithelial-mesenchymal transition in various tumor types via PTEN/AKT signaling (Tang et al., 2015a).

KLHL21 is up-regulated in hepatocellular carcinoma and may be used as bioclinical marker (Shi et al., 2016). KLHL21 is a negative regulator of IKKbeta. KLHL21 expression is down-regulated in macrophages upon pro-inflammatory stimuli. Over-expression of KLHL21 inhibits IKKbeta activation and IkappaBalpha degradation (Mei et al., 2016). KLHL21 is over-expressed by the aberrant gene fusion transcription factor ASPSCR1-TFE3 which is found in two distinct entities, alveolar soft part sarcoma and renal cell carcinoma (Kobos et al., 2013). KLHL21 may be involved in cancer (Martinez et al., 2010). KLHL21 is necessary for cytokinesis and regulates chromosomal passenger complex translocation from chromosomes to the spindle midzone in anaphase. It interacts with the Cullin3-based E3 ubiquitin ligase and directly binds to Aurora B causing its ubiquitination (Maerki et al., 2009). KLHL21 negatively regulates TNF alpha-activated NF-kappa B signaling via targeting IKK beta (Mei et al., 2016).

KLK6 encodes kallikein related peptidase 6 which is a member of the kallikrein subfamily of the peptidase S1 family of serine proteases. Growing evidence suggests that many kallikreins are implicated in carcinogenesis and some have potential as novel cancer and other disease biomarkers. Expression of this protease is regulated by steroid hormones and may be elevated in multiple human cancers and in serum from psoriasis patients. The encoded protease may participate in the cleavage of amyloid precursor protein and alpha-synuclein, thus implicating this protease in Alzheimer's and Parkinson's disease, respectively. This gene is located in a gene cluster on chromosome 19 (RefSeq, 2002). KLK6 is inducible by p53 and its expression increased autophagy and drug resistance in gastric cancer (Kim et al., 2016). Down-regulation of KLK6 is associated with increased GNA13 expression which is linked to invasiveness of benign breast tumors (Teo et al., 2016). KLK6 is able to up- and down-regulate several miRNAs, which may affect cell cycle, MYC, MAPK, and other signaling pathways (Sidiropoulos et al., 2016). KLK6 belongs to a set which is linked to panitumumab resistance in metastatic colorectal cancer (Barry et al., 2016). KLK6 is associated with the regulation of axonal growth following spinal injury, tumor cell metastasis, and alpha synuclein aggregate pathologies like Parkinson's disease (Xi et al., 2015). KLK6 is over-expressed in highly invasive PC3 prostate cancer and ovarian cancer and dys-regulated in cervical pre-cancer (Tamir et al., 2014; Hwang and Lindholm, 2015). KLK6 may be used as biomarker in a variety of entities including hepatocellular carcinoma, breast cancer, colon cancer, gastrointestinal cancer, and astrocytoma (Vakrakou et al., 2014; Yu et al., 2015b; Grin et al., 2015; Schrader et al., 2015; Drucker et al., 2015; Mange et al., 2016). KLK6 is associated with overall survival in advanced serous ovarian cancer and its expression might be linked to other clinical parameters (Kolin et al., 2014; Dorn et al., 2015; Yang et al., 2016a; Leung et al., 2016; Ahmed et al., 2016).

Knock-down of CD34, whose expression in head and neck squamous cell carcinoma is associated with cell cycle progression, up-regulates KRT1 expression (Ettl et al., 2016). KRT1 is down-regulated in HepG2 cells upon platycodin D treatment (Lu et al., 2015a). Immunohistochemical staining of a clear cell focus from a Bowens disease superficial invasive carcinoma is negative for KRT1 (Misago et al., 2016). miR-944 induces KRT1 expression by up-regulation of p53 and impairing of ERK signaling (Kim et al., 2015). KRT1 expression is up-regulated in early and late stage of squamous cell carcinoma (Tang et al., 2015b). Nuclear degradation down-regulates KRT1 expression (Naeem et al., 2015). KRT1 expression may be a marker for differentiation status. In combination with NMP-52 and AFP expression, it may be used to detect hepatocellular carcinoma (Attallah et al., 2015; Bruna et al., 2017). KRT1 is up-regulated upon docosahexaenoic acid treatment, which is known to reduce breast cancer invasion (Blanckaert et al., 2015). Proliferating basophilic cells from onychocytic carcinoma failed to express KRT1 (Wang et al., 2015a). Up-regulation of KRT1 is indirectly associated with Notch1 receptor stimulation (Vliet-Gregg et al., 2015). S100A7 down-regulates KRT1 (Li et al., 2015). Expression of KRT1 is associated with p21 and hsp70 expression in oral squamous cell carcinoma. KRT1 absence is correlated with the absence of Klf4, which is a transcription factor that suppresses cell proliferation and promotes differentiation (Paparella et al., 2015; Frohwitter et al., 2016).

KRT13 encodes keratin 13 which is a member of the keratin gene family. Vitamin D alters KRT13 expression (Narayanan, 2006). Immunostaining for CK13 is positive in the epidermoid component of mucoepidermoid carcinoma and is negative in canalicular adenoma and oncolytic carcinoma arising in submandibular gland (Muramatsu et al., 2003; Matsuzaka et al., 2004; do Prado et al., 2007). Aberrant expression of alpha 6 beta 4 integrin up-regulates KRT13, an early event in the development of squamous cancer of the skin (Tennenbaum et al., 1996). KRT13 may be used as biomarker for cervical intraepithelial neoplasia. Loss of KRT13 is a marker for tumor grade and stage in transitional urothelial cell carcinoma. KRT13 expression is a marker for skin cancer progression (Slaga et al., 1995; Southgate et al., 1999; Duggan, 2002; Baak et al., 2006). KRT13 expression is down-regulated in oral cancer stem cells and oral squamous cell carcinoma (Morgan and Su, 1994; Sinha et al., 2013).

KRT14 was highly expressed in various squamous cell carcinomas such as esophageal, lung, larynx, uterine cervical as well as in adenomatoid odontogenic tumor. However, it was absent in small cell carcinoma of the urinary bladder and weak in lung adenocarcinoma, gastric adenocarcinoma, colorectal adenocarcinoma, hepatocellular carcinoma, pancreatic ductal adenocarcinoma, breast infiltrating dutal adenocarcinoma, thyroid papillary carcinoma and uterine endometrioid adenocarcinoma (Xue et al., 2010; Terada, 2012; Vasca et al., 2014; Hammam et al., 2014; Shruthi et al., 2014). In bladder cancer, KRT14 expression was strongly associated with poor survival (Volkmer et al., 2012).

Long-time exposure of MCF-7 breast cancer cells to ethanol up-regulates KRT15 which is a malignancy-related gene (Gelfand et al., 2017). Basal cell carcinomas with invasive growth show a negative expression of KRT15 (Ziari et al., 2015). KRT15 may be used to discriminate spiradenomas and cylindromas (Sellheyer, 2015). KRT15 is sequentially up-regulated in bladder carcinogenesis (Chuang et al., 2014). SIRT2, which is down-regulated in skin cancer, inhibits KRT15 expression, which is an epithelial stem cell marker (Wang et al., 2014b). KRT15 is a hair follicle stem cell marker (Bongiovanni et al., 2014; Koba et al., 2015; Narisawa et al., 2015). KRT15 is an undifferentiated basal cell marker more strongly expressed in malignant compared to benign ocular surface squamous neoplasia (Nagata et al., 2014). Spheroid-selected epidermal squamous cell carcinomas have an enriched KRT15 expression (Adhikary et al., 2013). KRT15 is up-regulated in urothelial carcinoma (Tai et al., 2013). KRT15 staining of actinic keratoses associated with head and neck tumors is positive in 7% of the cases and in 36% in adenoid cystic carcinoma. Staining is higher in desmoplastic trichoepithelioma compared to morphea form basal cell carcinoma and microcystic adnexal carcinoma (Sabeti et al., 2013; Evangelista and North, 2015; North et al., 2015; Solus et al., 2016). KRT15 up-regulation affects overall survival in non-small cell lung cancer and may be used as marker for differential diagnosis of NSCLC (Gomez-Morales et al., 2013; Boyero et al., 2013). KRT15 is regulated by p53 and ER (Lion et al., 2013).

Over-expression of KRT16 was found in basal-like breast cancer cell lines as well as in carcinoma in situ. Others did not find significant difference in immunohistochemical expression of KRT16 between non-recurrent ameloblastomas and recurrent ameloblastomas (Joosse et al., 2012; Ida-Yonemochi et al., 2012; Safadi et al., 2016). In addition, in silico analyses showed correlation between KRT16 expression and shorter relapse-free survival in metastatic breast cancer (Joosse et al., 2012).

KRT5 was shown to be up-regulated in breast cancers of young women (Johnson et al., 2015). KRT5 was shown to be associated with inferior disease-free survival in breast cancer in young women and with unfavorable clinical outcome in premenopausal patients with hormone receptor-positive breast cancer (Johnson et al., 2015; Sato et al., 2014). KRT5 was shown to be regulated by the tumor suppressor BRCA1 in the breast cancer cell lines HCC1937 and T47D (Gorski et al., 2010). KRT5 was shown to be de-regulated in malignant pleural mesothelioma (Melaiu et al., 2015). KRT5 was described as a diagnostic mesothelial marker for malignant mesothelioma (Arif and Husain, 2015). KRT5 was shown to be correlated with the progression of endometrial cancer (Zhao et al., 2013). KRT5 was shown to be mutated and down-regulated in invasive tumor areas in a patient with verrucous carcinoma (Schumann et al., 2012). KRT5 was shown to be part of a four-protein panel which was differentially expressed in colorectal cancer biopsies compared to normal tissue samples (Yang et al., 2012a). KRT5 and three other proteins of the four-protein panel were described as novel markers and potential targets for treatment for colorectal cancer (Yang et al., 2012a). KRT5 was described as being associated with basal cell carcinoma (Depianto et al., 2010). KRT5 was described as a candidate to identify urothelial carcinoma stem cells (Hatina and Schulz, 2012).

KRT6A was described as part of a seven-gene signature that could be used as a prognostic model to predict distant recurrence-free survival in patients with triple negative breast cancer who received adjuvant chemotherapy following surgery (Park et al., 2015b). KRT6A was shown to be up-regulated in horn cancer in Bos indicus and in gastric cancer (El-Rifai et al., 2002; Koringa et al., 2013). KRT6A was shown to be down-regulated in two cases of vulvar sarcomas with morphologic and immunohistochemical characteristics of extraskeletal myxoid chondrosarcoma (Dotlic et al., 2014). KRT6A expression was shown to be altered in oral squamous cell carcinoma (Chanthammachat et al., 2013). KRT6A was shown to be associated with negative regulation of proto-oncogene Src kinase activity and the migratory potential of skin keratinocytes during wound repair. This may be important in related contexts such as cancer (Rotty and Coulombe, 2012). KRT6A was shown to mark mammary bi-potential progenitor cells that can give rise to a unique mammary tumor model resembling human normal-like breast cancer (Bu et al., 2011). KRT6A was described as an important part of a 25-gene transcriptional network signature which can be used to distinguish adenocarcinomas and squamous cell carcinomas of the lung (Chang et al., 2011).

KRT6B was shown to be a candidate for down-regulated genes in the esophageal cancer cell line KYSE170 (Kan et al., 2006). KRT6B was shown to be up-regulated in renal cell carcinoma, sporadic keratocystic odontogenic tumors and in horn cancer in Bos indicus (Koringa et al., 2013; Hu et al., 2015; Heikinheimo et al., 2007). KRT6B loss-of-function was shown to inhibit the expression of notch1 and induce renal cell carcinoma cell death in vitro. Thus, KRT6B interaction with notch1 was described to contribute to progression of renal cell carcinoma (Hu et al., 2015). KRT6B was described as a basal-like breast cancer-associated cytokeratin whose expression was diminished upon decreased expression of basal-like tumor-associated GABRP in the cell lines HCC1187 and HCC70 (Sizemore et al., 2014). Selective inhibition of ERK1/2 was also shown to result in decreased expression of basal-like cytokeratins such as KRT6B and decreased migration in basal-like breast cancer (Sizemore et al., 2014). Thus, the GABRP-ERK1/2-cytokeratin axis is involved in maintaining the migratory phenotype of basal-like breast cancer (Sizemore et al., 2014). KRT6B was shown to be associated with negative regulation of proto-oncogene Src kinase activity and the migratory potential of skin keratinocytes during wound repair. This may be important in related contexts such as cancer (Rotty and Coulombe, 2012). KRT6B was described as an important part of a 25-gene transcriptional network signature which can be used to distinguish adenocarcinomas and squamous cell carcinomas of the lung (Chang et al., 2011). KRT6B was shown to be differentially expressed during benzo (a) pyrene induced tumorigenesis of human immortalized oral epithelial cells (Li et al., 2008).

KRT6C was described as an important part of a 25-gene transcriptional network signature which can be used to distinguish adenocarcinomas and squamous cell carcinomas of the lung (Chang et al., 2011).

KRT75 encodes keratin 75 which is a member of the type II keratin family clustered on the long arm of chromosome 12. The encoded protein plays an essential role in hair and nail formation. Variations in this gene have been associated with the hair disorders pseudofolliculitis barbae (PFB) and loose anagen hair syndrome (LAHS) (RefSeq, 2002). KRT75 is down-regulated in an in vivo passaged and re-derived prostatic cell line compared to the parental cell line (Sivanathan et al., 2014). KRT75 is expressed in onychomatricoma which may suggest a differentiation toward the nail bed and the nail isthmus (Perrin et al., 2011). KRT75 is down-regulated in 21T breast cells (Xu et al., 2010). KRT75 expression can be changed by proteasome inhibitors and dexamethasone (Kinyamu et al., 2008).

Inhibition of LAP3 was shown to result in suppressed invasion in the ovarian cancer cell line ES-2 through down-regulation of fascin and MMP-2/9. Thus, LAP3 may act as a potential anti-metastasis therapeutic target (Wang et al., 2015b). High expression of LAP3 was shown to be correlated with grade of malignancy and poor prognosis of glioma patients (He et al., 2015). LAP3 was shown to promote glioma progression by regulating cell growth, migration and invasion and thus might be a new prognostic factor (He et al., 2015). Frameshift mutations in genes involved in amino acid metabolism including LAP3 were detected in microsatellite instability-high gastric and colorectal cancer (Oh et al., 2014). LAP3 was shown to be up-regulated in hepatocellular carcinoma, esophageal squamous cell carcinoma and prostate cancer (Zhang et al., 2014a; Tian et al., 2014; Lexander et al., 2005). LAP3 was shown to promote hepatocellular carcinoma cells proliferation by regulating G1/S checkpoint in cell cycle and advanced cells migration (Tian et al., 2014). Expression of LAP3 was further shown to be correlated with prognosis and malignant development of hepatocellular carcinoma (Tian et al., 2014). Silencing of LAP3 in the esophageal squamous cell carcinoma cell line ECA109 was shown to reduce cell proliferation and colony formation while LAP3 knock-down resulted in cell cycle arrest (Zhang et al., 2014a). Over-expression of LAP3 in the esophageal squamous cell carcinoma cell line TE1 was shown to favor cell proliferation and invasiveness (Zhang et al., 2014a). Thus, LAP3 was shown to play a role in the malignant development of esophageal squamous cell carcinoma (Zhang et al., 2014a).

High levels of LGALS7 are associated with an aggressive phenotype in breast cancer with increased cancer invasiveness, growth, and metastasis (Grosset et al., 2016). LGALS7 is differentially expressed in the serum of colorectal cancer patients whereas immunohistochemical staining of CRC tumors is negative for LGALS7 (Lim et al., 2016). LGALS7 is down-regulated in prostate cancer, cervical cancer, and vulvar squamous cell carcinoma and is correlated with advanced clinical stage, poor differentiation, and regional lymph node metastasis. Re-expression leads to increased apoptosis. Increased promotor methylation is associated with advanced clinical stage, poor differentiation, and regional lymph node metastasis in VSCC (Labrie et al., 2015; Jiang et al., 2015; Higareda-Almaraz et al., 2016). Cytoplasmic expressed LGALS7 inhibits p53 and increases chemoresistance in breast cancer (Grosset et al., 2014). LGALS7 is not expressed in normal ovarian tissue and expressed in epithelial ovarian cancer. Expression is more frequent in high grade and metastatic tumors and correlates with overall survival. LGALS7 expression is induced by mutant p53 (Kim et al., 2013; Labrie et al., 2014). LGALS7 may be used as biomarker for metastatic cutaneous melanoma. It is also correlated with clinical parameters in head and neck squamous and basal cell carcinoma (Timar et al., 2010; Cada et al., 2009). LGALS7 is related to breast cancer incidence (Tang et al., 2008). LGALS7 expression can be induced by p53 and is able to act pro-apoptotic (Ueda et al., 2004).

LGALS7B potentiates the HER2 positive breast cancer aggressiveness (Grosset et al., 2016). LGALS7B regulates molecules involved in apoptosis, tissue morphogenesis, metabolism, transport, chemokine activity, and immune response (Higareda-Almaraz et al., 2016). LGALS7B is down-regulated in cervical cancer. High LGALS7B expression in association with low Gal-1 expression is linked to better prognosis (Higareda-Almaraz et al., 2016). LGALS7B is hyper-methylated in vulvar squamous cell carcinoma (Jiang et al., 2015). Re-expression of LGALS7B in prostate cancer enhances chemosensitivity to etoposide and cisplatin (Labrie et al., 2015). LGALS7B is down-regulated in vulvar squamous cell carcinoma, prostate cancer, and colorectal cancer. Down-regulation of LGALS7B is associated with advanced clinical stage, poor tumor differentiation, and regional lymph node metastasis (Labrie et al., 2015; Lim et al., 2016; Jiang et al., 2015). Cytosolic LGALS7B inhibits dox-induced PARP-1 cleavage resulting in suppressed p53 activation and decreased p21 and CDKN1A expression in breast cancer (Grosset et al., 2014). LGALS7B up-regulates apoptosis and inhibits IL-2 and IFN-gamma expression (Yamaguchi et al., 2013). LGALS7B is over-expressed in ovarian cancer and is associated with greater age, high mortality, increased tumor volume, and poor survival (Kim et al., 2013; Labrie et al., 2014). Immunohistochemical staining of LGALS7B may be used to distinguish salivary gland tumor types (Remmelink et al., 2011). LGALS7B is down-regulated in head and neck basal cell carcinoma. In head and neck squamous cell carcinoma, LGALS7B shows different expression patterns and different expression levels are correlated with keratinization and differentiation (Cada et al., 2009).

MALL may be used to categorize lung cancer subtypes (Watanabe et al., 2010). MALL may be a metastasis suppressor gene in prostate cancer (Yi et al., 2009). MALL mRNA and protein expression is reduced in colon cancer patients and is associated with vessin invasion, disease recurrence, and metastasis or death. Loss of MALL is associated with decreased overall survival and disease-free survival. Over-expression of MALL suppresses cell proliferation and inhibits migration in cell lines (Fan et al., 2011; Kim et al., 2008a; Wang et al., 2016c). MALL can be found on prostasomes secreted by a prostate cancer cell line where it interacts with caveolin-1 (Llorente et al., 2004). MALL is down-regulated in non-small cell lung cancer and cervical squamous cell cancer. It is differentially expressed in glioma cells (Ai et al., 2003; Hatta et al., 2004; Kettunen et al., 2004).

MCM4 expression is associated with up-regulated carbonic anhydrase IX, a transmembrane glycoprotein which is correlated with decreased survival and cancer progression in several entities including esophageal cancer (Huber et al., 2015). Has-miR-615-3p may be involved in nasopharyngeal carcinoma by regulating MCM4 (Chen et al., 2015). MCM4 might play a role in the development of bladder cancer (Zekri et al., 2015). A gain-of-function mutant of p53 increases the expression of MCM4 in breast cancer (Polotskaia et al., 2015). There is a mutation of MCM4 in human skin cancer which shows reduced DNA helicase activity (Ishimi and Irie, 2015). MCM4 over-expression alone is only weakly associated with shorter survival in breast cancer. Over-expression of all six parts of the MCM complex is strongly associated with shorter survival (Kwok et al., 2015). MCM4 is differentially expressed in lung adenocarcinoma and laryngeal squamous cell carcinoma (Lian et al., 2013; Zhang et al., 2014b). MCM4 is significantly over-expressed in cervical cancer (Das et al., 2013; Das et al., 2015). MCM4 may be used as biomarker for colorectal cancer (Fijneman et al., 2012).

Antizyme inhibitor inhibits ubiquitin-independent degradation of ODC1 resulting in accelerated polyamine formation which triggers the development of gastric cancer, breast cancer, hepatocellular carcinoma, and esophageal squamous cell carcinoma (Qiu et al., 2016). Piroxicam inhibits ODC1-dependent polyamine production involved in non-melanoma skin carcinogenesis (Campione et al., 2015). ODC1 regulates putrescine which is important for cell division regulation, differentiation, maturation, and apoptosis (Ramani et al., 2014; Zdrojewicz and Lachowski, 2014). ODC1 is a Myc and MYCN target gene and high ODC1 expression is associated with reduced event-free survival in neuroblastoma (Funakoshi-Tago, 2012; Saletta et al., 2014). Blocking ODC1 may be used for chemoprophylaxis in colorectal cancer (Zhou et al., 2012).

PARP9 (also known as ARTD9) encodes poly(ADP-ribose) polymerase family member 9 and is located on chromosome 3q21.1 (RefSeq, 2002). DTX3L forms complexes with ARTD8 and PARP9 promoting proliferation, chemoresistance, and survival of metastatic prostate cancer cells by inhibiting the tumor suppressor IRF1 (Bachmann et al., 2014). PARP9 inhibits IFN-gamma-STAT1-IRF1-p53 signaling in diffuse large B cell lymphoma and activates the expression of the proto-oncogenes IRF2 and BCL-6. This results in proliferation, survival, and chemoresistance in DLBCL (Camicia et al., 2013). PARP9 expression is IFN-gamma-inducible (Juszczynski et al., 2006). PARP9 may be a drug target in diffuse large B cell lymphoma. PARP9 is an oncogenic survival factor in high-risk, chemoresistant DLBCL (Bachmann et al., 2014; Aguiar et al., 2005; Camicia et al., 2015).

PKP1 was shown to be down-regulated in prostate cancer and esophageal adenocarcinoma (Kaz et al., 2012; Yang et al., 2015). Knock-down of PKP1 in the non-neoplastic, prostatic BPH-1 cell line led to reduced apoptosis and differential expression of genes such as the prostate cancer-associated SPOCK1 gene (Yang et al., 2015). Collectively, altered expression of PKP1 and SPOCK1 appears to be frequent and critical event in prostate cancer and PKP1 is suggested to have a tumor-suppressive function (Yang et al., 2015). Reduced expression of PKP1 was shown to be associated with significantly shorter time to onset of distant metastasis in oral cavity squamous cell carcinoma (Harris et al., 2015). PKP1 loss through promoter methylation was described to be associated with the progression of Barrett's esophagus to esophageal adenocarcinoma (Kaz et al., 2012). PKP1 was shown to be up-regulated in non-small cell lung cancer and may be a good marker to distinguish squamous-cell carcinomas samples (Sanchez-Palencia et al., 2011). PKP1 was shown to be up-regulated in the well-differentiated liposarcoma cell line GOT3 (Persson et al., 2008). Decreased PKP1 expression was described to promote increased motility in head and neck squamous cell carcinoma cells (Sobolik-Delmaire et al., 2007). PKP1 loss was shown to be associated with cervical carcinogenesis (Schmitt-Graeff et al., 2007). PKP1 was shown to be associated with local recurrences or metastases as well as poor survival in patients with squamous cell carcinoma of the oropharynx (Papagerakis et al., 2003).

PLEC is over-expressed in colorectal adenocarcinoma, head and neck squamous cell carcinoma and pancreatic cancer (Lee et al., 2004; Katada et al., 2012; Bausch et al., 2011).

Periplakin is decreased in T24CDDPR bladder cancer cells (Taoka et al., 2015). PPL staining is lower in bladder cancer compared to healthy tissue. Loss of PPL is linked to pathological stage and survival (Matsumoto et al., 2014). PPL is correlated with epithelial-like tumor cells (Kohn et al., 2014). EVPL, periplakin, and involucrin-negative mice show a skin cancer-resistant phenotype (Cipolat et al., 2014; Natsuga et al., 2015; Natsuga et al., 2016). PPL is highly expressed in triple-negative breast cancer (Choi et al., 2013). Periplakin is down-regulated in esophageal squamous cell carcinoma because of hyper-methylation. PPL knock-down in ESCC is associated with reduced cellular movement and attachment (Otsubo et al., 2015; Tonoike et al., 2011). Paraneoplastic pemphigus shows autoantibodies against PPL (Yong and Tey, 2013; Li et al., 2009; Probst et al., 2009; Zimmermann et al., 2010).

PRKDC is a frequently mutated gene in endometriosis-associated ovarian cancer and breast cancer (Er et al., 2016; Wheler et al., 2015). PRKDC is up-regulated in cancerous tissues compared with normal tissues in colorectal carcinoma. Patients with high PRKDC expression show poorer overall survival (Sun et al., 2016).

PRNP encodes a membrane glycosylphosphatidylinositol-anchored glycoprotein that tends to aggregate into rod-like structures and contains a highly unstable region of five tandem octapeptide repeats. Mutations in the repeat region as well as elsewhere in this gene have been associated with various prion diseases. An overlapping open reading frame has been found for this gene that encodes a smaller, structurally unrelated protein, AltPrp (RefSeq, 2002). Although its physiological role is not completely defined, PRNP is involved in self-renewal, pluripotency gene expression, proliferation and differentiation of neural stem cells. PNRP plays a role in in human tumors including glioblastoma, breast cancer, prostate cancer and colorectal cancer (Yang et al., 2016b; Corsaro et al., 2016). In colorectal cancer PRNP has been shown to contribute to epithelial-mesenchymal transition (Du et al., 2013). Over-expression of PNRP combined with MGr1-Ag/37LRP is predictive of poor prognosis in gastric cancer (Zhou et al., 2014). PNRP expression is related to redox state of cells and may participate in antioxidative defense. Silencing PNRP has been shown to sensitize cancer cells to anticancer drugs in breast cancer and colon cancer (Sauer et al., 1999; Meslin et al., 2007; Park et al., 2015a; Yun et al., 2016).

PROM2 is specifically up-regulated in lung adenocarcinoma (Bao et al., 2016). PROM2 is expressed in elastofibromas and human prostate cancer. PROM2 is higher expressed in low aggressive prostate cancer and lower expressed in high aggressive prostate cancer (Yamazaki, 2007; Zhang et al., 2002). PROM2 is down-regulated in colon cancer (Deng et al., 2013). PROM2 expression may be used to differ between chromophobe renal cell carcinoma and oncocytoma (Rohan et al., 2006).

RIPK4 was shown to be down-regulated in squamous cell carcinoma of the skin (Poligone et al., 2015). RIPK4 is associated with migration and invasion in the tongue squamous cell carcinoma cell line Tca-8113, survival of diffuse large B-cell lymphoma and overall as well as disease-free survival, progression and poor prognosis in cervical squamous cell carcinoma (Wang et al., 2014c; Liu et al., 2015; Kim et al., 2008b). RIPK4 is associated with familial pancreatic cancer (Lucito et al., 2007). RIPK4 may be a potential diagnostic and independent prognostic biomarker for cervical squamous cell carcinoma and a biomarker for tongue cancer prognosis and treatment (Wang et al., 2014c; Liu et al., 2015).

RNASE7 expression is gradually decreased in cutaneous cancer (Scola et al., 2012). RNASE7 expression is affected by several leukemogenic protein tyrosine kinases (Pierce et al., 2008).

RPL8 expression can be affected by MYC-induced nuclear antigen and nucleolar protein 66 (Chowdhury et al., 2014). RPL8 may be involved in osteosarcoma (Sun et al., 2015a; Yang and Zhang, 2013). RPL8 is regulated by NO-66 which is activated by MYC (Ge et al., 2012). A mutation in RPL8 is linked to Diamond-Blackfan anemia (Gazda et al., 2012). RPL8 expression may be linked to chemotherapy response (Salas et al., 2009). RPL8 is dysregulated in hepatocellular carcinoma (Liu et al., 2007). MHCII-dependent expression of RPL8 can be found in melanoma (Swoboda et al., 2007).

SERPINB5 is both a valuable molecular marker for the diagnosis and a predictor for the prognosis of many cancer types including breast, lung, head and neck, oral and prostate cancer (Marioni et al., 2009; Lonardo et al., 2010; Sager et al., 1996; Sheng, 2004). SERPINB5 acts as an endogenous regulator of HDAC1 activity and interacts with the p53 tumor suppressor pathway (Maass et al., 2000; Kaplun et al., 2012).

SLC25A3 is de-regulated in chronic myeloid leukemia (Oehler et al., 2009). Depletion of SLC25A3 abolishes stress-induced mitochondrial targeting of BAX (Buttner et al., 2011).

SLC6A11 expression is reduced in rats with paclitaxel-induced neuropathic pain, a phenomenon which can be observed in carcinoma patients treated with paclitaxel (Yadav et al., 2015). ALA and its methyl ester MAL are pro-drugs used in photodynamic therapy of skin cancer. Their uptake is mediated by SLC6A11 (Novak et al., 2011; Schulten et al., 2012; Baglo et al., 2013). Chronic treatment of glioma cells with sodium valproate reduces SLC6A11 mRNA expression (Gao et al., 2003).

SLC6A15 is hyper-methylated and thereby down-regulated in colorectal cancer and may be a candidate biomarker for a stool-based assay (Kim et al., 2011; Mitchell et al., 2014).

SLC7A1 is constitutively expressed in acute myeloid leukemia blasts. These blasts show deficiencies in arginine-recycling pathway enzymes resulting in arginine accumulation and cell proliferation and survival (Mussai et al., 2015). SLC7A1 is over-expressed in colorectal cancer resulting in arginine accumulation and cell growth. Over-expression of chromosome 13 genes is quite common in CRC (Camps et al., 2013; Lu et al., 2013). SLC7A1 may be used as a marker for macrophage differentiation. Its expression increases during the induction of THP1 monocyte differentiation (Barilli et al., 2011). The growth of the MCF-7 breast cancer cell line is dependent on L-arginine. It expresses SLC7A1 and SLC7A1 knock-down results in reduced arginine uptake, decreased cell viability, and increased apoptosis (Abdelmagid et al., 2011). SLC7A1 expression strongly correlates with the expression of Heme Oxygenase-1 which is expressed in many cancers, promoting tumor growth and survival (Tauber et al., 2010). SLC7A1 is a direct target of the liver-specific miR-122 which is down-regulated in hepatocellular carcinoma. miR-122 down-regulation results in SLC7A1 up-regulation and increased intracellular arginine levels. This pathway is also an important mechanism for colorectal cancer-derived liver metastases (Kedde and Agami, 2008; lino et al., 2013; Kishikawa et al., 2015). Activation of protein kinase C results in SLC7A1 internalization. Stress leads to differential expression of SLC7A1 (Kakuda et al., 1998; Rotmann et al., 2006).

Loss of SUDS3 leads to altered cell morphology and increased cell migration (Smith et al., 2012). SUDS3 is involved in thymocyte differentiation (Lee et al., 2012). SUDS3 may have anti-tumor effects (Ramakrishna et al., 2012). USP17 de-ubiquitinates SUDS3 resulting in altered SUDS3-associated HDAC activities in cancer (Ramakrishna et al., 2011). SUDS3 is involved in mitosis (Pondugula et al., 2009). SUDS3 is expressed in breast cancer (Silveira et al., 2009). SUDS3 controls chromosome segregation and can interact with p53 (David et al., 2006).

TENM2 might be involved in age at menarche. Early AAM is associated with type 2 diabetes mellitus, breast and ovarian cancer, and cardiovascular diseases and late AAM is associated with low bone mineral density and psychological disorders (Yermachenko and Dvornyk, 2016). There is a DOCK2-TENM2 gene fusion transcript in lung cancer patients living in highly polluted regions (Yu et al., 2015a). TENM2 is expressed in the majority of malignant mesothelioma cells (Ziegler et al., 2012). TENM2 may be down-regulated in esophageal squamous cell carcinoma (Kan et al., 2006).

Focal deletion of TGMS in stage II colon cancer may be a driver for this entity (Brosens et al., 2010). A TGMS mutation occurring in non-small cell lung cancer shows no difference between smokers and never-smokers (Yongjun Zhang et al., 2013; Broderick et al., 2009; Rafnar et al., 2011; Choi et al., 2016). Loss of TGFBR3 in prostate cancer also down-regulates TGMS (Sharifi et al., 2007).

XIRP1 is mutated in the metastases of basal-like breast cancer (Hoadley et al., 2016). XIRP1 promotor motif gene signature is enriched in triple negative breast cancer compared to ER+ HER2− breast cancer (Willis et al., 2015). XIRP1 is up-regulated upon vitamin C treatment which also decreases cell growth in cancer (Marshall et al., 2012; Nagappan et al., 2013). XIRP1 is mutated in head and neck squamous cell carcinoma and may be a tumor suppressor gene (Lee et al., 2010). XIRP1 is an oxidative stress associated gene (Baluchamy et al., 2010).

ZBED6 is a transcriptional repressor of IGF2 which is over-expressed in colorectal cancer and promotes cell proliferation. Knock-down of ZBED6 affects the cell cycle and leads to enhanced cell growth in RKO cell line and reduced cell growth in HCT116 cells. ZBED6 is a transcriptional repressor of several genes involved in Wnt, Hippo, TGF-beta, EGFR, and PI3K signaling which are all involved in colorectal carcinogenesis (Markljung et al., 2009; Andersson, 2009; Andersson et al., 2010; Huang et al., 2014; Jiang et al., 2014; Clark et al., 2015; Akhtar et al., 2015).

DETAILED DESCRIPTION OF THE INVENTION

Stimulation of an immune response is dependent upon the presence of antigens recognized as foreign by the host immune system. The discovery of the existence of tumor associated antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognizing and destroying tumor cells. The isolation of T-cells from tumor-infiltrating cell populations or from peripheral blood suggests that such cells play an important role in natural immune defense against cancer. CD8-positive T-cells in particular, which recognize class I molecules of the major histocompatibility complex (MHC)-bearing peptides of usually 8 to 10 amino acid residues derived from proteins or defect ribosomal products (DRIPS) located in the cytosol, play an important role in this response. The MHC-molecules of the human are also designated as human leukocyte-antigens (HLA).

The term "T-cell response" means the specific proliferation and activation of effector functions induced by a peptide in vitro or in vivo. For MHC class I restricted cytotoxic T cells, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation.

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, 12, 13 or 14 or longer, and in case of MHC class II peptides (elongated variants of the peptides of the invention) they can be as long as 15, 16, 17, 18, 19 or 20 or more amino acids in length.

Furthermore, the term "peptide" shall include salts of a series of amino acid residues, connected one to the other typically by peptide bonds between the alpha-amino and carbonyl groups of the adjacent amino acids. Preferably, the salts are pharmaceutical acceptable salts of the peptides, such as, for example, the chloride or acetate (trifluoroacetate) salts. It has to be noted that the salts of the peptides according to the present invention differ substantially from the peptides in their state(s) in vivo, as the peptides are not salts in vivo.

The term "peptide" shall also include "oligopeptide". The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 15 amino acids in length.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response. In another aspect, the immunogen can be the peptide, the complex of the peptide with MHC, oligopeptide, and/or protein that is used to raise specific antibodies or TCRs against it.

A class I T cell "epitope" requires a short peptide that is bound to a class I MHC receptor, forming a ternary complex (MHC class I alpha chain, beta-2-microglobulin, and peptide) that can be recognized by a T cell bearing a matching T-cell receptor binding to the MHC/peptide complex with appropriate affinity. Peptides binding to MHC class I molecules are typically 8-14 amino acids in length, and most typically 9 amino acids in length.

In humans, there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-B*07 are examples of different MHC class I alleles that can be expressed from these loci.

TABLE 5

Expression frequencies F of HLA-A*02 and HLA-A*24 and the most frequent HLA-DR serotypes.

| Allele | Population | Calculated phenotype from allele frequency |
|---|---|---|
| A*02 | Caucasian (North America) | 49.1% |
| A*02 | African American (North America) | 34.1% |
| A*02 | Asian American (North America) | 43.2% |
| A*02 | Latin American (North American) | 48.3% |
| DR1 | Caucasian (North America) | 19.4% |
| DR2 | Caucasian (North America) | 28.2% |
| DR3 | Caucasian (North America) | 20.6% |
| DR4 | Caucasian (North America) | 30.7% |
| DR5 | Caucasian (North America) | 23.3% |
| DR6 | Caucasian (North America) | 26.7% |
| DR7 | Caucasian (North America) | 24.8% |
| DR8 | Caucasian (North America) | 5.7% |
| DR9 | Caucasian (North America) | 2.1% |
| DR1 | African (North) American | 13.20% |
| DR2 | African (North) American | 29.80% |
| DR3 | African (North) American | 24.80% |
| DR4 | African (North) American | 11.10% |
| DR5 | African (North) American | 31.10% |
| DR6 | African (North) American | 33.70% |
| DR7 | African (North) American | 19.20% |
| DR8 | African (North) American | 12.10% |
| DR9 | African (North) American | 5.80% |
| DR1 | Asian (North) American | 6.80% |
| DR2 | Asian (North) American | 33.80% |
| DR3 | Asian (North) American | 9.20% |
| DR4 | Asian (North) American | 28.60% |
| DR5 | Asian (North) American | 30.00% |
| DR6 | Asian (North) American | 25.10% |
| DR7 | Asian (North) American | 13.40% |
| DR8 | Asian (North) American | 12.70% |
| DR9 | Asian (North) American | 18.60% |
| DR1 | Latin (North) American | 15.30% |
| DR2 | Latin (North) American | 21.20% |
| DR3 | Latin (North) American | 15.20% |
| DR4 | Latin (North) American | 36.80% |
| DR5 | Latin (North) American | 20.00% |
| DR6 | Latin (North) American | 31.10% |
| DR7 | Latin (North) American | 20.20% |
| DR8 | Latin (North) American | 18.60% |
| DR9 | Latin (North) American | 2.10% |
| A*24 | Philippines | 65% |
| A*24 | Russia Nenets | 61% |
| A*24:02 | Japan | 59% |
| A*24 | Malaysia | 58% |
| A*24:02 | Philippines | 54% |
| A*24 | India | 47% |
| A*24 | South Korea | 40% |
| A*24 | Sri Lanka | 37% |
| A*24 | China | 32% |
| A*24:02 | India | 29% |
| A*24 | Australia West | 22% |
| A*24 | USA | 22% |
| A*24 | Russia Samara | 20% |

TABLE 5-continued

Expression frequencies F of HLA-A*02 and HLA-A*24 and the most frequent HLA-DR serotypes.

| Allele | Population | Calculated phenotype from allele frequency |
|---|---|---|
| A*24 | South America | 20% |
| A*24 | Europe | 18% |

Frequencies are deduced from haplotype frequencies Gf within the American population adapted from Mori et al. (Mori et al., 1997) employing the Hardy-Weinberg formula F = 1 − (1 − Gf)².
Combinations of A*02 or A*24 with certain HLA-DR alleles might be enriched or less frequent than expected from their single frequencies due to linkage disequilibrium.
For details refer to Chanock et al. (Chanock et al., 2004).

The peptides of the invention, preferably when included into a vaccine of the invention as described herein bind to A*02. A vaccine may also include pan-binding MHC class II peptides. Therefore, the vaccine of the invention can be used to treat cancer in patients that are A*02 positive, whereas no selection for MHC class II allotypes is necessary due to the pan-binding nature of these peptides.

If A*02 peptides of the invention are combined with peptides binding to another allele, for example A*24, a higher percentage of any patient population can be treated compared with addressing either MHC class I allele alone. While in most populations less than 50% of patients could be addressed by either allele alone, a vaccine comprising HLA-A*24 and HLA-A*02 epitopes can treat at least 60% of patients in any relevant population. Specifically, the following percentages of patients will be positive for at least one of these alleles in various regions: USA 61%, Western Europe 62%, China 75%, South Korea 77%, Japan 86% (calculated from www.allelefrequencies.net).

In a preferred embodiment, the term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

As used herein the term "a nucleotide coding for (or encoding) a peptide" refers to a nucleotide sequence coding for the peptide including artificial (man-made) start and stop codons compatible for the biological system the sequence is to be expressed by, for example, a dendritic cell or another cell system useful for the production of TCRs.

As used herein, reference to a nucleic acid sequence includes both single stranded and double stranded nucleic acid. Thus, for example for DNA, the specific sequence, unless the context indicates otherwise, refers to the single strand DNA of such sequence, the duplex of such sequence with its complement (double stranded DNA) and the complement of such sequence.

The term "coding region" refers to that portion of a gene which either naturally or normally codes for the expression product of that gene in its natural genomic environment, i.e., the region coding in vivo for the native expression product of the gene.

The coding region can be derived from a non-mutated ("normal"), mutated or altered gene, or can even be derived from a DNA sequence, or gene, wholly synthesized in the laboratory using methods well known to those of skill in the art of DNA synthesis.

The term "expression product" means the polypeptide or protein that is the natural translation product of the gene and any nucleic acid sequence coding equivalents resulting from genetic code degeneracy and thus coding for the same amino acid(s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'-OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment, if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly encompassed.

The nucleic acids and polypeptide expression products disclosed according to the present invention, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form. The term "active fragment" means a fragment, usually of a peptide, polypeptide or nucleic acid sequence, that generates an immune response (i.e., has immunogenic activity) when administered, alone or optionally with a suitable adjuvant or in a vector, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion", "segment" and "fragment", when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, these terms refer to the products produced by treatment of said polynucleotides with any of the endonucleases.

In accordance with the present invention, the term "percent identity" or "percent identical", when referring to a sequence, means that a sequence is compared to a claimed or described sequence after alignment of the sequence to be compared (the "Compared Sequence") with the described or claimed sequence (the "Reference Sequence"). The percent identity is then determined according to the following formula:

percent identity=$100[1-(C/R)]$ wherein C is the number of differences between the Reference Sequence and the Compared Sequence over the length of alignment between the Reference Sequence and the Compared Sequence, wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference and (iiii) the alignment has to start at position 1 of the aligned sequences;

and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the herein above calculated percent identity is less than the specified percent identity.

As mentioned above, the present invention thus provides a peptide comprising a sequence that is selected from the group of consisting of SEQ ID NO: 1 to SEQ ID NO: 91 or a variant thereof which is 88% homologous to SEQ ID NO: 1 to SEQ ID NO: 91, or a variant thereof that will induce T cells cross-reacting with said peptide. The peptides of the invention have the ability to bind to a molecule of the human major histocompatibility complex (MHC) Class-I or elongated versions of said peptides to class II.

In the present invention, the term "homologous" refers to the degree of identity (see percent identity above) between sequences of two amino acid sequences, i.e. peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other tools are provided by public databases.

A person skilled in the art will be able to assess, whether T cells induced by a variant of a specific peptide will be able to cross-react with the peptide itself (Appay et al., 2006; Colombetti et al., 2006; Fong et al., 2001; Zaremba et al., 1997).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence in consisting of SEQ ID NO: 1 to SEQ ID NO: 91. For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated T cells.

These T cells can subsequently cross-react with cells and kill cells that express a polypeptide that contains the natural amino acid sequence of the cognate peptide as defined in the aspects of the invention. As can be derived from the scientific literature and databases (Rammensee et al., 1999; Godkin et al., 1997), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus, one skilled in the art would be able to modify the amino acid sequences set forth in SEQ ID NO: 1 to SEQ ID NO 91, by maintaining the known anchor residues, and would be able to determine whether such variants maintain the ability to bind MHC class I or II molecules. The variants of the present invention retain the ability to bind to the TCR of activated T cells, which can subsequently cross-react with and kill cells that express a polypeptide containing the natural amino acid sequence of the cognate peptide as defined in the aspects of the invention.

The original (unmodified) peptides as disclosed herein can be modified by the substitution of one or more residues at different, possibly selective, sites within the peptide chain, if not otherwise stated. Preferably those substitutions are located at the end of the amino acid chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly nonconservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, non-standard amino acids (i.e., other than the common naturally occurring proteinogenic amino acids) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would be simultaneously substituted.

A peptide consisting essentially of the amino acid sequence as indicated herein can have one or two non-anchor amino acids (see below regarding the anchor motif) exchanged without that the ability to bind to a molecule of the human major histocompatibility complex (MHC) Class-I or —II is substantially changed or is negatively affected, when compared to the non-modified peptide. In another embodiment, in a peptide consisting essentially of the amino acid sequence as indicated herein, one or two amino acids can be exchanged with their conservative exchange partners (see herein below) without that the ability to bind to a molecule of the human major histocompatibility complex (MHC) Class-I or —II is substantially changed, or is negatively affected, when compared to the non-modified peptide.

The amino acid residues that do not substantially contribute to interactions with the T-cell receptor can be modified by replacement with other amino acid whose incorporation does not substantially affect T-cell reactivity and does not eliminate binding to the relevant MHC. Thus, apart from the proviso given, the peptide of the invention may be any peptide (by which term the inventors include oligopeptide or polypeptide), which includes the amino acid sequences or a portion or variant thereof as given.

TABLE 6

Variants and motif of the peptides according to SEQ ID NO: 4, 6, and 10

| | | Position | | | | | | | | |
|---|---|---|---|---|---|---|---|---|---|---|
| | 1 | 2 | 3 | 4 | 5 | 6 | 7 | 8 | 9 | 10 |
| SEQ ID NO. 4 Variants | I | L | D | I | N | D | N | P | P | V |
| | | | | | | | | | | I |
| | | | | | | | | | | L |
| | | | | | | | | | | A |
| | | M | | | | | | | | |
| | | M | | | | | | | | I |
| | | M | | | | | | | | L |
| | | M | | | | | | | | A |
| | | A | | | | | | | | |
| | | A | | | | | | | | I |
| | | A | | | | | | | | L |
| | | A | | | | | | | | A |
| | | V | | | | | | | | |
| | | V | | | | | | | | I |
| | | V | | | | | | | | L |
| | | V | | | | | | | | A |
| | | T | | | | | | | | |
| | | T | | | | | | | | I |
| | | T | | | | | | | | L |
| | | T | | | | | | | | A |
| | | Q | | | | | | | | |
| | | Q | | | | | | | | I |
| | | Q | | | | | | | | L |
| | | Q | | | | | | | | A |
| SEQ ID NO. 6 Variants | A | L | Y | D | A | E | L | S | Q | M |
| | | | | | | | | | | V |
| | | | | | | | | | | I |
| | | | | | | | | | | L |
| | | | | | | | | | | A |
| | | M | | | | | | | | V |
| | | M | | | | | | | | I |
| | | M | | | | | | | | L |
| | | M | | | | | | | | A |
| | | A | | | | | | | | V |
| | | A | | | | | | | | I |
| | | A | | | | | | | | L |
| | | A | | | | | | | | A |
| | | V | | | | | | | | V |
| | | V | | | | | | | | I |
| | | V | | | | | | | | L |
| | | V | | | | | | | | A |
| | | T | | | | | | | | V |
| | | T | | | | | | | | I |
| | | T | | | | | | | | L |
| | | T | | | | | | | | A |
| | | Q | | | | | | | | V |
| | | Q | | | | | | | | I |
| | | Q | | | | | | | | L |
| | | Q | | | | | | | | A |
| SEQ ID NO. 10 Variants | T | L | W | P | A | T | P | P | K | A |
| | | | | | | | | | | V |
| | | | | | | | | | | I |
| | | | | | | | | | | L |
| | | M | | | | | | | | V |
| | | M | | | | | | | | I |
| | | M | | | | | | | | L |
| | | M | | | | | | | | |
| | | A | | | | | | | | V |
| | | A | | | | | | | | I |
| | | A | | | | | | | | L |
| | | A | | | | | | | | |
| | | V | | | | | | | | V |
| | | V | | | | | | | | I |
| | | V | | | | | | | | L |
| | | V | | | | | | | | |
| | | T | | | | | | | | V |
| | | T | | | | | | | | I |
| | | T | | | | | | | | L |
| | | T | | | | | | | | |
| | | Q | | | | | | | | V |

TABLE 6-continued

Variants and motif of the peptides according to
SEQ ID NO: 4, 6, and 10

| Position | | | | | | | | | |
|---|---|---|---|---|---|---|---|---|---|
| 1 | 2 | 3 | 4 | 5 | 6 | 7 | 8 | 9 | 10 |
|  | Q |  |  |  |  |  |  |  | I |
|  | Q |  |  |  |  |  |  |  | L |
|  | Q |  |  |  |  |  |  |  |  |

Longer (elongated) peptides may also be suitable. It is possible that MHC class I epitopes, although usually between 8 and 11 amino acids long, are generated by peptide processing from longer peptides or proteins that include the actual epitope. It is preferred that the residues that flank the actual epitope are residues that do not substantially affect proteolytic cleavage necessary to expose the actual epitope during processing.

The peptides of the invention can be elongated by up to four amino acids, that is 1, 2, 3 or 4 amino acids can be added to either end in any combination between 4:0 and 0:4. Combinations of the elongations according to the invention can be found in Table 7.

TABLE 7

Combinations of the elongations (extensions) of peptides of the invention

| C-terminus | N-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

| N-terminus | C-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

The amino acids for the elongation/extension can be the peptides of the original sequence of the protein or any other amino acid(s). The elongation can be used to enhance the stability or solubility of the peptides.

Thus, the epitopes of the present invention may be identical to naturally occurring tumor-associated or tumor-specific epitopes or may include epitopes that differ by no more than four residues from the reference peptide, as long as they have substantially identical antigenic activity.

In an alternative embodiment, the peptide is elongated on either or both sides by more than 4 amino acids, preferably to a total length of up to 30 amino acids. This may lead to MHC class II binding peptides. Binding to MHC class II can be tested by methods known in the art.

Accordingly, the present invention provides peptides and variants of MHC class I epitopes, wherein the peptide or variant has an overall length of from 8 and 100, from 9 and 100, from 10 and 100, from 11 and 100, from 12 and 100, preferably from 8 and 30, and from 9 and 30, from 10 and 30, from 11 and 30, from 12 and 30, most preferred from 8 and 14, from 9 and 14, from 10 and 14, from 11 and 14, from 12 and 14. The present invention further provides peptides and variants of MHC class I epitopes, wherein the peptide or variant has an overall length of namely 8, 9, 10, 11, 12, 13, or 14 amino acids, in case of the elongated class II binding peptides the length can also be 15, 16, 17, 18, 19, 20, 21 or 22 amino acids.

Of course, the peptide or variant according to the present invention will have the ability to bind to a molecule of the human major histocompatibility complex (MHC) class I or II. Binding of a peptide or a variant to a MHC complex may be tested by methods known in the art.

Preferably, when the T cells specific for a peptide according to the present invention are tested against the substituted peptides, the peptide concentration at which the substituted peptides achieve half the maximal increase in lysis relative to background is no more than about 1 mM, preferably no more than about 1 µM, more preferably no more than about 1 nM, and still more preferably no more than about 100 µM, and most preferably no more than about 10 µM. It is also preferred that the substituted peptide be recognized by T cells from more than one individual, at least two, and more preferably three individuals.

In a particularly preferred embodiment of the invention the peptide consists or consists essentially of an amino acid sequence according to SEQ ID NO: 1 to SEQ ID NO: 91.

"Consisting essentially of" shall mean that a peptide according to the present invention, in addition to the sequence according to any of SEQ ID NO: 1 to SEQ ID NO 91 or a variant thereof contains additional N- and/or C-terminally located stretches of amino acids that are not necessarily forming part of the peptide that functions as an epitope for MHC molecules epitope.

Nevertheless, these stretches can be important to provide an efficient introduction of the peptide according to the present invention into the cells. In one embodiment of the present invention, the peptide is part of a fusion protein which comprises, for example, the 80 N-terminal amino acids of the HLA-DR antigen-associated invariant chain (p33, in the following "Ii") as derived from the NCBI, GenBank GENBANK Accession number X00497. In other fusions, the peptides of the present invention can be fused to an antibody as described herein, or a functional part thereof, in particular into a sequence of an antibody, so as to be specifically targeted by said antibody, or, for example, to or into an antibody that is specific for dendritic cells as described herein.

In addition, the peptide or variant may be modified further to improve stability and/or binding to MHC molecules in order to elicit a stronger immune response. Methods for such an optimization of a peptide sequence are well known in the art and include, for example, the introduction of reverse peptide bonds or non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) (Meziere et al., 1997), incorporated herein by reference. This approach involves making pseudopeptides containing changes involving the backbone, and not the orientation of side chains. Meziere et al. (Meziere et al., 1997) show that for MHC binding and T helper cell responses, these pseudopeptides are useful. Retro-inverse peptides, which contain NH—CO bonds instead of CO—NH peptide bonds, are much more resistant to proteolysis.

A non-peptide bond is, for example, —CH$_2$—NH, —CH$_2$S—, —CH$_2$CH$_2$—, —CH=CH—, —COCH$_2$—, —CH(OH)CH$_2$—, and —CH$_2$SO—. U.S. Pat. No. 4,897,445 provides a method for the solid phase synthesis of non-peptide bonds (—CH$_2$—NH) in polypeptide chains which involves polypeptides synthesized by standard procedures and the non-peptide bond synthesized by reacting an amino aldehyde and an amino acid in the presence of NaCNBH$_3$.

Peptides comprising the sequences described above may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenylmethoxycarbonyl group may be placed at the peptides' amino termini. Additionally, the hydrophobic group, t-butyloxycarbonyl, or an amido group may be added to the peptides' carboxy termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well-known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2004 (Lundblad, 2004), which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley and Sons NY 1995-2000) (Coligan et al., 1995) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of companies such as Sigma-Aldrich (www.sigma-aldrich.com) provide information on specific reagents.

Selective reduction of disulfide bonds in proteins is also common. Disulfide bonds can be formed and oxidized during the heat treatment of biopharmaceuticals. Woodward's Reagent K may be used to modify specific glutamic acid residues. N-(3-(dimethylamino)propyl)-N'-ethylcarbodiimide can be used to form intra-molecular crosslinks between a lysine residue and a glutamic acid residue. For example, diethylpyrocarbonate is a reagent for the modification of histidyl residues in proteins. Histidine can also be modified using 4-hydroxy-2-nonenal. The reaction of lysine residues and other α-amino groups is, for example, useful in binding of peptides to surfaces or the cross-linking of proteins/peptides. Lysine is the site of attachment of poly (ethylene)glycol and the major site of modification in the glycosylation of proteins. Methionine residues in proteins can be modified with e.g. iodoacetamide, bromoethylamine, and chloramine T.

Tetranitromethane and N-acetylimidazole can be used for the modification of tyrosyl residues. Cross-linking via the formation of dityrosine can be accomplished with hydrogen peroxide/copper ions.

Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole).

Successful modification of therapeutic proteins and peptides with PEG is often associated with an extension of circulatory half-life while cross-linking of proteins with glutaraldehyde, polyethylene glycol diacrylate and formaldehyde is used for the preparation of hydrogels. Chemical modification of allergens for immunotherapy is often achieved by carbamylation with potassium cyanate.

Another embodiment of the present invention relates to a non-naturally occurring peptide wherein said peptide consists or consists essentially of an amino acid sequence according to SEQ ID No: 1 to SEQ ID No: 156 and has been synthetically produced (e.g. synthesized) as a pharmaceutically acceptable salt. Methods to synthetically produce peptides are well known in the art. The salts of the peptides according to the present invention differ substantially from the peptides in their state(s) in vivo, as the peptides as generated in vivo are no salts. The non-natural salt form of the peptide mediates the solubility of the peptide, in particular in the context of pharmaceutical compositions comprising the peptides, e.g. the peptide vaccines as disclosed herein. A sufficient and at least substantial solubility of the peptide(s) is required in order to efficiently provide the peptides to the subject to be treated. Preferably, the salts are pharmaceutically acceptable salts of the peptides. These salts according to the invention include alkaline and earth alkaline salts such as salts of the Hofmeister series comprising as anions PO$_4^{3-}$, SO$_4^{2-}$, CH$_3$COO$^-$, Cl$^-$, Br$^-$, NO$_3^-$, ClO$_4^-$, I$^-$, SCN$^-$ and as cations NH$_4^+$, Rb$^+$, K$^+$, Na$^+$, Cs$^+$, Li$^+$, Zn$^{2+}$, Mg$^{2+}$, Ca$^{2+}$, Mn$^{2+}$, Cu$^{2+}$ and Ba$^{2+}$. Particularly salts are selected from (NH$_4$)$_3$PO$_4$, (NH$_4$)$_2$HPO$_4$, (NH$_4$)H$_2$PO$_4$, (NH$_4$)$_2$SO$_4$, NH$_4$CH$_3$COO, NH$_4$Cl, NH$_4$Br, NH$_4$NO$_3$, NH$_4$ClO$_4$, NH$_4$I, NH$_4$SCN, Rb$_3$PO$_4$, Rb$_2$HPO$_4$, RbH$_2$PO$_4$, Rb$_2$SO$_4$, Rb$_4$CH$_3$COO, Rb$_4$Cl, Rb$_4$Br, Rb$_4$NO$_3$, Rb$_4$ClO$_4$, Rb$_4$I, Rb$_4$SCN, K$_3$PO$_4$, K$_2$HPO$_4$, KH$_2$PO$_4$, K$_2$SO$_4$, KCH$_3$COO, KCl, KBr, KNO$_3$, KClO$_4$, KI, KSCN, Na$_3$PO$_4$, Na$_2$HPO$_4$, NaH$_2$PO$_4$, Na$_2$SO$_4$, NaCH$_3$COO, NaCl, NaBr, NaNO$_3$, NaClO$_4$, NaI, NaSCN, ZnCl$_2$ Cs$_3$PO$_4$, Cs$_2$HPO$_4$, CsH$_2$PO$_4$, Cs$_2$SO$_4$, CsCH$_3$COO, CsCl, CsBr, CsNO$_3$, CsClO$_4$, CsI, CsSCN, Li$_3$PO$_4$, Li$_2$HPO$_4$, LiH$_2$PO$_4$, Li$_2$SO$_4$, LiCH$_3$COO, LiCl, LiBr, LiNO$_3$, LiClO$_4$, LiI, LiSCN, Cu$_2$SO$_4$, Mg$_3$(PO$_4$)$_2$, Mg$_2$HPO$_4$, Mg(H$_2$PO$_4$)$_2$, Mg$_2$SO$_4$, Mg(CH$_3$COO)$_2$, MgCl$_2$, MgBr$_2$, Mg(NO$_3$)$_2$, Mg(ClO$_4$)$_2$, MgI$_2$, Mg(SCN)$_2$, MnCl$_2$, Ca$_3$(PO$_4$), Ca$_2$HPO$_4$, Ca(H$_2$PO$_4$)$_2$, CaSO$_4$, Ca(CH$_3$COO)$_2$, CaCl$_2$, CaBr$_2$, Ca(NO$_3$)$_2$, Ca(ClO$_4$)$_2$, CaI$_2$, Ca(SCN)$_2$, Ba$_3$(PO$_4$)$_2$, Ba$_2$HPO$_4$, Ba(H$_2$PO$_4$)$_2$, BaSO$_4$, Ba(CH$_3$COO)$_2$, BaCl$_2$, BaBr$_2$, Ba(NO$_3$)$_2$, Ba(ClO$_4$)$_2$, BaIe, and Ba(SCN)$_2$.

Particularly preferred are NH acetate, MgCl$_2$, KH$_2$PO$_4$, Na$_2$SO$_4$, KCl, NaCl, and CaCl$_2$, such as, for example, the chloride or acetate (trifluoroacetate) salts.

A peptide or variant, wherein the peptide is modified or includes non-peptide bonds is a preferred embodiment of the invention. Generally, peptides and variants (at least those containing peptide linkages between amino acid residues) may be synthesized by the Fmoc-polyamide mode of solid-phase peptide synthesis as disclosed by Lukas et al. (Lukas et al., 1981) and by references as cited therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoracetic acid containing a 50% scavenger mix. Scavengers commonly used include ethanedithiol, phenol, anisole and water, the exact choice depending on the constituent amino acids of the peptide being synthesized. Also a combination of solid phase and solution phase methodologies for the synthesis of peptides is possible (see, for example, (Bruckdorfer et al., 2004), and the references as cited therein).

Trifluoracetic acid is removed by evaporation in vacuo, with subsequent trituration with diethyl ether affording the crude peptide. Any scavengers present are removed by a simple extraction procedure which on lyophilization of the aqueous phase affords the crude peptide free of scavengers. Reagents for peptide synthesis are generally available from e.g. Calbiochem-Novabiochem (Nottingham, UK).

Purification may be performed by any one, or a combination of, techniques such as re-crystallization, size exclusion chromatography, ion-exchange chromatography, hydrophobic interaction chromatography and (usually) reverse-phase high performance liquid chromatography using e.g. acetonitrile/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

In order to select over-presented peptides, a presentation profile is calculated showing the median sample presentation as well as replicate variation. The profile juxtaposes samples of the tumor entity of interest to a baseline of normal tissue samples. Each of these profiles can then be consolidated into an over-presentation score by calculating the p-value of a Linear Mixed-Effects Model (Pinheiro et al., 2015) adjusting for multiple testing by False Discovery Rate (Benjamini and Hochberg, 1995) (cf. Example 1, FIGS. 1A-1Q).

For the identification and relative quantitation of HLA ligands by mass spectrometry, HLA molecules from shock-frozen tissue samples were purified and HLA-associated peptides were isolated. The isolated peptides were separated and sequences were identified by online nano-electrospray-ionization (nanoESI) liquid chromatography-mass spectrometry (LC-MS) experiments. The resulting peptide sequences were verified by comparison of the fragmentation pattern of natural tumor-associated peptides (TUMAPs) recorded from head and neck squamous cell carcinoma samples (N=17 A*02-positive samples) with the fragmentation patterns of corresponding synthetic reference peptides of identical sequences. Since the peptides were directly identified as ligands of HLA molecules of primary tumors, these results provide direct evidence for the natural processing and presentation of the identified peptides on primary cancer tissue obtained from 14 head and neck squamous cell carcinoma patients.

The discovery pipeline XPRESIDENT® v2.1 (see, for example, US 2013-0096016, which is hereby incorporated by reference in its entirety) allows the identification and selection of relevant over-presented peptide vaccine candidates based on direct relative quantitation of HLA-restricted peptide levels on cancer tissues in comparison to several different non-cancerous tissues and organs. This was achieved by the development of label-free differential quantitation using the acquired LC-MS data processed by a proprietary data analysis pipeline, combining algorithms for sequence identification, spectral clustering, ion counting, retention time alignment, charge state deconvolution and normalization.

Presentation levels including error estimates for each peptide and sample were established. Peptides exclusively presented on tumor tissue and peptides over-presented in tumor versus non-cancerous tissues and organs have been identified.

HLA-peptide complexes from head and neck squamous cell carcinoma tissue samples were purified and HLA-associated peptides were isolated and analyzed by LC-MS (see examples). All TUMAPs contained in the present application were identified with this approach on primary head and neck squamous cell carcinoma samples confirming their presentation on primary head and neck squamous cell carcinoma.

TUMAPs identified on multiple head and neck squamous cell carcinoma and normal tissues were quantified using ion-counting of label-free LC-MS data. The method assumes that LC-MS signal areas of a peptide correlate with its abundance in the sample. All quantitative signals of a peptide in various LC-MS experiments were normalized based on central tendency, averaged per sample and merged into a bar plot, called presentation profile. The presentation profile consolidates different analysis methods like protein database search, spectral clustering, charge state deconvolution (decharging) and retention time alignment and normalization.

Besides over-presentation of the peptide, mRNA expression of the underlying gene was tested. mRNA data were obtained via RNASeq analyses of normal tissues and cancer tissues (cf. Example 2, FIGS. 2A-2C). An additional source of normal tissue data was a database of publicly available RNA expression data from around 3000 normal tissue samples (Lonsdale, 2013). Peptides which are derived from proteins whose coding mRNA is highly expressed in cancer tissue, but very low or absent in vital normal tissues, were preferably included in the present invention.

The present invention provides peptides that are useful in treating cancers/tumors, preferably head and neck squamous cell carcinoma that over- or exclusively present the peptides of the invention. These peptides were shown by mass spectrometry to be naturally presented by HLA molecules on primary human head and neck squamous cell carcinoma samples.

Many of the source gene/proteins (also designated "full-length proteins" or "underlying proteins") from which the peptides are derived were shown to be highly over-expressed in cancer compared with normal tissues—"normal tissues" in relation to this invention shall mean either healthy [insert normal tissue of major indication] cells or other normal tissue cells, demonstrating a high degree of tumor association of the source genes (see Example 2). Moreover, the peptides themselves are strongly over-presented on tumor tissue—"tumor tissue" in relation to this invention shall mean a sample from a patient suffering from head and neck squamous cell carcinoma, but not on normal tissues (see Example 1).

HLA-bound peptides can be recognized by the immune system, specifically T lymphocytes. T cells can destroy the cells presenting the recognized HLA/peptide complex, e.g. head and neck squamous cell carcinoma cells presenting the derived peptides.

The peptides of the present invention have been shown to be capable of stimulating T cell responses and/or are over-presented and thus can be used for the production of antibodies and/or TCRs, such as soluble TCRs, according to the present invention (see Example 3, Example 4). Furthermore, the peptides when complexed with the respective MHC can be used for the production of antibodies and/or TCRs, in particular sTCRs, according to the present invention, as well. Respective methods are well known to the person of skill, and can be found in the respective literature as well. Thus, the peptides of the present invention are useful for generating an immune response in a patient by which tumor cells can be destroyed. An immune response in a patient can be induced by direct administration of the described peptides or suitable precursor substances (e.g. elongated peptides, proteins, or nucleic acids encoding these peptides) to the patient, ideally in combination with an agent enhancing the immunogenicity (i.e. an adjuvant). The immune response originating from such a therapeutic vaccination can be expected to be highly specific against tumor cells because the target peptides of the present invention are not presented on normal tissues in comparable copy numbers, preventing the risk of undesired autoimmune reactions against normal cells in the patient.

The present description further relates to T-cell receptors (TCRs) comprising an alpha chain and a beta chain ("alpha/beta TCRs"). Also provided are inventive peptides capable of binding to TCRs and antibodies when presented by an MHC molecule. The present description also relates to nucleic acids, vectors and host cells for expressing TCRs and peptides of the present description; and methods of using the same.

The term "T-cell receptor" (abbreviated TCR) refers to a heterodimeric molecule comprising an alpha polypeptide chain (alpha chain) and a beta polypeptide chain (beta chain), wherein the heterodimeric receptor is capable of binding to a peptide antigen presented by an HLA molecule. The term also includes so-called gamma/delta TCRs.

In one embodiment, the description provides a method of producing a TCR as described herein, the method comprising culturing a host cell capable of expressing the TCR under conditions suitable to promote expression of the TCR.

The description in another aspect relates to methods according to the description, wherein the antigen is loaded onto class I or II MHC molecules expressed on the surface of a suitable antigen-presenting cell or artificial antigen-presenting cell by contacting a sufficient amount of the antigen with an antigen-presenting cell or the antigen is loaded onto class I or II MHC tetramers by tetramerizing the antigen/class I or II MHC complex monomers.

The alpha and beta chains of alpha/beta TCR's, and the gamma and delta chains of gamma/delta TCRs, are generally regarded as each having two "domains", namely variable and constant domains. The variable domain consists of a concatenation of variable region (V), and joining region (J). The variable domain may also include a leader region (L). Beta and delta chains may also include a diversity region (D). The alpha and beta constant domains may also include C-terminal transmembrane (TM) domains that anchor the alpha and beta chains to the cell membrane.

With respect to gamma/delta TCRs, the term "TCR gamma variable domain" as used herein refers to the concatenation of the TCR gamma V (TRGV) region without leader region (L), and the TCR gamma J (TRGJ) region, and the term TCR gamma constant domain refers to the extracellular TRGC region, or to a C-terminal truncated TRGC sequence. Likewise, the term "TCR delta variable domain" refers to the concatenation of the TCR delta V (TRDV) region without leader region (L) and the TCR delta D/J (TRDD/TRDJ) region, and the term "TCR delta constant domain" refers to the extracellular TRDC region, or to a C-terminal truncated TRDC sequence.

TCRs of the present description preferably bind to an inventive peptide-HLA molecule complex with a binding affinity (KD) of about 100 μM or less, about 50 μM or less, about 25 μM or less, or about 10 μM or less. More preferred are high affinity TCRs having binding affinities of about 1 μM or less, about 100 nM or less, about 50 nM or less, about 25 nM or less. Non-limiting examples of preferred binding affinity ranges for TCRs of the present invention include about 1 nM to about 10 nM; about 10 nM to about 20 nM; about 20 nM to about 30 nM; about 30 nM to about 40 nM; about 40 nM to about 50 nM; about 50 nM to about 60 nM; about 60 nM to about 70 nM; about 70 nM to about 80 nM; about 80 nM to about 90 nM; and about 90 nM to about 100 nM.

As used herein in connect with TCRs of the present description, "specific binding" and grammatical variants thereof are used to mean a TCR having a binding affinity (KD) for a peptide-HLA molecule complex of 100 μM or less.

Alpha/beta heterodimeric TCRs of the present description may have an introduced disulfide bond between their constant domains. Preferred TCRs of this type include those which have a TRAC constant domain sequence and a TRBC1 or TRBC2 constant domain sequence except that Thr 48 of TRAC and Ser 57 of TRBC1 or TRBC2 are replaced by cysteine residues, the said cysteines forming a disulfide bond between the TRAC constant domain sequence and the TRBC1 or TRBC2 constant domain sequence of the TCR.

With or without the introduced inter-chain bond mentioned above, alpha/beta hetero-dimeric TCRs of the present description may have a TRAC constant domain sequence and a TRBC1 or TRBC2 constant domain sequence, and the TRAC constant domain sequence and the TRBC1 or TRBC2 constant domain sequence of the TCR may be linked by the native disulfide bond between Cys4 of exon 2 of TRAC and Cys2 of exon 2 of TRBC1 or TRBC2.

TCRs of the present description may comprise a detectable label selected from the group consisting of a radionuclide, a fluorophore and biotin. TCRs of the present description may be conjugated to a therapeutically active agent, such as a radionuclide, a chemotherapeutic agent, or a toxin.

In an embodiment, a TCR of the present description having at least one mutation in the alpha chain and/or having at least one mutation in the beta chain has modified glycosylation compared to the unmutated TCR.

In an embodiment, a TCR comprising at least one mutation in the TCR alpha chain and/or TCR beta chain has a binding affinity for, and/or a binding half-life for, a peptide-HLA molecule complex, which is at least double that of a TCR comprising the unmutated TCR alpha chain and/or unmutated TCR beta chain. Affinity-enhancement of tumor-specific TCRs, and its exploitation, relies on the existence of a window for optimal TCR affinities. The existence of such a window is based on observations that TCRs specific for HLA-A2-restricted pathogens have KD values that are generally about 10-fold lower when compared to TCRs specific for HLA-A2-restricted tumor-associated self-antigens. It is now known, although tumor antigens have the potential to be immunogenic, because tumors arise from the individual's own cells only mutated proteins or proteins with altered translational processing will be seen as foreign by the immune system. Antigens that are upregulated or overexpressed (so called self-antigens) will not necessarily induce a functional immune response against the tumor: T-cells expressing TCRs that are highly reactive to these antigens will have been negatively selected within the thymus in a process known as central tolerance, meaning that only T-cells with low-affinity TCRs for self-antigens remain. Therefore, affinity of TCRs or variants of the present description to peptides of the invention can be enhanced by methods well known in the art.

The present description further relates to a method of identifying and isolating a TCR according to the present description, said method comprising incubating PBMCs from HLA-A*02-negative healthy donors with A2/peptide monomers, incubating the PBMCs with tetramer-phycoerythrin (PE) and isolating the high avidity T-cells by fluorescence activated cell sorting (FACS)—Calibur analysis.

The present description further relates to a method of identifying and isolating a TCR according to the present description, said method comprising obtaining a transgenic mouse with the entire human TCRαβ gene loci (1.1 and 0.7 Mb), whose T-cells express a diverse human TCR repertoire that compensates for mouse TCR deficiency, immunizing the mouse with peptide, incubating PBMCs obtained from the transgenic mice with tetramer-phycoerythrin (PE), and isolating the high avidity T-cells by fluorescence activated cell sorting (FACS)—Calibur analysis.

In one aspect, to obtain T-cells expressing TCRs of the present description, nucleic acids encoding TCR-alpha and/or TCR-beta chains of the present description are cloned into expression vectors, such as gamma retrovirus or lentivirus. The recombinant viruses are generated and then tested for functionality, such as antigen specificity and functional avidity. An aliquot of the final product is then used to transduce the target T-cell population (generally purified from patient PBMCs), which is expanded before infusion into the patient.

In another aspect, to obtain T-cells expressing TCRs of the present description, TCR RNAs are synthesized by techniques known in the art, e.g., in vitro transcription systems. The in vitro-synthesized TCR RNAs are then introduced into primary CD8+ T-cells obtained from healthy donors by electroporation to re-express tumor specific TCR-alpha and/or TCR-beta chains.

To increase the expression, nucleic acids encoding TCRs of the present description may be operably linked to strong promoters, such as retroviral long terminal repeats (LTRs), cytomegalovirus (CMV), murine stem cell virus (MSCV) U3, phosphoglycerate kinase (PGK), β-actin, ubiquitin, and a simian virus 40 (SV40)/CD43 composite promoter, elongation factor (EF)-1a and the spleen focus-forming virus (SFFV) promoter. In a preferred embodiment, the promoter is heterologous to the nucleic acid being expressed.

In addition to strong promoters, TCR expression cassettes of the present description may contain additional elements that can enhance transgene expression, including a central polypurine tract (cPPT), which promotes the nuclear translocation of lentiviral constructs (Follenzi et al., 2000), and the woodchuck hepatitis virus posttranscriptional regulatory element (wPRE), which increases the level of transgene expression by increasing RNA stability (Zufferey et al., 1999).

The alpha and beta chains of a TCR of the present invention may be encoded by nucleic acids located in separate vectors, or may be encoded by polynucleotides located in the same vector.

Achieving high-level TCR surface expression requires that both the TCR-alpha and TCR-beta chains of the introduced TCR be transcribed at high levels. To do so, the TCR-alpha and TCR-beta chains of the present description may be cloned into bi-cistronic constructs in a single vector, which has been shown to be capable of over-coming this obstacle. The use of a viral intraribosomal entry site (IRES) between the TCR-alpha and TCR-beta chains results in the coordinated expression of both chains, because the TCR-alpha and TCR-beta chains are generated from a single transcript that is broken into two proteins during translation, ensuring that an equal molar ratio of TCR-alpha and TCR-beta chains are produced. (Schmitt et al. 2009).

Nucleic acids encoding TCRs of the present description may be codon optimized to increase expression from a host cell. Redundancy in the genetic code allows some amino acids to be encoded by more than one codon, but certain codons are less "op-timal" than others because of the relative availability of matching tRNAs as well as other factors (Gustafsson et al., 2004). Modifying the TCR-alpha and TCR-beta gene sequences such that each amino acid is encoded by the optimal codon for mammalian gene expression, as well as eliminating mRNA instability motifs or cryptic splice sites, has been shown to significantly enhance TCR-alpha and TCR-beta gene expression (Scholten et al., 2006).

Furthermore, mispairing between the introduced and endogenous TCR chains may result in the acquisition of specificities that pose a significant risk for autoimmunity. For example, the formation of mixed TCR dimers may reduce the number of CD3 molecules available to form properly paired TCR complexes, and therefore can significantly decrease the functional avidity of the cells expressing the introduced TCR (Kuball et al., 2007).

To reduce mispairing, the C-terminus domain of the introduced TCR chains of the present description may be modified in order to promote interchain affinity, while decreasing the ability of the introduced chains to pair with the endogenous TCR. These strategies may include replacing the human TCR-alpha and TCR-beta C-terminus domains with their murine counterparts (murinized C-terminus domain); generating a second interchain disulfide bond in the C-terminus domain by introducing a second cysteine residue into both the TCR-alpha and TCR-beta chains of the introduced TCR (cysteine modification); swapping interacting residues in the TCR-alpha and TCR-beta chain C-terminus domains ("knob-in-hole"); and fusing the variable domains of the TCR-alpha and TCR-beta chains directly to CD3 (CD3 fusion). (Schmitt et al. 2009).

In an embodiment, a host cell is engineered to express a TCR of the present description. In preferred embodiments, the host cell is a human T-cell or T-cell progenitor. In some embodiments, the T-cell or T-cell progenitor is obtained from a cancer patient. In other embodiments, the T-cell or T-cell progenitor is obtained from a healthy donor. Host cells of the present description can be allogeneic or autologous with respect to a patient to be treated. In one embodiment, the host is a gamma/delta T-cell transformed to express an alpha/beta TCR.

A "pharmaceutical composition" is a composition suitable for administration to a human being in a medical setting. Preferably, a pharmaceutical composition is sterile and produced according to GMP guidelines.

The pharmaceutical compositions comprise the peptides either in the free form or in the form of a pharmaceutically acceptable salt (see also above). In an aspect, a peptide described herein is in the form of a pharmaceutically acceptable salt. In another aspect, a peptide in the form of a pharmeutical salt is in crystalline form.

In an aspect, a pharmaceutically acceptable salt described herein refers to salts which possess toxicity profiles within a range that is acceptable for pharmaceutical applications.

As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral—NH2 group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

In an aspect, pharmacuetically acceptable salts may increase the solubility and/or stability of peptides of described herein. In another aspect, pharmacutical salts described herein may be prepared by conventional means from the corresponding carrier peptide or complex by reacting, for example, the appropriate acid or base with peptides or complexes as described herein. In another aspect, the pharmacuetically acceptable salts are in crystalline form or semi-crystalline form. In yet another aspect, pharmaceutically acceptable salts may include, for example, those described in Handbook of Pharmaceutical Salts: Properties, Selection, and Use By P. H. Stahl and C. G. Wermuth (Wiley-VCH 2002) and L. D. Bighley, S. M. Berge, D. C. Monkhouse, in "Encyclopedia of Pharmaceutical Technology". Eds. J. Swarbrick and J. C. Boylan, Vol. 13, Marcel Dekker, Inc., New York, Basel, Hong Kong 1995, pp. 453-499, each of these references is herein incorporated by reference in their entirety.

The pharmaceutically acceptable salt form of the peptides of the present invention increases stability over native (naked) peptides, i.e., not in the form of a pharmaceutically acceptable salt or otherwise modified. As used herein, increased stability includes measurable decrease or reduction of the following: deamidation, oxidation, hydrolysis, disulfide interchange, racemization and hydrolysis. The stability can be evaluated on a peptide as a finished product or during the production procedure or during storage. Preferably the peptide in the form of a pharmaceutically acceptable salt has sufficient stability in vitro to allow storage at a commercially relevant temperature, such as between about 0° C. and about 60° C., for a commercially relevant period of time, such as at least one week, preferably at least one month, more preferably at least three months, and most preferably at least six months. Stability can be measured using any physiochemical characterization techniques known to those skilled in the art, such as, for example high pressure liquid chromatography (HPLC).

Further, stability of the peptide salts can be determined by less enzymatic degradation (such as by aminopeptidases, exopeptidases, and synthetases) in plasma, and/or having an improved in vivo half life, compared to native peptide. It has been determined that the intracellular half-life of native 9-mer peptides generated for MHC I antigen presentation is only a few seconds, unless they are bound by other molecules such as chaperons or MHC I molecules. Reits et al., Immunity. 2004; 20: 495-506.

In addition, the pharmaceutically acceptable salts of the peptides of the present invention exhibit improved solubility and stability in aqueous solutions. Berge et al., Pharmaceutical Salts, J. Pharm. Sci. 1977; 66(1): 1-19. Preferably the peptide in the form of a pharmaceutically acceptable salt in an aqueous solution is stable for at least 4 days, at least 5 days, at least 6 days, and more preferably at least 7 days.

In an especially preferred embodiment, the pharmaceutical compositions comprise the peptides as salts of acetic acid (acetates), trifluoro acetates or hydrochloric acid (chlorides).

Preferably, the medicament of the present invention is an immunotherapeutic such as a vaccine. It may be administered directly into the patient, into the affected organ or systemically i.d., i.m., s.c., i.p. and i.v., or applied ex vivo to cells derived from the patient or a human cell line which are subsequently administered to the patient, or used in vitro to select a subpopulation of immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and (Longenecker et al., 1993)). The peptide may also be tagged, may be a fusion protein, or may be a hybrid molecule. The peptides whose sequence is given in the present invention are expected to stimulate CD4 or CD8 T cells. However, stimulation of CD8 T cells is more efficient in the presence of help provided by CD4 T-helper cells. Thus, for MHC Class I epitopes that stimulate CD8 T cells the fusion partner or sections of a hybrid molecule suitably provide epitopes which stimulate CD4-positive T cells.

CD4- and CD8-stimulating epitopes are well known in the art and include those identified in the present invention.

In one aspect, the vaccine comprises at least one peptide having the amino acid sequence set forth SEQ ID No. 1 to SEQ ID No. 91, and at least one additional peptide, preferably two to 50, more preferably two to 25, even more preferably two to 20 and most preferably two, three, four, five, six, seven, eight, nine, ten, eleven, twelve, thirteen, fourteen, fifteen, sixteen, seventeen or eighteen peptides. The peptide(s) may be derived from one or more specific TAAs and may bind to MHC class I molecules.

A further aspect of the invention provides a nucleic acid (for example a polynucleotide) encoding a peptide or peptide variant of the invention. The polynucleotide may be, for example, DNA, cDNA, PNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide according to the invention.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc. New Haven, Conn., USA.

A desirable method of modifying the DNA encoding the polypeptide of the invention employs the polymerase chain reaction as disclosed by Saiki R K, et al. (Saiki et al., 1988). This method may be used for introducing the DNA into a suitable vector, for example by engineering in suitable restriction sites, or it may be used to modify the DNA in other useful ways as is known in the art. If viral vectors are used, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed, for example, in U.S. Pat. Nos. 4,440,859, 4,530,901, 4,582,800, 4,677,063, 4,678,751, 4,704,362, 4,710,463, 4,757,006, 4,766,075, and 4,810,648.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec.), plant cells, animal cells and insect cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, N.J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (YCps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the f1 origin. Vectors containing the pre-pro-trypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

In another embodiment two or more peptides or peptide variants of the invention are encoded and thus expressed in a successive order (similar to "beads on a string" constructs). In doing so, the peptides or peptide variants may be linked or fused together by stretches of linker amino acids, such as for example LLLLLL, or may be linked without any additional peptide(s) between them. These constructs can also be used for cancer therapy, and may induce immune responses both involving MHC I and MHC II.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of E. coli such as, for example, the E. coli strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present invention is accomplished by well-known methods that typically depend on the type of vector used. With regard to transformation of prokaryotic host cells, see, for example, Cohen et al. (Cohen et al., 1972) and (Green and Sambrook, 2012). Transformation of yeast cells is described in Sherman et al. (Sherman et al., 1986). The method of Beggs (Beggs, 1978) is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well-known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may usefully be used to express the peptides of the invention such that they may be loaded into appropriate MHC molecules. Thus, the current invention provides a host cell comprising a nucleic acid or an expression vector according to the invention.

In a preferred embodiment, the host cell is an antigen presenting cell, in particular a dendritic cell or antigen presenting cell. APCs loaded with a recombinant fusion protein containing prostatic acid phosphatase (PAP) were approved by the U.S. Food and Drug Administration (FDA) on Apr. 29, 2010, to treat asymptomatic or minimally symptomatic metastatic HRPC (Sipuleucel-T) (Rini et al., 2006; Small et al., 2006).

A further aspect of the invention provides a method of producing a peptide or its variant, the method comprising culturing a host cell and isolating the peptide from the host cell or its culture medium.

In another embodiment the peptide, the nucleic acid or the expression vector of the invention are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g. between 50 µg and 1.5 mg, preferably 125 µg to 500 µg, of peptide or DNA may be given and will depend on the respective peptide or DNA. Dosages of this range were successfully used in previous trials (Walter et al., 2012).

The polynucleotide used for active vaccination may be substantially pure, or contained in a suitable vector or delivery system. The nucleic acid may be DNA, cDNA, PNA, RNA or a combination thereof. Methods for designing and introducing such a nucleic acid are well known in the art. An overview is provided by e.g. Teufel et al. (Teufel et al., 2005). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun" may also be used. The peptide or peptides encoded by the nucleic acid may be a fusion protein, for example with an epitope that stimulates T cells for the respective opposite CDR as noted above.

The medicament of the invention may also include one or more adjuvants. Adjuvants are substances that non-specifically enhance or potentiate the immune response (e.g., immune responses mediated by CD8-positive T cells and helper-T (TH) cells to an antigen, and would thus be considered useful in the medicament of the present invention. Suitable adjuvants include, but are not limited to, 1018 ISS, aluminum salts, AMPLIVAX®, AS15, BCG, CP-870, 893, CpG7909, CyaA, dSLIM, flagellin or TLR5 ligands derived from flagellin, FLT3 ligand, GM-CSF, IC30, IC31, Imiquimod (ALDARA®), resiquimod, ImuFact IMP321, Interleukins as IL-2, IL-13, IL-21, Interferon-alpha or -beta, or pegylated derivatives thereof, IS Patch, ISS, ISCOMATRIX, ISCOMs, JuvImmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactid co-glycolid) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995). Also, cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich et al., 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and derivates thereof (e.g. AmpliGen®, Hiltonal®, poly-(ICLC), poly(IC-R), poly(I:C12U), non-CpG bacterial DNA or RNA as well as immunoactive small molecules and antibodies such as cyclophosphamide, Sunitinib, Bevacizumab®, Celebrex, NCX-4016, sildenafil, tadalafil, vardenafil, Sorafenib, temozolomide, temsirolimus, XL-999, CP-547632, pazopanib, VEGF Trap, ZD2171, AZD2171, anti-CTLA4, other antibodies targeting key structures of the immune system (e.g. anti-CD40, anti-TGFbeta, anti-TNFalpha receptor) and SC58175, which may act therapeutically and/or as an adjuvant. The amounts and concentrations of adjuvants and additives useful in the context of the present invention can readily be determined by the skilled artisan without undue experimentation.

Preferred adjuvants are anti-CD40, imiquimod, resiquimod, GM-CSF, cyclophosphamide, Sunitinib, bevacizumab, interferon-alpha, CpG oligonucleotides and derivates, poly-(I:C) and derivates, RNA, sildenafil, and particulate formulations with PLG or virosomes.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod, resiquimod, and interferon-alpha.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod and resiquimod. In a preferred embodiment of the pharmaceutical composition according to the invention, the adjuvant is cyclophosphamide, imiquimod or resiquimod. Even more preferred adjuvants are Montanide IMS 1312, Montanide ISA 206, Montanide ISA 50V, Montanide ISA-51, poly-ICLC (Hiltonal®) and anti-CD40 mAB, or combinations thereof.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavors, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients (Kibbe, 2000). The composition can be used for a prevention, prophylaxis and/or therapy of adenomatous or cancerous diseases. Exemplary formulations can be found in, for example, EP2112253.

In an aspect, peptides or other molecules described herein may be combined with an aquous carrier. In an aspect, the aquous carrier is selected from ion exchangers, alumina, aluminum stearate, magnesium stearate, lecithin, serum proteins, such as human serum albumin, buffer substances such as phosphates, glycine, sorbic acid, potassium sorbate, partial glyceride mixtures of saturated vegetable fatty acids, salts or electrolytes, such as protamine sulfate, disodium hydrogen phosphate, dicalcium phosphate, potassium hydrogen phosphate, sodium chloride, zinc salts, colloidal silica, magnesium trisilicate, polyvinyl pyrrolidone, polyvinylpyrrolidone-vinyl acetate, cellulose-based substances (e.g., microcrystalline cellulose, hydroxypropyl methylcellulose, hydroxypropyl methylcellulose acetate succinate, hydroxypropyl methylcellulose Phthalate), starch, lactose monohydrate, mannitol, trehalose sodium lauryl sulfate, and crosscarmellose sodium, polyethylene glycol, sodium carboxymethylcellulose, polyacrylates, polymethacrylate, waxes, polyethylene-polyoxypropylene-block polymers, polyethylene glycol and wool fat.

In an aspect, the aquous carrier contains multiple components, such as water together with a non-water carrier component, such as those components described herein. In another aspect, the aquous carrier is capable of imparting improved properties when combined with a peptide or other molecule described herein, for example, improved solubility, efficacy, and/or improved immunotherapy. In addition, the composition can contain excipients, such as buffers, binding agents, blasting agents, diluents, flavors, lubricants, etc. A "pharmaceutically acceptable diluent," for example, may include solvents, bulking agents, stabilizing agents, dispersion media, coatings, antibacterial and antifungal agents, isotonic and absorption delaying agents, and the like which are physiologically compatible. Examples of pharmaceutically acceptable diluents include one or more of saline, phosphate buffered saline, dextrose, glycerol, ethanol, and the like as well as combinations thereof. In many cases it will be preferable to include one or more isotonic agents, for example, sugars such as trehalose and sucrose, polyalcohols such as mannitol, sorbitol, or sodium chloride in the composition. Pharmaceutically acceptable substances such as wetting or minor amounts of auxiliary substances such as wetting or emulsifying agents, preservatives or buffers, are also within the scope of the present invention. In addition, the composition can contain excipients, such as buffers, binding agents, blasting agents, diluents, flavors, and lubricants.

It is important to realize that the immune response triggered by the vaccine according to the invention attacks the cancer in different cell-stages and different stages of development. Furthermore, different cancer associated signaling pathways are attacked. This is an advantage over vaccines that address only one or few targets, which may cause the tumor to easily adapt to the attack (tumor escape). Furthermore, not all individual tumors express the same pattern of antigens. Therefore, a combination of several tumor-associated peptides ensures that every single tumor bears at least some of the targets. The composition is designed in such a way that each tumor is expected to express several of the antigens and cover several independent pathways necessary for tumor growth and maintenance. Thus, the vaccine can easily be used "off-the-shelf" for a larger patient population. This means that a pre-selection of patients to be treated with the vaccine can be restricted to HLA typing, does not require any additional biomarker assessments for antigen expression, but it is still ensured that several targets are simultaneously attacked by the induced immune response, which is important for efficacy (Banchereau et al., 2001; Walter et al., 2012).

As used herein, the term "scaffold" refers to a molecule that specifically binds to an (e.g. antigenic) determinant. In one embodiment, a scaffold is able to direct the entity to which it is attached (e.g. a (second) antigen binding moiety) to a target site, for example to a specific type of tumor cell or tumor stroma bearing the antigenic determinant (e.g. the complex of a peptide with MHC, according to the application at hand). In another embodiment, a scaffold is able to activate signaling through its target antigen, for example a T cell receptor complex antigen. Scaffolds include but are not limited to antibodies and fragments thereof, antigen binding domains of an antibody, comprising an antibody heavy chain variable region and an antibody light chain variable region, binding proteins comprising at least one ankyrin repeat motif and single domain antigen binding (SDAB) molecules, aptamers, (soluble) TCRs and (modified) cells such as allogenic or autologous T cells. To assess whether a molecule is a scaffold binding to a target, binding assays can be performed.

"Specific" binding means that the scaffold binds the peptide-MHC-complex of interest better than other naturally occurring peptide-MHC-complexes, to an extent that a scaffold armed with an active molecule that is able to kill a cell bearing the specific target is not able to kill another cell without the specific target but presenting another peptide-MHC complex(es). Binding to other peptide-MHC complexes is irrelevant if the peptide of the cross-reactive peptide-MHC is not naturally occurring, i.e. not derived from the human HLA-peptidome. Tests to assess target cell killing are well known in the art. They should be performed using target cells (primary cells or cell lines) with unaltered peptide-MHC presentation, or cells loaded with peptides such that naturally occurring peptide-MHC levels are reached.

Each scaffold can comprise a labelling which provides that the bound scaffold can be detected by determining the presence or absence of a signal provided by the label. For example, the scaffold can be labelled with a fluorescent dye or any other applicable cellular marker molecule. Such marker molecules are well known in the art. For example, a fluorescence-labelling, for example provided by a fluorescence dye, can provide a visualization of the bound aptamer by fluorescence or laser scanning microscopy or flow cytometry.

Each scaffold can be conjugated with a second active molecule such as for example IL-21, anti-CD3, and anti-CD28.

For further information on polypeptide scaffolds see for example the background section of WO 2014/071978A1 and the references cited therein.

The present invention further relates to aptamers. Aptamers (see for example WO 2014/191359 and the literature as cited therein) are short single-stranded nucleic acid molecules, which can fold into defined three-dimensional structures and recognize specific target structures. They have appeared to be suitable alternatives for developing targeted therapies. Aptamers have been shown to selectively bind to a variety of complex targets with high affinity and specificity.

Aptamers recognizing cell surface located molecules have been identified within the past decade and provide means for developing diagnostic and therapeutic approaches. Since aptamers have been shown to possess almost no toxicity and immunogenicity they are promising candidates for biomedical applications. Indeed, aptamers, for example prostate-specific membrane-antigen recognizing aptamers, have been successfully employed for targeted therapies and shown to be functional in xenograft in vivo models. Furthermore, aptamers recognizing specific tumor cell lines have been identified.

DNA aptamers can be selected to reveal broad-spectrum recognition properties for various cancer cells, and particularly those derived from solid tumors, while non-tumorigenic and primary healthy cells are not recognized. If the identified aptamers recognize not only a specific tumor sub-type but rather interact with a series of tumors, this renders the aptamers applicable as so-called broad-spectrum diagnostics and therapeutics.

Further, investigation of cell-binding behavior with flow cytometry showed that the aptamers revealed very good apparent affinities that are within the nanomolar range.

Aptamers are useful for diagnostic and therapeutic purposes. Further, it could be shown that some of the aptamers are taken up by tumor cells and thus can function as molecular vehicles for the targeted delivery of anti-cancer agents such as si RNA into tumor cells.

Aptamers can be selected against complex targets such as cells and tissues and complexes of the peptides comprising, preferably consisting of, a sequence according to any of SEQ ID NO 1 to SEQ ID NO 91, according to the invention at hand with the MHC molecule, using the cell-SELEX (Systematic Evolution of Ligands by Exponential enrichment) technique.

The peptides of the present invention can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

Therefore, it is a further aspect of the invention to provide a method for producing a recombinant antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically binding to said human major histocompatibility complex (MHC) class I or II being complexed with said HLA-restricted antigen.

It is a further aspect of the invention to provide an antibody that specifically binds to a human major histocompatibility complex (MHC) class I or II being complexed with a HLA-restricted antigen, wherein the antibody preferably is a polyclonal antibody, monoclonal antibody, bi-specific antibody and/or a chimeric antibody.

Respective methods for producing such antibodies and single chain class I major histocompatibility complexes, as well as other tools for the production of these antibodies are disclosed in WO 03/068201, WO 2004/084798, WO 01/72768, WO 03/070752, and in publications (Cohen et al., 2003a; Cohen et al., 2003b; Denkberg et al., 2003), which for the purposes of the present invention are all explicitly incorporated by reference in their entireties.

Preferably, the antibody is binding with a binding affinity of below 20 nanomolar, preferably of below 10 nanomolar, to the complex, which is also regarded as "specific" in the context of the present invention.

The present invention relates to a peptide comprising a sequence that is selected from the group consisting of SEQ ID NO: 1 to SEQ ID NO: 91, or a variant thereof which is at least 88% homologous (preferably identical) to SEQ ID NO: 1 to SEQ ID NO: 91 or a variant thereof that induces T cells cross-reacting with said peptide, wherein said peptide is not the underlying full-length polypeptide.

The present invention further relates to a peptide comprising a sequence that is selected from the group consisting of SEQ ID NO: 1 to SEQ ID NO: 91 or a variant thereof which is at least 88% homologous (preferably identical) to SEQ ID NO: 1 to SEQ ID NO: 91, wherein said peptide or variant has an overall length of between 8 and 100, preferably between 8 and 30, and most preferred between 8 and 14 amino acids.

The present invention further relates to the peptides according to the invention that have the ability to bind to a molecule of the human major histocompatibility complex (MHC) Class-I or -II.

The present invention further relates to the peptides according to the invention wherein the peptide consists or consists essentially of an amino acid sequence according to SEQ ID NO: 1 to SEQ ID NO: 91.

The present invention further relates to the peptides according to the invention, wherein the peptide is (chemically) modified and/or includes non-peptide bonds.

The present invention further relates to the peptides according to the invention, wherein the peptide is part of a fusion protein, in particular comprising N-terminal amino acids of the HLA-DR antigen-associated invariant chain (Ii), or wherein the peptide is fused to (or into) an antibody, such as, for example, an antibody that is specific for dendritic cells.

The present invention further relates to a nucleic acid, encoding the peptides according to the invention, provided that the peptide is not the complete (full) human protein.

The present invention further relates to the nucleic acid according to the invention that is DNA, cDNA, PNA, RNA or combinations thereof.

The present invention further relates to an expression vector capable of expressing a nucleic acid according to the present invention.

The present invention further relates to a peptide according to the present invention, a nucleic acid according to the present invention or an expression vector according to the present invention for use in medicine, in particular in the treatment of head and neck squamous cell carcinoma.

The present invention further relates to a host cell comprising a nucleic acid according to the invention or an expression vector according to the invention.

The present invention further relates to the host cell according to the present invention that is an antigen presenting cell, and preferably a dendritic cell.

The present invention further relates to a method of producing a peptide according to the present invention, said method comprising culturing the host cell according to the present invention, and isolating the peptide from said host cell or its culture medium.

The present invention further relates to the method according to the present invention, wherein the antigen is loaded onto class I or II MHC molecules expressed on the surface of a suitable antigen-presenting cell by contacting a sufficient amount of the antigen with an antigen-presenting cell.

The present invention further relates to the method according to the invention, wherein the antigen-presenting cell comprises an expression vector capable of expressing said peptide containing SEQ ID NO: 1 to SEQ ID NO: 91 or said variant amino acid sequence.

The present invention further relates to activated T cells, produced by the method according to the present invention, wherein said T cells selectively recognizes a cell which aberrantly expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as according to the present invention.

The present invention further relates to the use of any peptide described, a nucleic acid according to the present invention, an expression vector according to the present invention, a cell according to the present invention, or an activated cytotoxic T lymphocyte according to the present invention as a medicament or in the manufacture of a medicament. The present invention further relates to a use according to the present invention, wherein the medicament is active against cancer.

The present invention further relates to a use according to the invention, wherein the medicament is a vaccine. The present invention further relates to a use according to the invention, wherein the medicament is active against cancer.

The present invention further relates to a use according to the invention, wherein said cancer cells are head and neck squamous cell carcinoma cells or other solid or hematological tumor cells such as acute myelogenous leukemia, breast cancer, bile duct cancer, brain cancer, chronic lymphocytic leukemia, colorectal carcinoma, esophageal cancer, gallbladder cancer, gastric cancer, hepatocellular cancer, melanoma, non-Hodgkin lymphoma, non-small cell lung cancer, ovarian cancer, pancreatic cancer, prostate cancer, renal cell cancer, small cell lung cancer, urinary bladder cancer and uterine cancer.

The present invention further relates to particular marker proteins and biomarkers based on the peptides according to the present invention, herein called "targets" that can be used in the diagnosis and/or prognosis of head and neck squamous cell carcinoma. The present invention also relates to the use of these novel targets for cancer treatment.

The term "antibody" or "antibodies" is used herein in a broad sense and includes both polyclonal and monoclonal antibodies. In addition to intact or "full" immunoglobulin molecules, also included in the term "antibodies" are fragments (e.g. CDRs, Fv, Fab and Fc fragments) or polymers of those immunoglobulin molecules and humanized versions of immunoglobulin molecules, as long as they exhibit any of the desired properties (e.g., specific binding of a head and neck squamous cell carcinoma marker (poly)peptide, delivery of a toxin to a head and neck squamous cell carcinoma cell expressing a cancer marker gene at an increased level, and/or inhibiting the activity of a head and neck squamous cell carcinoma marker polypeptide) according to the invention.

Whenever possible, the antibodies of the invention may be purchased from commercial sources. The antibodies of the invention may also be generated using well-known methods. The skilled artisan will understand that either full length head and neck squamous cell carcinoma marker polypeptides or fragments thereof may be used to generate the antibodies of the invention. A polypeptide to be used for generating an antibody of the invention may be partially or fully purified from a natural source, or may be produced using recombinant DNA techniques.

For example, a cDNA encoding a peptide according to the present invention, such as a peptide according to SEQ ID NO: 1 to SEQ ID NO: 91 polypeptide, or a variant or fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically bind the head and neck squamous cell carcinoma marker polypeptide used to generate the antibody according to the invention.

One of skill in the art will realize that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistry, immunotherapy, etc.; for further guidance on the generation and testing of antibodies, see, e.g., Greenfield, 2014 (Greenfield, 2014)). For example, the antibodies may be tested in ELISA assays or, Western blots, immunohistochemical staining of formalin-fixed cancers or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567, which is hereby incorporated in its entirety).

Monoclonal antibodies of the invention may be prepared using hybridoma methods. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly Fab fragments, can be accomplished using routine techniques known in the art. For instance, digestion can be performed using papain. Examples of papain digestion are described in WO 94/29348 and U.S. Pat. No. 4,342,566. Papain digestion of antibodies typically produces two identical antigen binding fragments, called Fab fragments, each with a single antigen binding site, and a residual Fc fragment. Pepsin treatment yields a F(ab')2 fragment and a pFc' fragment.

The antibody fragments, whether attached to other sequences or not, can also include insertions, deletions, substitutions, or other selected modifications of particular regions or specific amino acids residues, provided the activity of the fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin.

Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

Antibodies of the invention are preferably administered to a subject in a pharmaceutically acceptable carrier. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. A typical daily dosage of the antibody used alone might range from about 1 (μg/kg to up to 100 mg/kg of body weight or more per day, depending on the factors mentioned above. Following administration of an antibody, preferably for treating head and neck squamous cell carcinoma, the efficacy of the therapeutic antibody can be assessed in various ways well known to the skilled practitioner. For instance, the size, number, and/or distribution of cancer in a subject receiving treatment may be monitored using standard tumor imaging techniques. A therapeutically-administered antibody that arrests tumor growth, results in tumor shrinkage, and/or prevents the development of new tumors, compared to the disease course that would occur in the absence of antibody administration, is an efficacious antibody for treatment of cancer.

It is a further aspect of the invention to provide a method for producing a soluble T-cell receptor (sTCR) recognizing a specific peptide-MHC complex. Such soluble T-cell receptors can be generated from specific T-cell clones, and their affinity can be increased by mutagenesis targeting the complementarity-determining regions. For the purpose of T-cell receptor selection, phage display can be used (US 2010/0113300, (Liddy et al., 2012)). For the purpose of stabilization of T-cell receptors during phage display and in case of practical use as drug, alpha and beta chain can be linked e.g. by non-native disulfide bonds, other covalent bonds (single-chain T-cell receptor), or by dimerization domains (Boulter et al., 2003; Card et al., 2004; Willcox et al., 1999). The T-cell receptor can be linked to toxins, drugs, cytokines (see, for example, US 2013/0115191), and domains recruiting effector cells such as an anti-CD3 domain, etc., in order to execute particular functions on target cells. Moreover, it could be expressed in T cells used for adoptive transfer. Further information can be found in WO 2004/033685A1 and WO 2004/074322A1. A combination of sTCRs is described in WO 2012/056407A1. Further methods for the production are disclosed in WO 2013/057586A1.

In addition, the peptides and/or the TCRs or antibodies or other binding molecules of the present invention can be used to verify a pathologist's diagnosis of a cancer based on a biopsied sample.

The antibodies or TCRs may also be used for in vivo diagnostic assays. Generally, the antibody is labeled with a radionucleotide (such as $^{111}$In, $^{99}$Tc, $^{14}$C, $^{131}$I, $^{3}$H, $^{32}$P or $^{35}$S) so that the tumor can be localized using immunoscintiography. In one embodiment, antibodies or fragments thereof bind to the extracellular domains of two or more targets of a protein selected from the group consisting of the above-mentioned proteins, and the affinity value (Kd) is less than 1×10 μM.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography.

Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the expression of the proteins in situ.

Another aspect of the present invention includes an in vitro method for producing activated T cells, the method comprising contacting in vitro T cells with antigen loaded human MHC molecules expressed on the surface of a suitable antigen-presenting cell for a period of time sufficient to activate the T cell in an antigen specific manner, wherein the antigen is a peptide according to the invention. Preferably a sufficient amount of the antigen is used with an antigen-presenting cell.

Preferably the mammalian cell lacks or has a reduced level or function of the TAP peptide transporter. Suitable cells that lack the TAP peptide transporter include T2, RMA-S and Drosophila cells. TAP is the transporter associated with antigen processing.

The human peptide loading deficient cell line T2 is available from the American Type Culture Collection, 12301 Parklawn Drive, Rockville, Md. 20852, USA under Catalogue No CRL 1992; the Drosophila cell line Schneider line 2 is available from the ATCC under Catalogue No CRL 19863; the mouse RMA-S cell line is described in Ljunggren et al. (Ljunggren and Karre, 1985).

Preferably, before transfection the host cell expresses substantially no MHC class I molecules. It is also preferred that the stimulator cell expresses a molecule important for providing a co-stimulatory signal for T-cells such as any of B7.1, B7.2, ICAM-1 and LFA 3. The nucleic acid sequences of numerous MHC class I molecules and of the co-stimulator molecules are publicly available from the GenBank and EMBL databases.

In case of a MHC class I epitope being used as an antigen, the T cells are CD8-positive T cells.

If an antigen-presenting cell is transfected to express such an epitope, preferably the cell comprises an expression vector capable of expressing a peptide containing SEQ ID NO: 1 to SEQ ID NO: 91, or a variant amino acid sequence thereof.

A number of other methods may be used for generating T cells in vitro. For example, autologous tumor-infiltrating lymphocytes can be used in the generation of CTL. Plebanski et al. (Plebanski et al., 1995) made use of autologous peripheral blood lymphocytes (PLBs) in the preparation of T cells. Furthermore, the production of autologous T cells by pulsing dendritic cells with peptide or polypeptide, or via infection with recombinant virus is possible. Also, B cells can be used in the production of autologous T cells. In addition, macrophages pulsed with peptide or polypeptide, or infected with recombinant virus, may be used in the preparation of autologous T cells. S. Walter et al. (Walter et al., 2003) describe the in vitro priming of T cells by using artificial antigen presenting cells (aAPCs), which is also a suitable way for generating T cells against the peptide of choice. In the present invention, aAPCs were generated by the coupling of preformed MHC: peptide complexes to the surface of polystyrene particles (microbeads) by biotin: streptavidin biochemistry. This system permits the exact control of the MHC density on aAPCs, which allows to selectively elicit high- or low-avidity antigen-specific T cell responses with high efficiency from blood samples. Apart from MHC: peptide complexes, aAPCs should carry other proteins with co-stimulatory activity like anti-CD28 antibodies coupled to their surface. Furthermore, such aAPC-based systems often require the addition of appropriate soluble factors, e. g. cytokines, like interleukin-12.

Allogeneic cells may also be used in the preparation of T cells and a method is described in detail in WO 97/26328, incorporated herein by reference. For example, in addition to Drosophila cells and T2 cells, other cells may be used to present antigens such as CHO cells, baculovirus-infected insect cells, bacteria, yeast, and vaccinia-infected target cells. In addition, plant viruses may be used (see, for example, Porta et al. (Porta et al., 1994) which describes the development of cowpea mosaic virus as a high-yielding system for the presentation of foreign peptides.

The activated T cells that are directed against the peptides of the invention are useful in therapy. Thus, a further aspect of the invention provides activated T cells obtainable by the foregoing methods of the invention.

Activated T cells, which are produced by the above method, will selectively recognize a cell that aberrantly expresses a polypeptide that comprises an amino acid sequence of SEQ ID NO: 1 to SEQ ID NO 91.

Preferably, the T cell recognizes the cell by interacting through its TCR with the HLA/peptide-complex (for example, binding). The T cells are useful in a method of killing target cells in a patient whose target cells aberrantly express a polypeptide comprising an amino acid sequence of the invention wherein the patient is administered an effective number of the activated T cells. The T cells that are administered to the patient may be derived from the patient and activated as described above (i.e. they are autologous T cells). Alternatively, the T cells are not from the patient but are from another individual. Of course, it is preferred if the individual is a healthy individual. By "healthy individual" the inventors mean that the individual is generally in good health, preferably has a competent immune system and, more preferably, is not suffering from any disease that can be readily tested for, and detected.

In vivo, the target cells for the CD8-positive T cells according to the present invention can be cells of the tumor (which sometimes express MHC class II) and/or stromal cells surrounding the tumor (tumor cells) (which sometimes also express MHC class II; (Dengjel et al., 2006)).

The T cells of the present invention may be used as active ingredients of a therapeutic composition. Thus, the invention also provides a method of killing target cells in a patient whose target cells aberrantly express a polypeptide comprising an amino acid sequence of the invention, the method comprising administering to the patient an effective number of T cells as defined above.

By "aberrantly expressed" the inventors also mean that the polypeptide is over-expressed compared to levels of expression in normal tissues or that the gene is silent in the tissue from which the tumor is derived but in the tumor, it is expressed. By "over-expressed" the inventors mean that the polypeptide is present at a level at least 1.2-fold of that present in normal tissue; preferably at least 2-fold, and more preferably at least 5-fold or 10-fold the level present in normal tissue.

T cells may be obtained by methods known in the art, e.g. those described above.

Protocols for this so-called adoptive transfer of T cells are well known in the art. Reviews can be found in: Gattioni et al. and Morgan et al. (Gattinoni et al., 2006; Morgan et al., 2006).

Another aspect of the present invention includes the use of the peptides complexed with MHC to generate a T-cell receptor whose nucleic acid is cloned and is introduced into a host cell, preferably a T cell. This engineered T cell can then be transferred to a patient for therapy of cancer.

Any molecule of the invention, i.e. the peptide, nucleic acid, antibody, expression vector, cell, activated T cell, T-cell receptor or the nucleic acid encoding it, is useful for the treatment of disorders, characterized by cells escaping an immune response. Therefore, any molecule of the present invention may be used as medicament or in the manufacture of a medicament. The molecule may be used by itself or combined with other molecule(s) of the invention or (a) known molecule(s).

The present invention is further directed at a kit comprising:

(a) a container containing a pharmaceutical composition as described above, in solution or in lyophilized form;

(b) optionally a second container containing a diluent or reconstituting solution for the lyophilized formulation; and (c) optionally, instructions for (i) use of the solution or (ii) reconstitution and/or use of the lyophilized formulation.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contain/s instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 µg) and preferably not more than 3 mg/mL/peptide (=1500 µg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, an anti-angiogenesis agent or inhibitor, an apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The present formulation is one that is suitable for administration of the peptides by any acceptable route such as oral (enteral), nasal, ophthal, subcutaneous, intradermal, intramuscular, intravenous or transdermal. Preferably, the administration is s.c., and most preferably i.d. administration may be by infusion pump.

Since the peptides of the invention were isolated from head and neck squamous cell carcinoma, the medicament of the invention is preferably used to treat head and neck squamous cell carcinoma.

The present invention further relates to a method for producing a personalized pharmaceutical for an individual patient comprising manufacturing a pharmaceutical composition comprising at least one peptide selected from a warehouse of pre-screened TUMAPs, wherein the at least one peptide used in the pharmaceutical composition is selected for suitability in the individual patient. In one embodiment, the pharmaceutical composition is a vaccine. The method could also be adapted to produce T cell clones for down-stream applications, such as TCR isolations, or soluble antibodies, and other treatment options.

A "personalized pharmaceutical" shall mean specifically tailored therapies for one individual patient that will only be used for therapy in such individual patient, including actively personalized cancer vaccines and adoptive cellular therapies using autologous patient tissue.

As used herein, the term "warehouse" shall refer to a group or set of peptides that have been pre-screened for immunogenicity and/or over-presentation in a particular tumor type. The term "warehouse" is not intended to imply that the particular peptides included in the vaccine have been pre-manufactured and stored in a physical facility, although that possibility is contemplated. It is expressly contemplated that the peptides may be manufactured de novo for each individualized vaccine produced, or may be pre-manufactured and stored. The warehouse (e.g. in the form of a database) is composed of tumor-associated peptides which were highly overexpressed in the tumor tissue of head and neck squamous cell carcinoma patients with various HLA-A HLA-B and HLA-C alleles. It may contain MHC class I and MHC class II peptides or elongated MHC class I peptides. In addition to the tumor associated peptides collected from several head and neck squamous cell carcinoma tissues, the warehouse may contain HLA-A*02 and HLA-A*24 marker peptides. These peptides allow comparison of the magnitude of T-cell immunity induced by TUMAPS in a quantitative manner and hence allow important conclusion to be drawn on the capacity of the vaccine to elicit anti-tumor responses. Secondly, they function as important positive control peptides derived from a "non-self" antigen in the case that any vaccine-induced T-cell responses to TUMAPs derived from "self" antigens in a patient are not observed. And thirdly, it may allow conclusions to be drawn, regarding the status of immunocompetence of the patient.

TUMAPs for the warehouse are identified by using an integrated functional genomics approach combining gene expression analysis, mass spectrometry, and T-cell immunology (XPresident®). The approach assures that only TUMAPs truly present on a high percentage of tumors but not or only minimally expressed on normal tissue, are chosen for further analysis. For initial peptide selection, head and neck squamous cell carcinoma samples from patients and blood from healthy donors were analyzed in a stepwise approach:
1. HLA ligands from the malignant material were identified by mass spectrometry
2. Genome-wide messenger ribonucleic acid (mRNA) expression analysis was used to identify genes over-expressed in the malignant tissue (head and neck squamous cell carcinoma) compared with a range of normal organs and tissues
3. Identified HLA ligands were compared to gene expression data. Peptides over-presented or selectively presented on tumor tissue, preferably encoded by selectively expressed or over-expressed genes as detected in step 2 were considered suitable TUMAP candidates for a multi-peptide vaccine.
4. Literature research was performed in order to identify additional evidence supporting the relevance of the identified peptides as TUMAPs
5. The relevance of over-expression at the mRNA level was confirmed by redetection of selected TUMAPs from step 3 on tumor tissue and lack of (or infrequent) detection on healthy tissues.
6. In order to assess, whether an induction of in vivo T-cell responses by the selected peptides may be feasible, in vitro immunogenicity assays were performed using human T cells from healthy donors as well as from head and neck squamous cell carcinoma patients.

In an aspect, the peptides are pre-screened for immunogenicity before being included in the warehouse. By way of example, and not limitation, the immunogenicity of the peptides included in the warehouse is determined by a method comprising in vitro T-cell priming through repeated stimulations of CD8+ T cells from healthy donors with artificial antigen presenting cells loaded with peptide/MHC complexes and anti-CD28 antibody.

This method is preferred for rare cancers and patients with a rare expression profile. In contrast to multi-peptide cocktails with a fixed composition as currently developed, the warehouse allows a significantly higher matching of the actual expression of antigens in the tumor with the vaccine. Selected single or combinations of several "off-the-shelf" peptides will be used for each patient in a multitarget approach. In theory, an approach based on selection of e.g. 5 different antigenic peptides from a library of 50 would already lead to approximately 17 million possible drug product (DP) compositions.

In an aspect, the peptides are selected for inclusion in the vaccine based on their suitability for the individual patient based on the method according to the present invention as described herein, or as below.

The HLA phenotype, transcriptomic and peptidomic data is gathered from the patient's tumor material, and blood samples to identify the most suitable peptides for each patient containing "warehouse" and patient-unique (i.e. mutated) TUMAPs. Those peptides will be chosen, which are selectively or over-expressed in the patients' tumor and, where possible, show strong in vitro immunogenicity if tested with the patients' individual PBMCs.

Preferably, the peptides included in the vaccine are identified by a method comprising: (a) identifying tumor-associated peptides (TUMAPs) presented by a tumor sample from the individual patient; (b) comparing the peptides identified in (a) with a warehouse (database) of peptides as described above; and (c) selecting at least one peptide from the warehouse (database) that correlates with a tumor-associated peptide identified in the patient. For example, the TUMAPs presented by the tumor sample are identified by: (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. Preferably, the sequences of MHC ligands are identified by eluting bound peptides from MHC molecules isolated from the tumor sample, and sequencing the eluted ligands. Preferably, the tumor sample and the normal tissue are obtained from the same patient.

In addition to, or as an alternative to, selecting peptides using a warehousing (database) model, TUMAPs may be identified in the patient de novo, and then included in the vaccine. As one example, candidate TUMAPs may be identified in the patient by (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. As another example, proteins may be identified containing mutations that are unique to the tumor sample relative to normal corresponding tissue from the individual patient, and TUMAPs can be identified that specifically target the mutation. For example, the genome of the tumor and of corresponding normal tissue can be sequenced by whole genome sequencing: For discovery of non-synonymous mutations in the protein-coding regions of genes, genomic DNA and RNA are extracted from tumor tissues and normal non-mutated genomic germline DNA is extracted from peripheral blood mononuclear cells (PBMCs). The applied NGS approach is confined to the re-sequencing of protein coding regions (exome re-sequencing). For this purpose, exonic DNA from human samples is captured using vendor-supplied target enrichment kits, followed by sequencing with e.g. a HiSeq2000 (Illumina). Additionally, tumor mRNA is sequenced for direct quantification of gene expression and validation that mutated genes are expressed in the patients' tumors. The resultant millions of sequence reads are processed through software algorithms. The output list contains mutations and gene expression. Tumor-specific somatic mutations are determined by comparison with the PBMC-derived germline variations and prioritized. The de novo identified peptides can then be tested for immunogenicity as described above for the warehouse, and candidate TUMAPs possessing suitable immunogenicity are selected for inclusion in the vaccine.

In one exemplary embodiment, the peptides included in the vaccine are identified by: (a) identifying tumor-associated peptides (TUMAPs) presented by a tumor sample from the individual patient by the method as described above; (b) comparing the peptides identified in a) with a warehouse of peptides that have been prescreened for immunogenicity and over presentation in tumors as compared to corresponding normal tissue; (c) selecting at least one peptide from the warehouse that correlates with a tumor-associated peptide identified in the patient; and (d) optionally, selecting at least one peptide identified de novo in (a) confirming its immunogenicity.

In one exemplary embodiment, the peptides included in the vaccine are identified by: (a) identifying tumor-associated peptides (TUMAPs) presented by a tumor sample from the individual patient; and (b) selecting at least one peptide identified de novo in (a) and confirming its immunogenicity.

Once the peptides for a personalized peptide based vaccine are selected, the vaccine is produced. The vaccine preferably is a liquid formulation consisting of the individual peptides dissolved in between 20-40% DMSO, preferably about 30-35% DMSO, such as about 33% DMSO.

Each peptide to be included into a product is dissolved in DMSO. The concentration of the single peptide solutions has to be chosen depending on the number of peptides to be included into the product. The single peptide-DMSO solutions are mixed in equal parts to achieve a solution containing all peptides to be included in the product with a concentration of ~2.5 mg/ml per peptide. The mixed solution is then diluted 1:3 with water for injection to achieve a concentration of 0.826 mg/ml per peptide in 33% DMSO. The diluted solution is filtered through a 0.22 μm sterile filter. The final bulk solution is obtained.

Final bulk solution is filled into vials and stored at −20° C. until use. One vial contains 700 μL solution, containing 0.578 mg of each peptide. Of this, 500 μL (approx. 400 μg per peptide) will be applied for intradermal injection.

In addition to being useful for treating cancer, the peptides of the present invention are also useful as diagnostics. Since the peptides were generated from head and neck squamous cell carcinoma cells and since it was determined that these peptides are not or at lower levels present in normal tissues, these peptides can be used to diagnose the presence of a cancer.

The presence of claimed peptides on tissue biopsies in blood samples can assist a pathologist in diagnosis of cancer. Detection of certain peptides by means of antibodies, mass spectrometry or other methods known in the art can tell the pathologist that the tissue sample is malignant or inflamed or generally diseased, or can be used as a biomarker for head and neck squamous cell carcinoma. Presence of groups of peptides can enable classification or sub-classification of diseased tissues.

The detection of peptides on diseased tissue specimen can enable the decision about the benefit of therapies involving the immune system, especially if T-lymphocytes are known or expected to be involved in the mechanism of action. Loss of MHC expression is a well described mechanism by which infected of malignant cells escape immuno-surveillance. Thus, presence of peptides shows that this mechanism is not exploited by the analyzed cells.

The peptides of the present invention might be used to analyze lymphocyte responses against those peptides such as T cell responses or antibody responses against the peptide or the peptide complexed to MHC molecules. These lymphocyte responses can be used as prognostic markers for decision on further therapy steps. These responses can also be used as surrogate response markers in immunotherapy approaches aiming to induce lymphocyte responses by different means, e.g. vaccination of protein, nucleic acids, autologous materials, adoptive transfer of lymphocytes. In gene therapy settings, lymphocyte responses against peptides can be considered in the assessment of side effects. Monitoring of lymphocyte responses might also be a valuable tool for follow-up examinations of transplantation therapies, e.g. for the detection of graft versus host and host versus graft diseases.

BRIEF DESCRIPTION OF THE DRAWINGS

The present invention will now be described in the following examples which describe preferred embodiments thereof, and with reference to the accompanying figures, nevertheless, without being limited thereto. For the purposes of the present invention, all references as cited herein are incorporated by reference in their entireties.

FIGS. 1A through 1O show the over-presentation of various peptides in normal tissues (white bars) and head and neck squamous cell carcinoma (black bars). FIG. 1A) Gene symbols: KRT6C, KRT6A, KRT6B, Peptide: GLAGGFG-GPGFPV (SEQ ID NO: 1); Tissues from left to right: 6 adipose tissues, 8 adrenal glands, 1 bile duct, 24 blood cells, 15 blood vessels, 10 bone marrows, 15 brains, 7 breasts, 11 esophagi, 2 eyes, 6 gallbladders, 16 hearts, 17 kidneys, 27 large intestines, 24 livers, 49 lungs, 7 lymph nodes, 12 nerves, 5 ovaries, 15 pancreases, 6 parathyroid glands, 3 peritoneums, 7 pituitary glands, 10 placentas, 3 pleuras, 11 prostates, 9 skeletal muscles, 11 skins, 16 small intestines, 13 spleens, 9 stomachs, 8 testes, 3 thymi, 8 thyroid glands, 18 tracheas, 7 ureters, 8 urinary bladders, 6 uteri, 12 head-and-necks, 17 HNSCC. FIG. 1D) Gene symbol: SLC25A3, Peptide: FVAGYIAGV (SEQ ID NO.: 61); Tissues from left to right: 3 cell lines (2 kidney, 1 pancreas), 7 normal tissues (1 adrenal gland, 1 colon, 2 lymph nodes, 1 placenta, 2 spleens), 36 cancer tissues (5 leukocytic leukemia cancers, 3 brain cancers, 2 breast cancers, 1 esophageal cancer, 1 gallbladder cancer, 5 head-and-neck cancers, 1 kidney cancer, 1 liver cancer, 8 lung cancers, 4 lymph node cancers, 3 ovarian cancers, 2 stomach cancers).

FIGS. 1E to 1Q show the over-presentation of various peptides in different cancer tissues (black dots). Upper part: Median MS signal intensities from technical replicate measurements are plotted as dots for single HLA-A*02 positive normal (grey dots) and tumor samples (black dots) on which the peptide was detected. Tumor and normal samples are grouped according to organ of origin, and box-and-whisker plots represent median, 25th and 75th percentile (box), and minimum and maximum (whiskers) of normalized signal intensities over multiple samples. Normal organs are ordered according to risk categories (blood cells, blood vessels, brain, liver, lung: high risk, grey dots; reproductive organs, breast, prostate: low risk, grey dots; all other organs: medium risk; grey dots). Lower part: The relative peptide detection frequency in every organ is shown as spine plot. Numbers below the panel indicate number of samples on which the peptide was detected out of the total number of samples analyzed for each organ (N=526 for normal samples, N=562 for tumor samples). If the peptide has been detected on a sample but could not be quantified for technical reasons, the sample is included in this representation of detection frequency, but no dot is shown in the upper part of the figure. Tissues (from left to right): Normal samples: blood cells; bloodvess (blood vessels); brain; heart; liver; lung; adipose (adipose tissue); adren.gl. (adrenal gland); bile duct; bladder; BM (bone marrow); cartilage; esoph (esophagus); eye; gallb (gallbladder); head&neck; kidney; large_int (large intestine); LN (lymph node); nerve; pancreas; parathyr (parathyroid gland); perit (peritoneum); pituit (pituitary); pleura; skel.mus (skeletal muscle); skin; small_int (small intestine); spleen; stomach; thyroid; trachea; ureter; breast; ovary; placenta; prostate; testis; thymus; uterus. Tumor samples: AML: acute myeloid leukemia; BRCA: breast cancer; CCC: cholangiocellular carcinoma; CLL: chronic lymphocytic leukemia; CRC: colorectal cancer; GBC: gallbladder cancer; GBM: glioblastoma; GC: gastric cancer; GEJC: stomach cardia esophagus, cancer; HCC: hepatocellular carcinoma; HNSCC: head-and-neck cancer; MEL: melanoma; NHL: non-hodgkin lymphoma; NSCLC: non-small cell lung cancer; OC: ovarian cancer; OSCAR: esophageal cancer; PACA: pancreatic cancer; PRCA: prostate cancer; RCC: renal cell carcinoma; SCLC: small cell lung cancer; UBC: urinary bladder carcinoma; UEC: uterine and endometrial cancer. FIG. 1E) Gene symbols: KRT6C, KRT6A, KRT1, KRT6B, KRT75, KRT5, Peptide: PVCPPGGIQEV (SEQ ID NO.: 2), FIG. 1F) Gene symbol: PKP1, Peptide: SMLNNIINL (SEQ ID NO.: 15), FIG. 1G) Gene symbol: PRKDC, Peptide: GLIEWLENTV (SEQ ID NO.: 45), FIG. 1H) Gene symbol: ATP5G2, ATP5G1, ATP5G3, Peptide: AILGFALSEA (SEQ ID NO.: 57), FIG. 1I) Gene symbol: ITGB4, Peptide: SLSDIQPCL (SEQ ID NO.: 58), FIG. 1J) Gene symbol: KRT5, Peptide: ALMDEINFMKM (SEQ ID NO.: 63), FIG. 1K) Gene symbol: ESRP2, Peptide: ALASAPTSV (SEQ ID NO.: 75), FIG. 1L) Gene symbol: PARP9, Peptide: ILFDEVLTFA (SEQ ID NO.: 76), FIG. 1M) Gene symbol: MCM4, Peptide: QLLQYVYNL (SEQ ID NO.: 83), FIG. 1N) Gene symbol: FHAD1, Peptide: QLIEKITQV (SEQ ID NO.: 85), FIG. 1O) Gene symbol: PLEC, Peptide: ALPEPSPAA (SEQ ID NO.: 87), FIG. 1P) Gene symbol: G3BP1, Peptide: TLNDGVVVQV (SEQ ID NO.: 90), FIG. 1Q) Gene symbol: ODC1, Peptide: MLFENMGAYTV (SEQ ID NO.: 91).

FIG. 2A) Gene symbol: PGLYRP4, Peptide: AIYEGVGWNV (SEQ ID NO.: 33); FIG. 2B) Gene symbol: PAPL, Peptide: KLLPGVQYV (SEQ ID NO.: 38); FIG. 2C) Gene symbols: LGALS7, LGALS7B, Peptide: RLVEVGGDVQL (SEQ ID NO.: 53).

EXAMPLES

Example 1

Identification and Quantitation of Tumor Associated Peptides Presented on the Cell Surface
Tissue Samples Patients' tumor tissues were obtained from: Asterand (Detroit, Mich., USA & Royston, Herts, UK); ProteoGenex Inc. (Culver City, Calif., USA). Normal tissues were obtained from Asterand (Detroit, Mich., USA & Royston, Herts, UK); Bio-Options Inc. (Brea, Calif., USA); BioServe (Beltsville, Md., USA); Capital BioScience Inc. (Rockville, Md., USA); Geneticist Inc. (Glendale, Calif., USA); Kyoto Prefectural University of Medicine (KPUM) (Kyoto, Japan); ProteoGenex Inc. (Culver City, Calif., USA); Tissue Solutions Ltd (Glasgow, UK); University Hospital Geneva (Geneva, Switzerland); University Hospital Heidelberg (Heidelberg, Germany); University Hospital Tübingen (Tübingen, Germany). Written informed consents of all patients had been given before surgery or autopsy. Tissues were shock-frozen immediately after excision and stored until isolation of TUMAPs at −70° C. or below.
Isolation of HLA Peptides from Tissue Samples HLA peptide pools from shock-frozen tissue samples were obtained by immune precipitation from solid tissues according to a slightly modified protocol (Falk et al., 1991; Seeger et al., —123— 1999) using the HLA-A*02-specific antibody BB7.2, the HLA-A, —B, C-specific antibody W6/32, CNBr-activated SEPHAROSE, acid treatment, and ultrafiltration.
Mass Spectrometry Analyses The HLA peptide pools as obtained were separated according to their hydrophobicity by reversed-phase chromatography (nanoAcquity UPLC system, Waters) and the eluting peptides were analyzed in LTQ– velos and fusion hybrid mass spectrometers (ThermoElectron) equipped with an ESI source. Peptide pools were loaded directly onto the analytical fused-silica micro-capillary column (75 μm i.d.× 250 mm) packed with 1.7 μm C18 reversed-phase material (Waters) applying a flow rate of 400 nL per minute. Subsequently, the peptides were separated using a two-step 180 minute-binary gradient from 10% to 33% B at a flow rate of 300 nL per minute. The gradient was composed of Solvent A (0.1% formic acid in water) and solvent B (0.1% formic acid in acetonitrile). A gold coated glass capillary (PicoTip, New Objective) was used for introduction into the nanoESI source. The LTQ-Orbitrap mass spectrometers were operated in the data-dependent mode using a TOP5 strategy. In brief, a scan cycle was initiated with a full scan of high mass accuracy in the Orbitrap (R=30 000), which was followed by MS/MS scans also in the Orbitrap (R=7500) on the 5 most abundant precursor ions with dynamic exclusion of previously selected ions. Tandem mass spectra were interpreted by SEQUEST and additional manual control. The identified peptide sequence was assured by comparison of the generated natural peptide fragmentation pattern with the fragmentation pattern of a synthetic sequence-identical reference peptide.

Figure 1A:
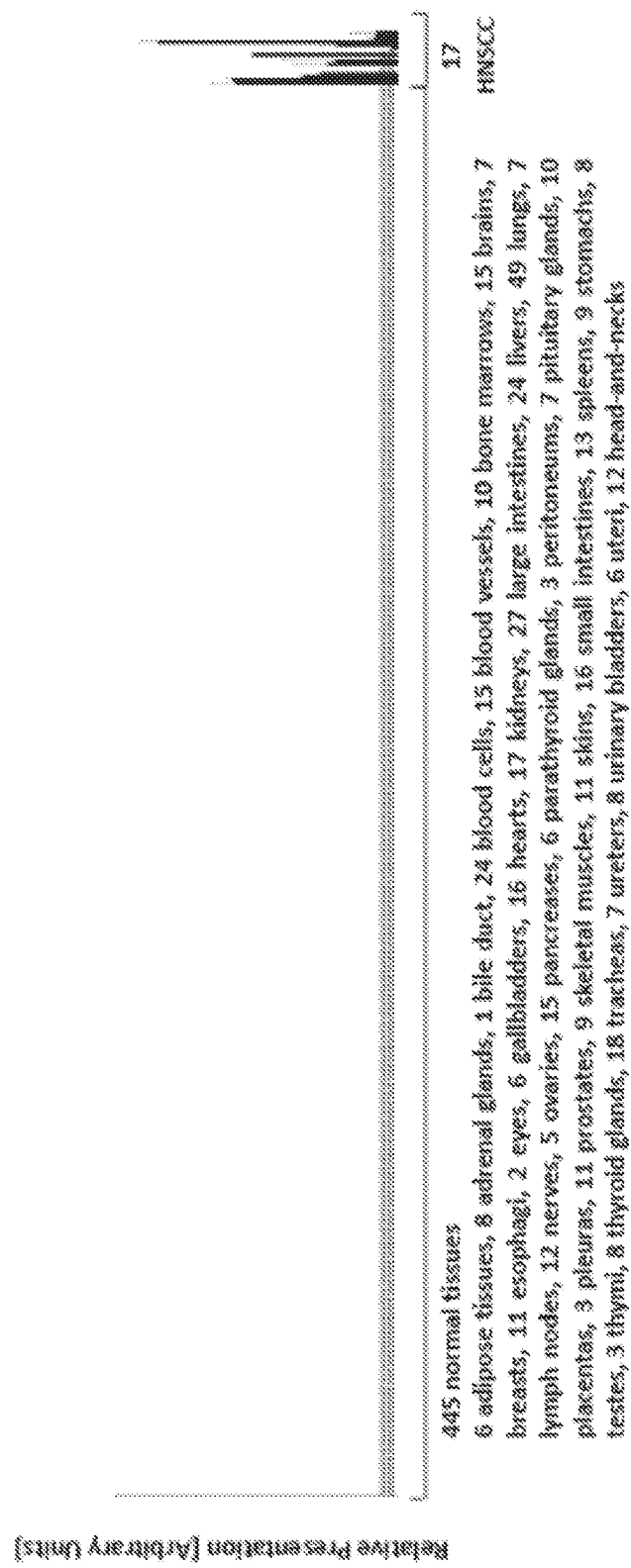
Figure 1B:
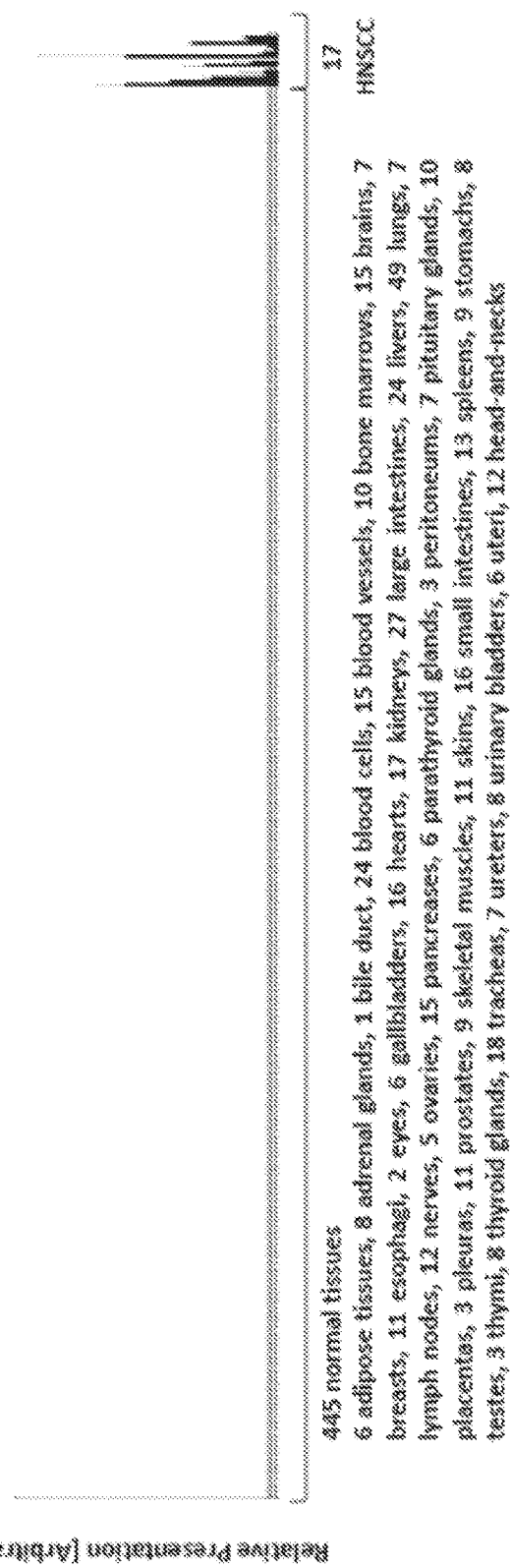
FIG. 1B) Gene symbols: KRT6C, KRT6A, KRT6B, Peptide: SLYGLGGSKRISI (SEQ ID NO.: 3); Tissues from left to right: 6 adipose tissues, 8 adrenal glands, 1 bile duct, 24 blood cells, 15 blood vessels, 10 bone marrows, 15 brains, 7 breasts, 11 esophagi, 2 eyes, 6 gallbladders, 16 hearts, 17 kidneys, 27 large intestines, 24 livers, 49 lungs, 7 lymph nodes, 12 nerves, 5 ovaries, 15 pancreases, 6 parathyroid glands, 3 peritoneums, 7 pituitary glands, 10 placentas, 3 pleuras, 11 prostates, 9 skeletal muscles, 11 skins, 16 small intestines, 13 spleens, 9 stomachs, 8 testes, 3 thymi, 8 thyroid glands, 18 tracheas, 7 ureters, 8 urinary bladders, 6 uteri, 12 head-and-necks, 17 HNSCC.
Figure 1C:
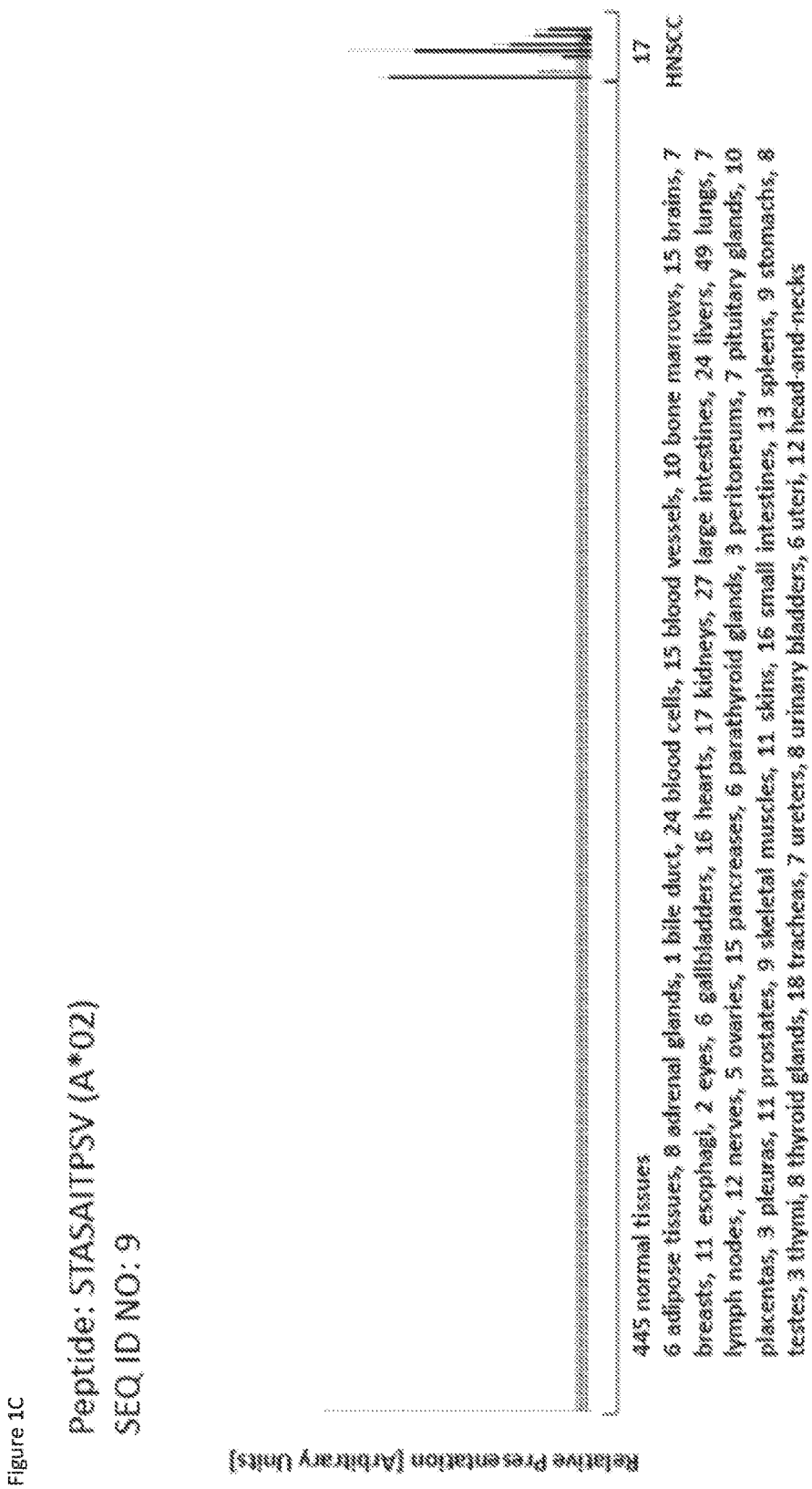
FIG. 1C) Gene symbol: KRT5, Peptide: STA-SAITPSV (SEQ ID NO.: 9); Tissues from left to right: 6 adipose tissues, 8 adrenal glands, 1 bile duct, 24 blood cells, 15 blood vessels, 10 bone marrows, 15 brains, 7 breasts, 11 esophagi, 2 eyes, 6 gallbladders, 16 hearts, 17 kidneys, 27 large intestines, 24 livers, 49 lungs, 7 lymph nodes, 12 nerves, 5 ovaries, 15 pancreases, 6 parathyroid glands, 3 peritoneums, 7 pituitary glands, 10 placentas, 3 pleuras, 11 prostates, 9 skeletal muscles, 11 skins, 16 small intestines, 13 spleens, 9 stomachs, 8 testes, 3 thymi, 8 thyroid glands, 18 tracheas, 7 ureters, 8 urinary bladders, 6 uteri, 12 head-and-necks, 17 HNSCC.
Figure 1E:
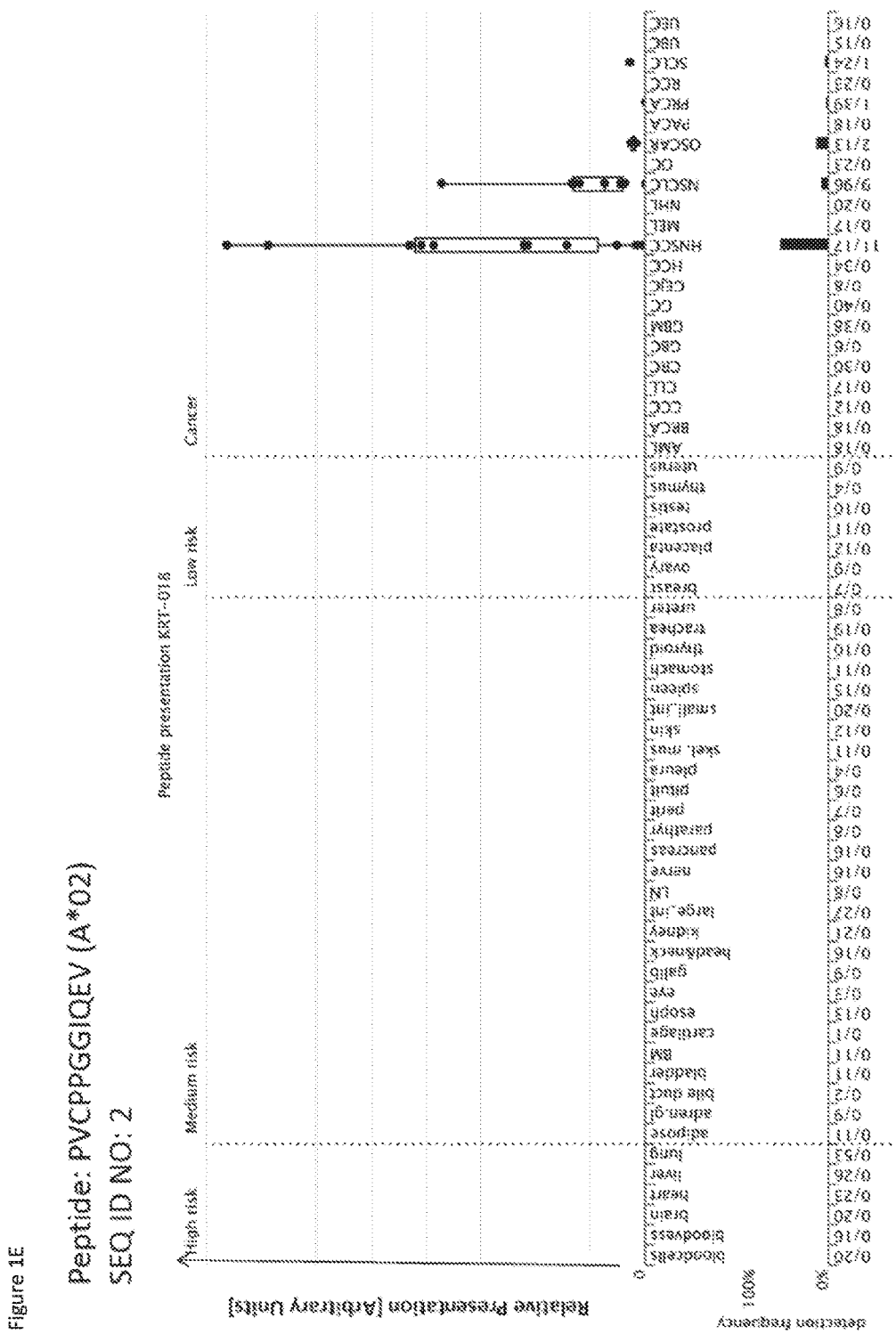
Figure 1G:
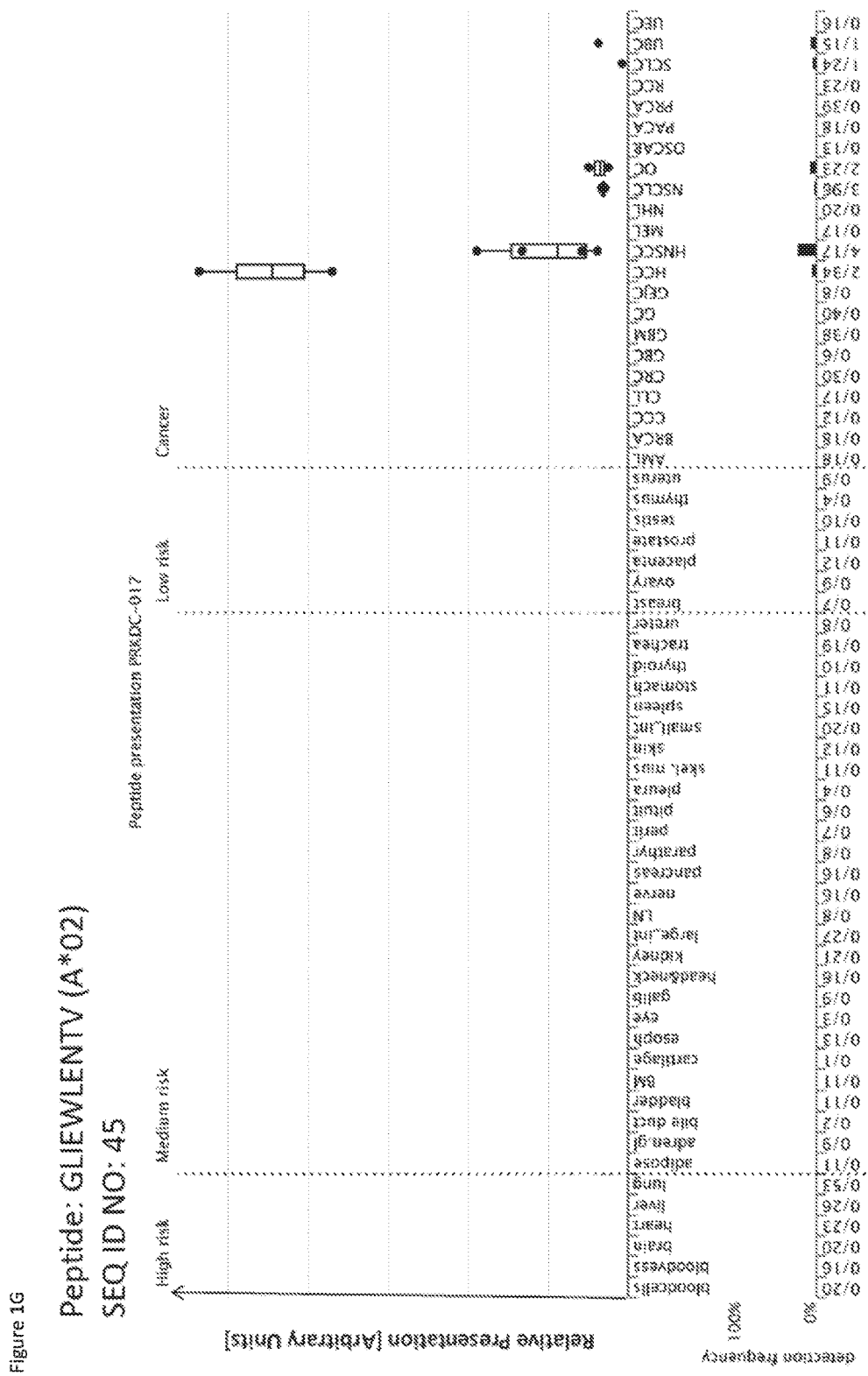
Figure 1H:
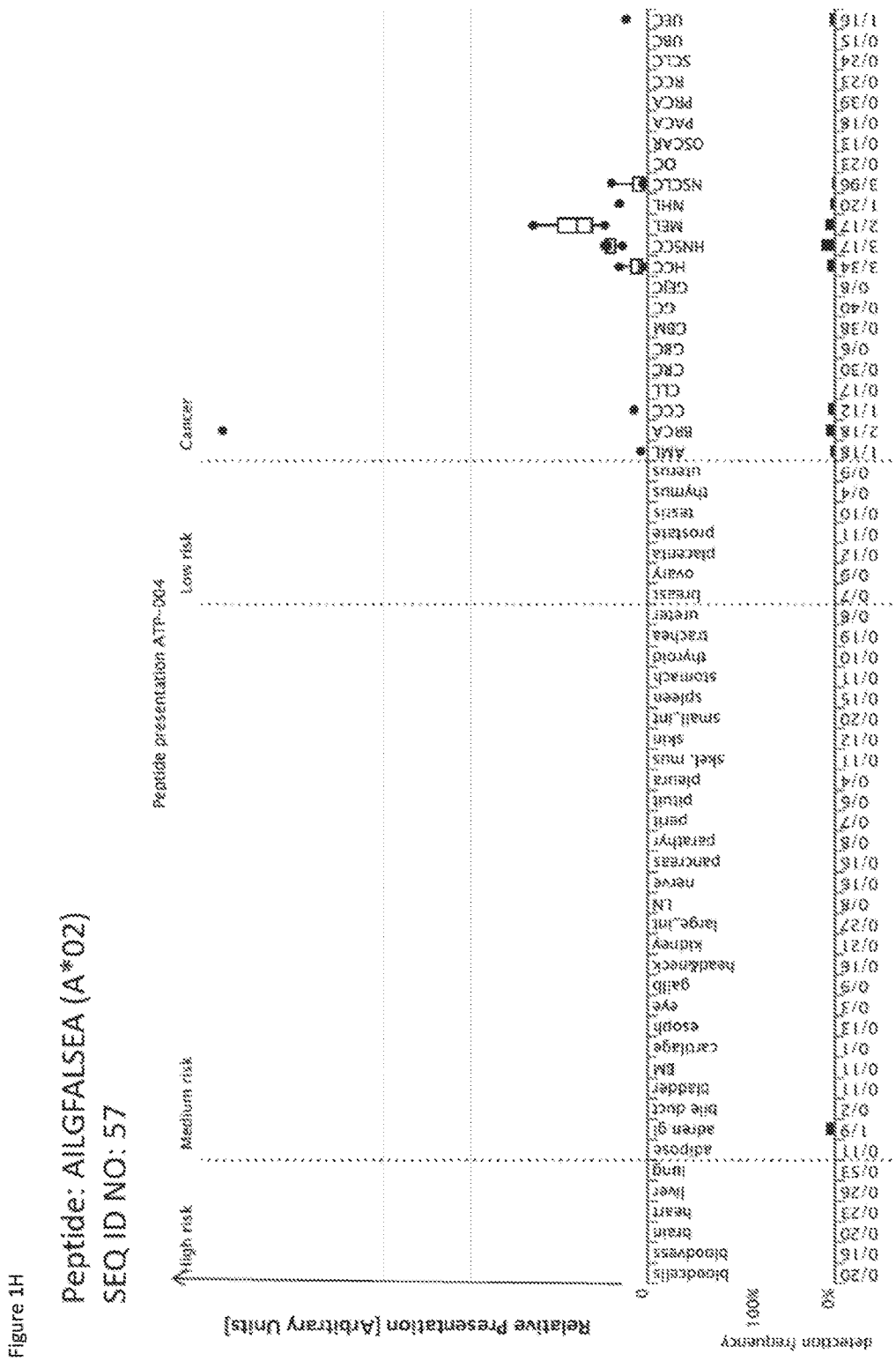
Figure 1J:
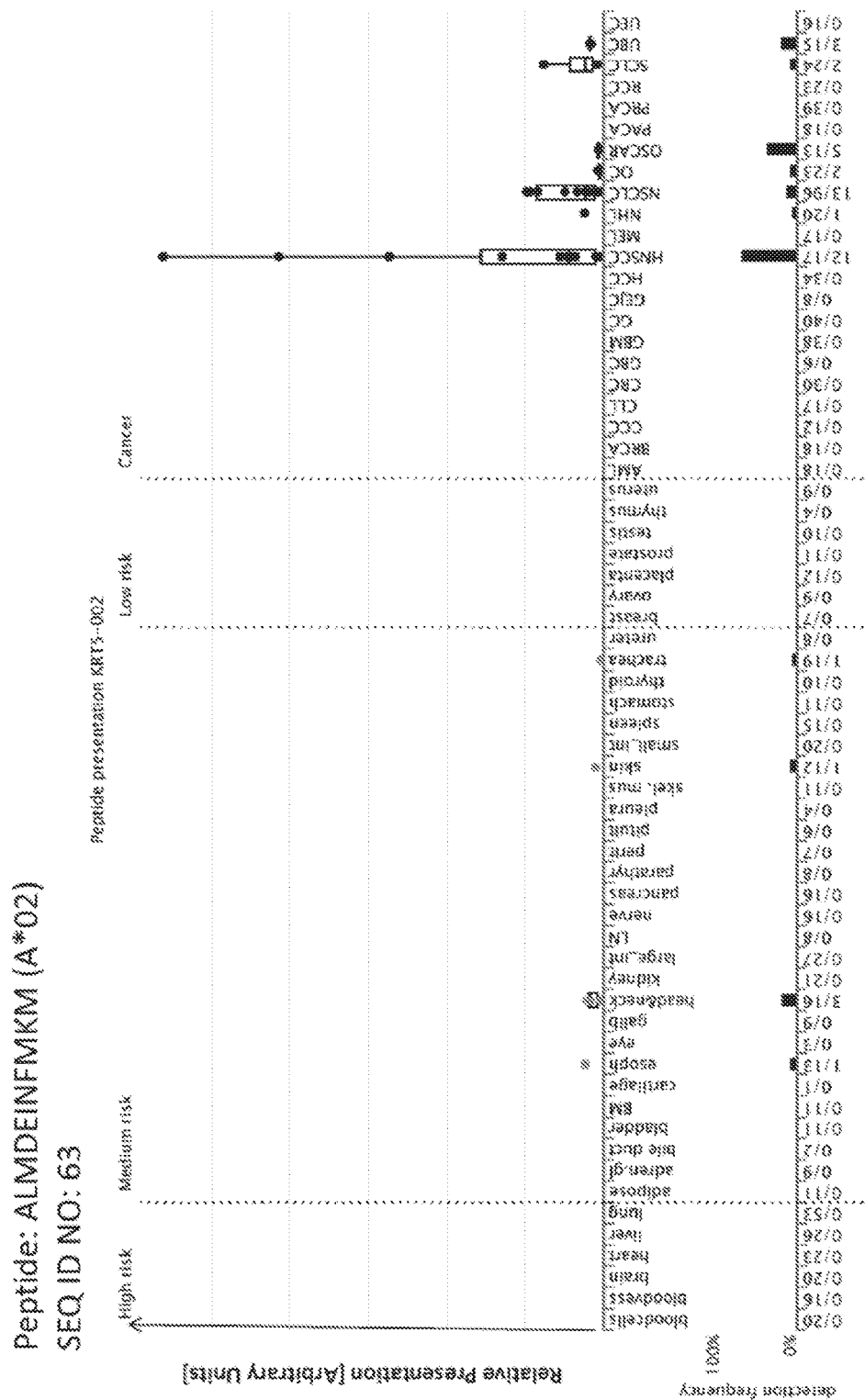
Figure 1K:
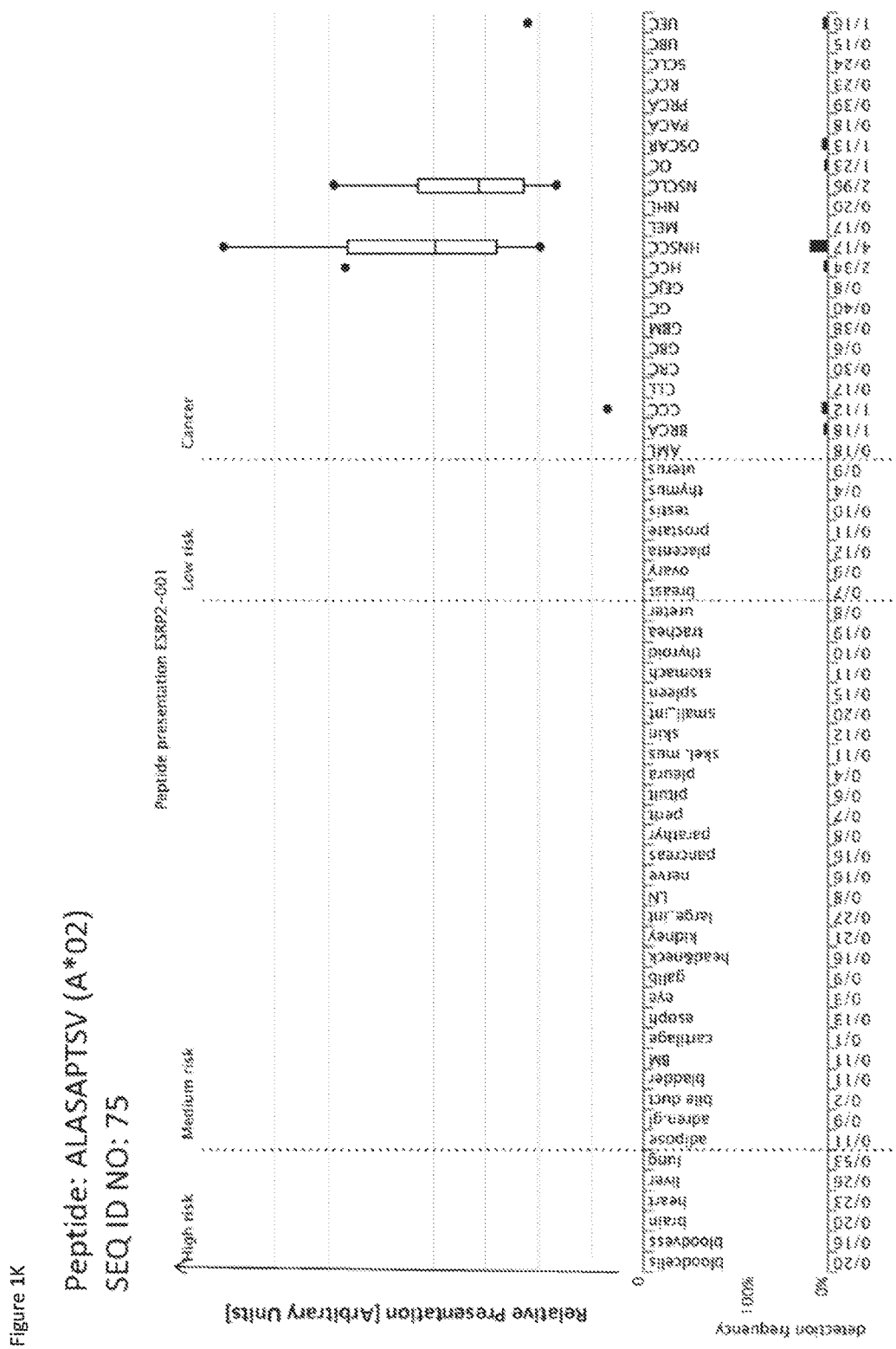
Figure 1L:
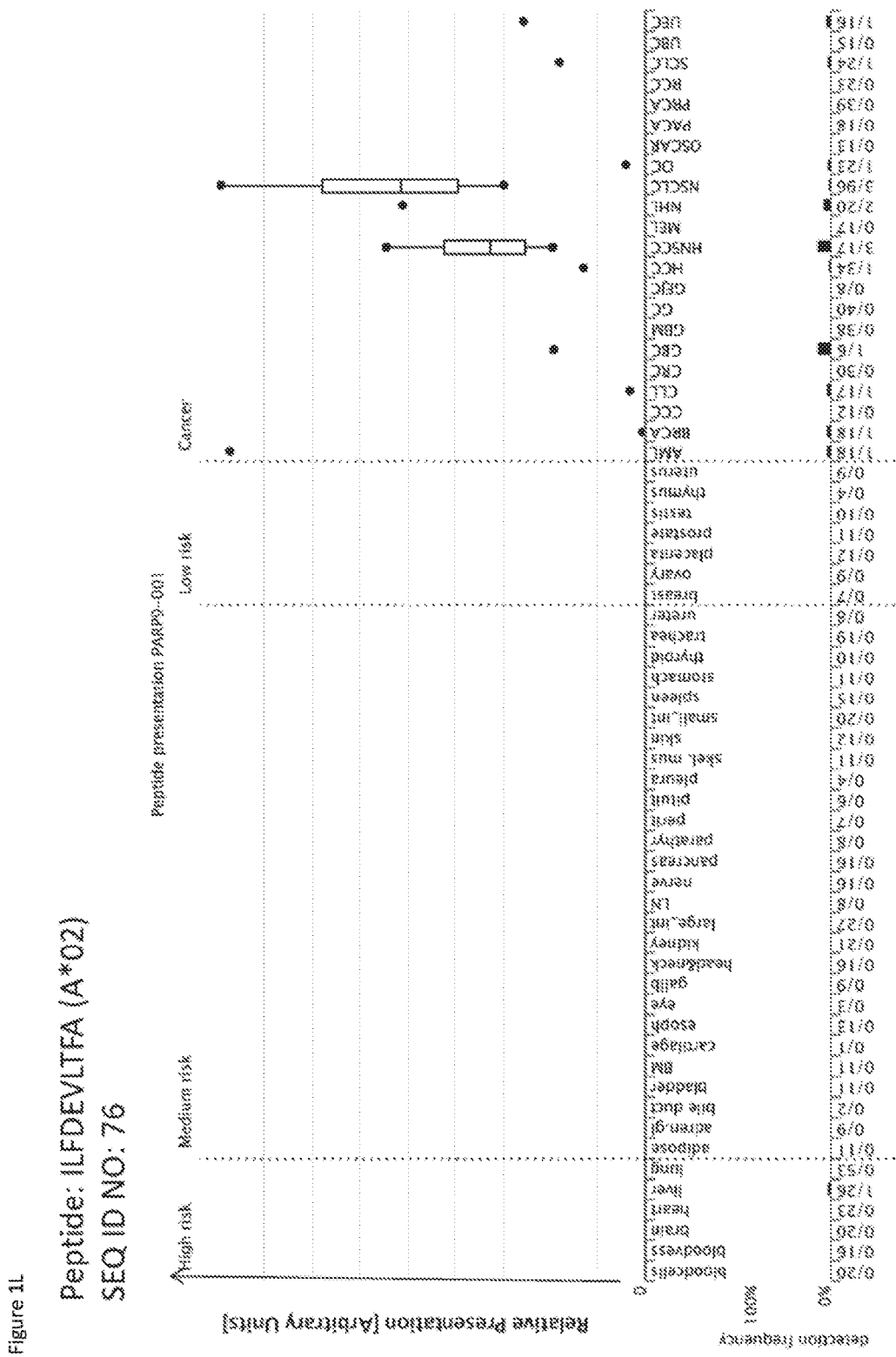
Figure 1M:
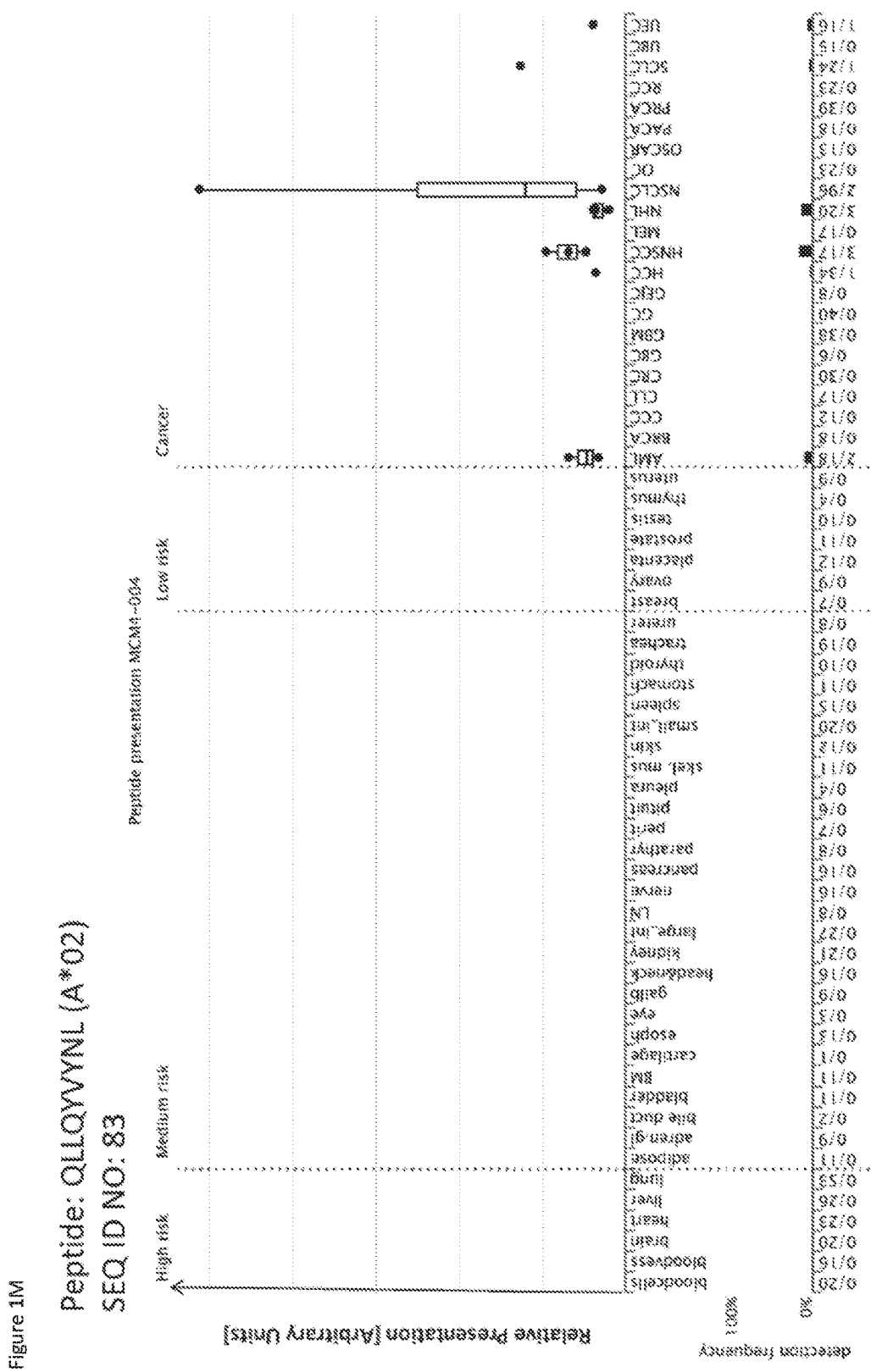
Figure 1N:
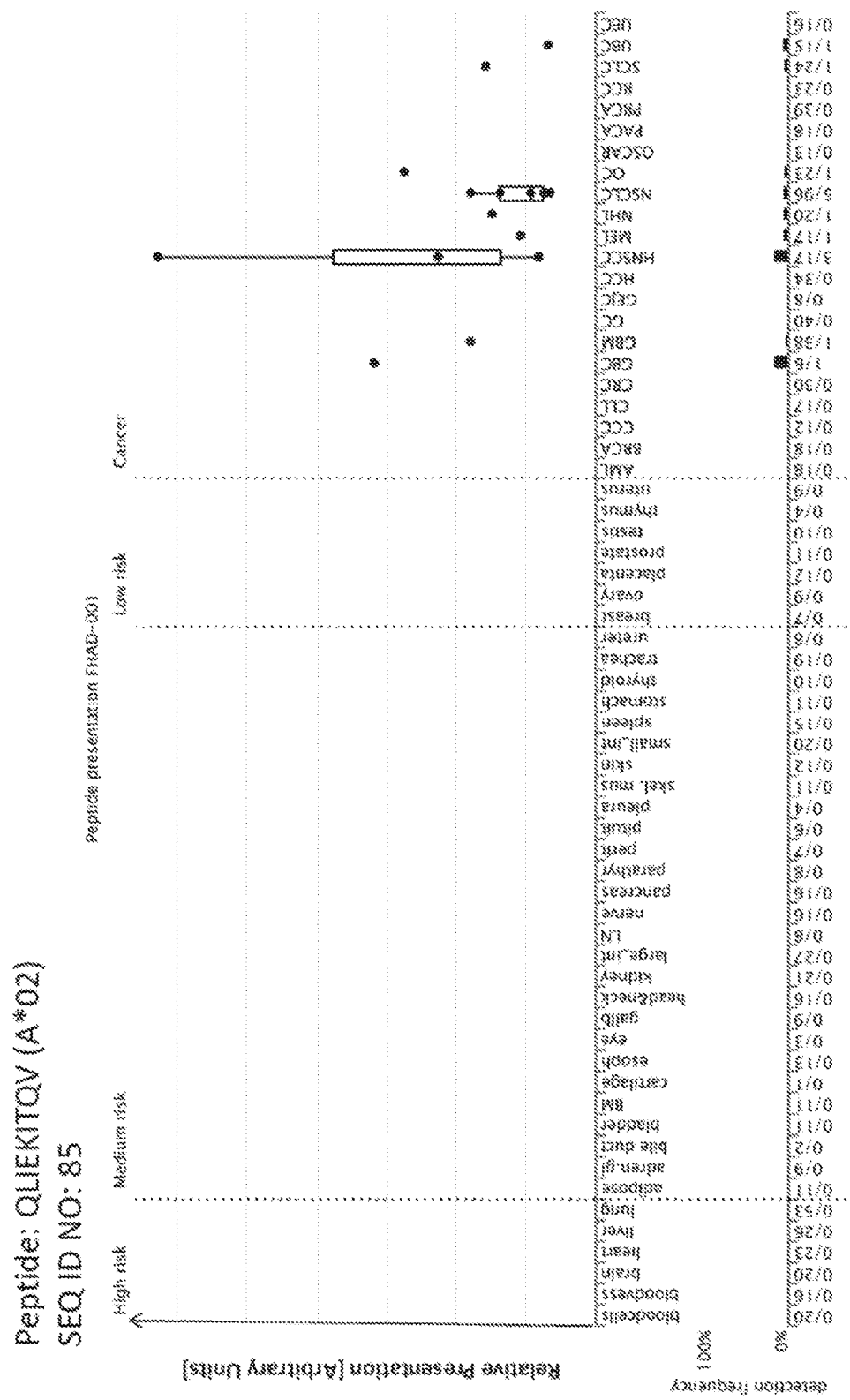
Figure 10:
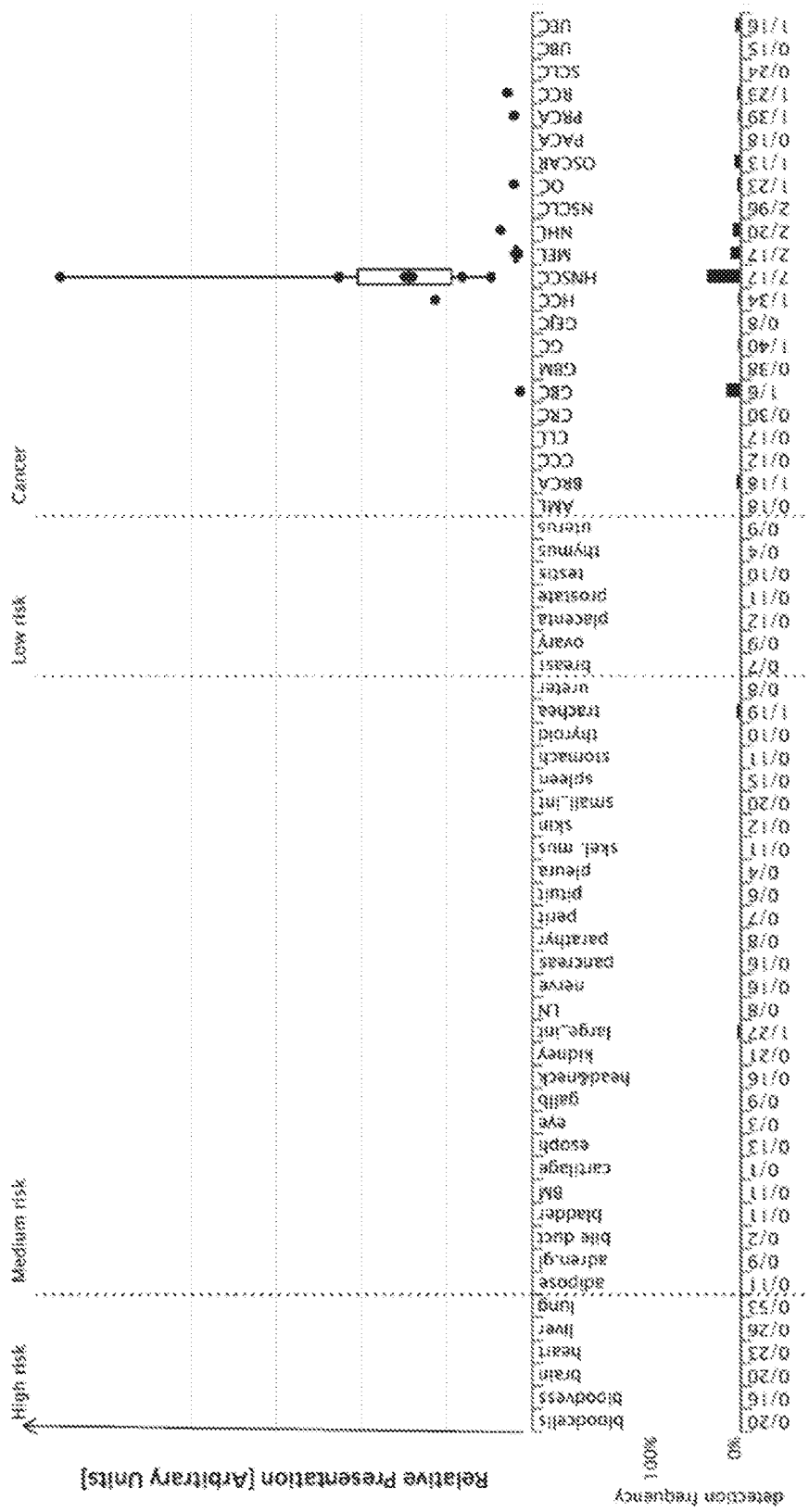
Figure 1P:
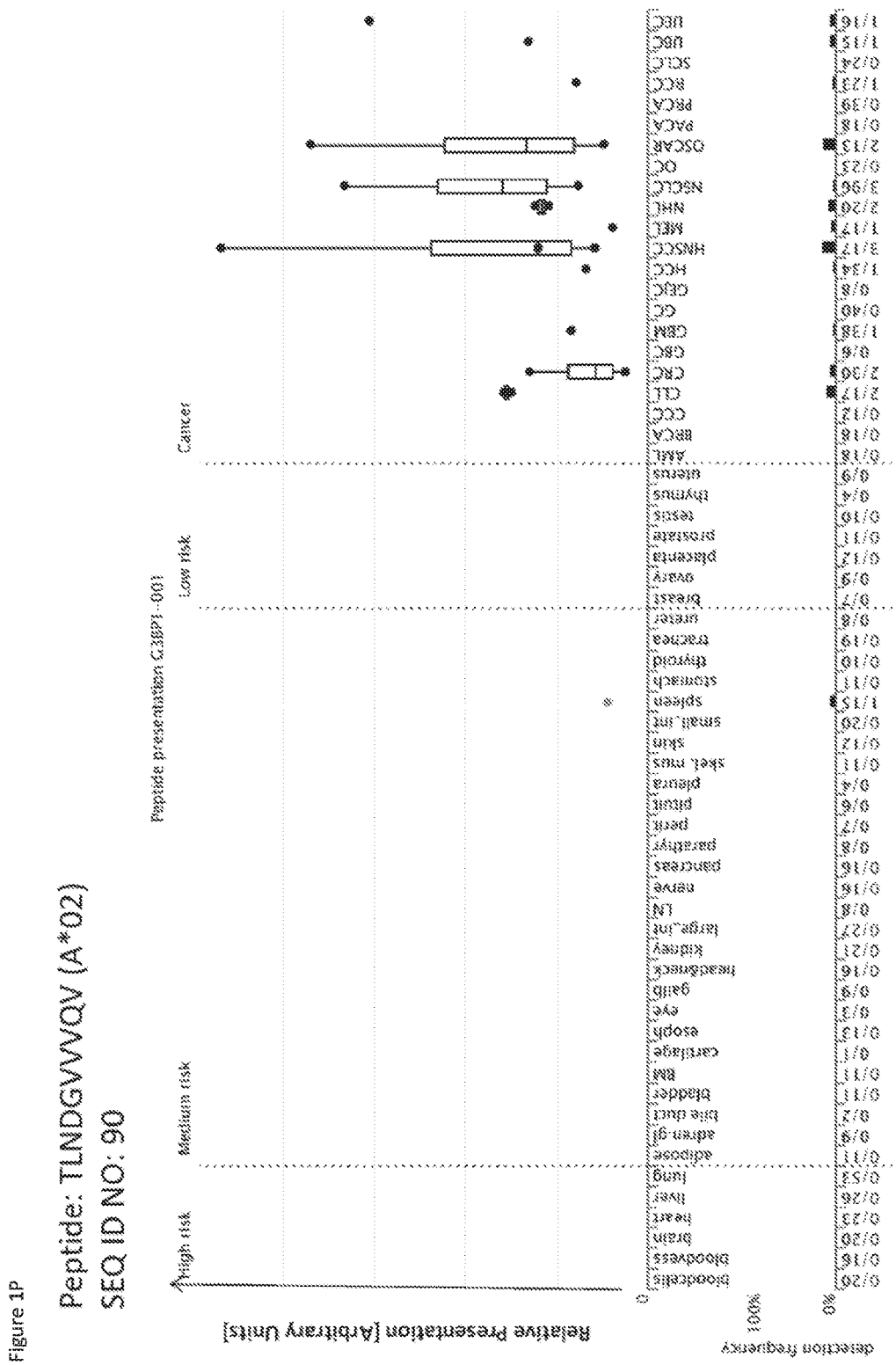
Figure 1Q:
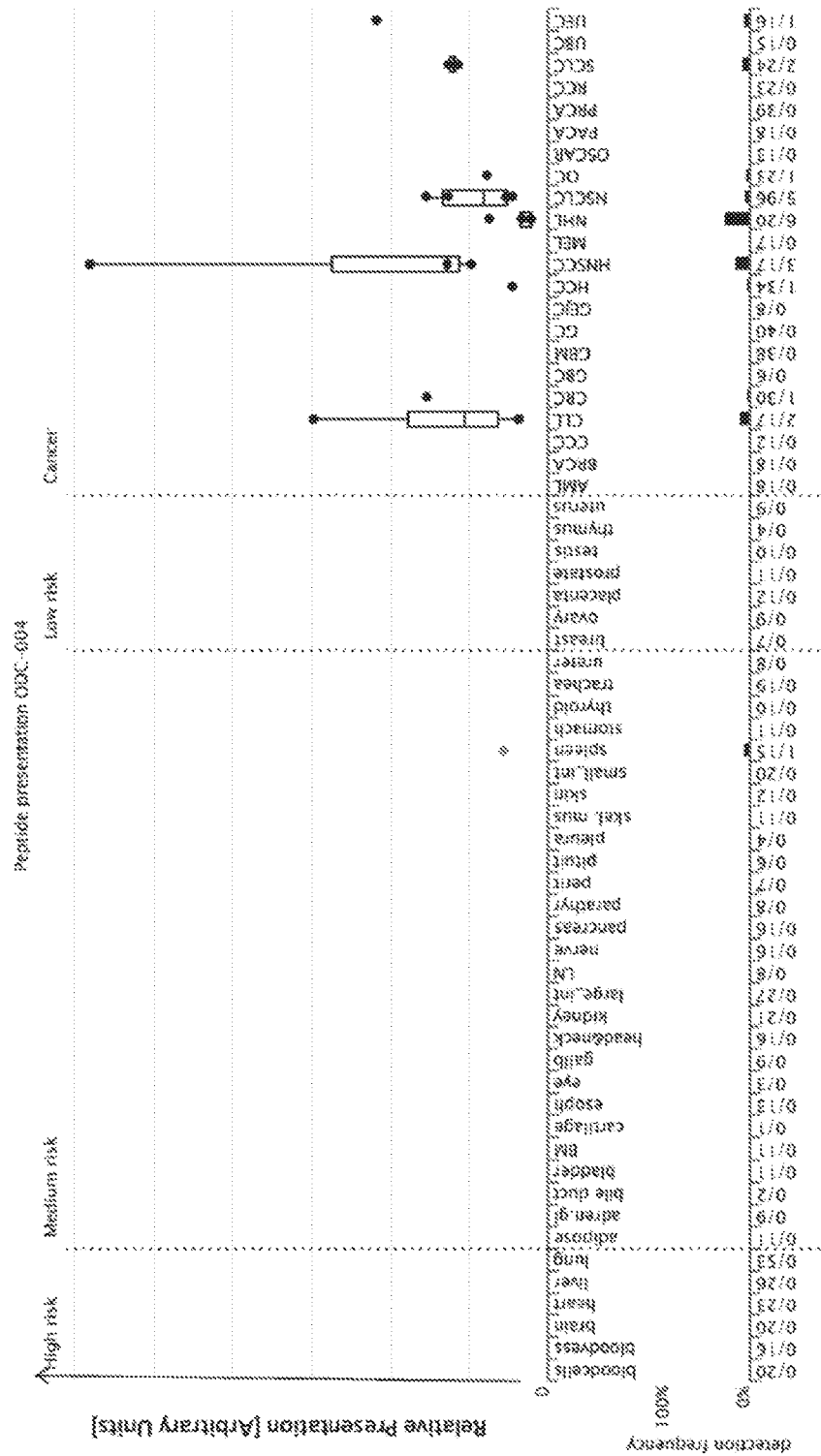

Label-free relative LC-MS quantitation was performed by ion counting i.e. by extraction and analysis of LC-MS features (Mueller et al., 2007). The method assumes that the peptide's LC-MS signal area correlates with its abundance in the sample. Extracted features were further processed by charge state deconvolution and retention time alignment (Mueller et al., 2008; Sturm et al., 2008). Finally, all LC-MS features were cross-referenced with the sequence identification results to combine quantitative data of different samples and tissues to peptide presentation profiles. The quantitative data were normalized in a two-tier fashion according to central tendency to account for variation within technical and biological replicates. Thus, each identified peptide can be associated with quantitative data allowing relative quantification between samples and tissues. In addition, all quantitative data acquired for peptide candidates was inspected manually to assure data consistency and to verify the accuracy of the automated analysis. For each peptide, a presentation profile was calculated showing the mean sample presentation as well as replicate variations. The profiles juxtapose head and neck squamous cell carcinoma samples to a baseline of normal tissue samples. Presentation profiles of exemplary over-presented peptides are shown in FIGS. 1A-1Q. Presentation scores for exemplary peptides are shown in Table 8.

TABLE 8

Presentation scores.

| SEQ ID No | Sequence | Peptide Presentation |
|---|---|---|
| 1 | GLAGGFGGPGFPV | +++ |
| 2 | PVCPPGGIQEV | +++ |
| 3 | SLYGLGGSKRISI | +++ |
| 4 | ILDINDNPPV | +++ |
| 5 | VCPPGGIQEV | +++ |
| 6 | ALYDAELSQM | +++ |
| 7 | ALEEANADLEV | +++ |
| 8 | AQLNIGNVLPV | +++ |
| 9 | STASAITPSV | +++ |
| 10 | TLWPATPPKA | +++ |
| 11 | VLFSSPPVI | +++ |

TABLE 8-continued

Presentation scores.

| SEQ ID No | Sequence | Peptide Presentation |
|---|---|---|
| 12 | TLTDEINFL | +++ |
| 13 | SLVSYLDKV | +++ |
| 14 | RIMEGIPTV | +++ |
| 15 | SMLNNIINL | + |
| 16 | ALKDSVQRA | +++ |
| 17 | SIWPALTQV | +++ |
| 19 | ALAKLLPLL | +++ |
| 20 | YLINEIDRIRA | +++ |
| 21 | FLHEPFSSV | +++ |
| 22 | KLPEPCPSTV | +++ |
| 23 | SLPESGLLSV | +++ |
| 24 | LLIAINPQV | +++ |
| 25 | SLCPPGGIQEV | +++ |
| 26 | TLVDENQSWYL | +++ |
| 27 | YLAEPQWAV | +++ |
| 28 | AVDPVSGSLYV | +++ |
| 29 | RLLPDLDEV | +++ |
| 30 | TLASLGYAVV | +++ |
| 31 | HLATVKLLV | +++ |
| 32 | IQDAEGAIHEV | +++ |
| 33 | AIYEGVGWNV | +++ |
| 34 | ALDTFSVQV | +++ |
| 35 | ALVGDVILTV | +++ |
| 36 | GLWSSIFSL | +++ |
| 37 | ILLEDVFQL | +++ |
| 38 | KLLPGVQYV | +++ |
| 39 | LLPEDDTRDNV | +++ |
| 40 | LLTPLNLQI | +++ |
| 41 | RLNGEGVGQVNISV | +++ |
| 42 | ALYTSGHLL | +++ |
| 43 | AVLGGKLYV | +++ |
| 44 | GLGDDSFPI | +++ |
| 45 | GLIEWLENTV | +++ |
| 46 | GLISSIEAQL | +++ |
| 47 | QLLEGELETL | +++ |
| 48 | YLLDYPNNL | +++ |
| 49 | YLWEAHTNI | +++ |
| 50 | ALSNVVHKV | +++ |
| 51 | FLIPSIIFA | +++ |
| 52 | LLFTGLVSGV | +++ |
| 53 | RLVEVGGDVQL | +++ |
| 54 | RLSGEGVGPV | +++ |
| 55 | VLNVGVAEV | +++ |
| 56 | FLQLETEQV | +++ |
| 58 | SLSDIQPCL | +++ |
| 60 | SLGNFKDDLL | +++ |
| 61 | FVAGYIAGV | +++ |
| 62 | ILSSACYTV | +++ |
| 63 | ALMDEINFMKM | ++ |
| 67 | AQLNLIWQL | + |
| 69 | YVMESMTYL | + |
| 70 | FLFPAFLTA | +++ |
| 71 | SLFPYVVLI | +++ |
| 72 | SLDGNPLAV | +++ |
| 73 | YIDPYKLLPL | +++ |
| 74 | SLTSFLISL | +++ |
| 75 | ALASAPTSV | +++ |
| 78 | VLYGDVEEL | +++ |
| 79 | GLHQDFPSVVL | + |
| 81 | VLAENPDIFAV | +++ |
| 82 | VLDINDNPPV | +++ |
| 83 | QLLQYVYNL | +++ |
| 84 | ALMAGCIQEA | +++ |
| 85 | QLIEKITQV | +++ |
| 86 | SLQERQVFL | +++ |
| 88 | LMAPAPSTV | ++ |

TABLE 8-continued

Presentation scores.

| SEQ ID No | Sequence | Peptide Presentation |
|---|---|---|
| 90 | TLNDGVVVQV | + |
| 91 | MLFENMGAYTV | + |

The table lists peptides that are very highly over-presented on tumors compared to a panel of normal tissues (+++), highly over-presented on tumors compared to a panel of normal tissues (++) or over-presented on tumors compared to a panel of normal tissues (+).
The panel of normal tissues considered relevant for comparison with tumors consisted of: adipose tissue, adrenal gland, bile duct, blood cells, blood vessel, bone marrow, brain, esophagus, eye, gallbladder, head-and-neck, heart, kidney, large intestine, liver, lung, lymph node, nerve, pancreas, parathyroid gland, peritoneum, pituitary, pleura, skeletal muscle, skin, small intestine, spleen, stomach, thymus, thyroid gland, trachea, ureter, urinary bladder.

Example 2

Expression Profiling of Genes Encoding the Peptides of the Invention

Over-presentation or specific presentation of a peptide on tumor cells compared to normal cells is sufficient for its usefulness in immunotherapy, and some peptides are tumor-specific despite their source protein occurring also in normal tissues. Still, mRNA expression profiling adds an additional level of safety in selection of peptide targets for immunotherapies. Especially for therapeutic options with high safety risks, such as affinity-matured TCRs, the ideal target peptide will be derived from a protein that is unique to the tumor and not found on normal tissues.

RNA Sources and Preparation

Surgically removed tissue specimens were provided as indicated above (see Example 1) after written informed consent had been obtained from each patient. Tumor tissue specimens were snap-frozen immediately after surgery and later homogenized with mortar and pestle under liquid nitrogen. Total RNA was prepared from these samples using TRI Reagent (Ambion, Darmstadt, Germany) followed by a cleanup with RNeasy (QIAGEN, Hilden, Germany); both methods were performed according to the manufacturer's protocol.

Total RNA from healthy human tissues for RNASeq experiments was obtained from: Asterand (Detroit, Mich., USA & Royston, Herts, UK); BioCat GmbH (Heidelberg, Germany); Bio-Options Inc. (Brea, Calif., USA); BioServe (Beltsville, Md., USA); Capital BioScience Inc. (Rockville, Md., USA); Geneticist Inc. (Glendale, Calif., USA); Istituto Nazionale Tumori "Pascale" (Naples, Italy); ProteoGenex Inc. (Culver City, Calif., USA); University Hospital Heidelberg (Heidelberg, Germany). Total RNA from tumor tissues for RNASeq experiments was obtained from: Asterand (Detroit, Mich., USA & Royston, Herts, UK); ProteoGenex Inc. (Culver City, Calif., USA).

Quality and quantity of all RNA samples were assessed on an Agilent 2100 Bioanalyzer (Agilent, Waldbronn, Germany) using the RNA 6000 Pico LabChip Kit (Agilent).

RNASeq Experiments

Gene expression analysis of—tumor and normal tissue RNA samples was performed by next generation sequencing (RNASeq) by CeGaT (Tübingen, Germany). Briefly, sequencing libraries are prepared using the Illumina HiSeq v4 reagent kit according to the provider's protocol (Illumina Inc., San Diego, Calif., USA), which includes RNA fragmentation, cDNA conversion and addition of sequencing adaptors. Libraries derived from multiple samples are mixed equimolar and sequenced on the Illumina HiSeq 2500 sequencer according to the manufacturer's instructions, generating 50 bp single end reads. Processed reads are mapped to the human genome (GRCh38) using the STAR software. Expression data are provided on transcript level as RPKM (Reads Per Kilobase per Million mapped reads, generated by the software Cufflinks) and on exon level (total reads, generated by the software Bedtools), based on annotations of the ensembl sequence database (Ensembl77). Exon reads are normalized for exon length and alignment size to obtain RPKM values.

Figure 2A:
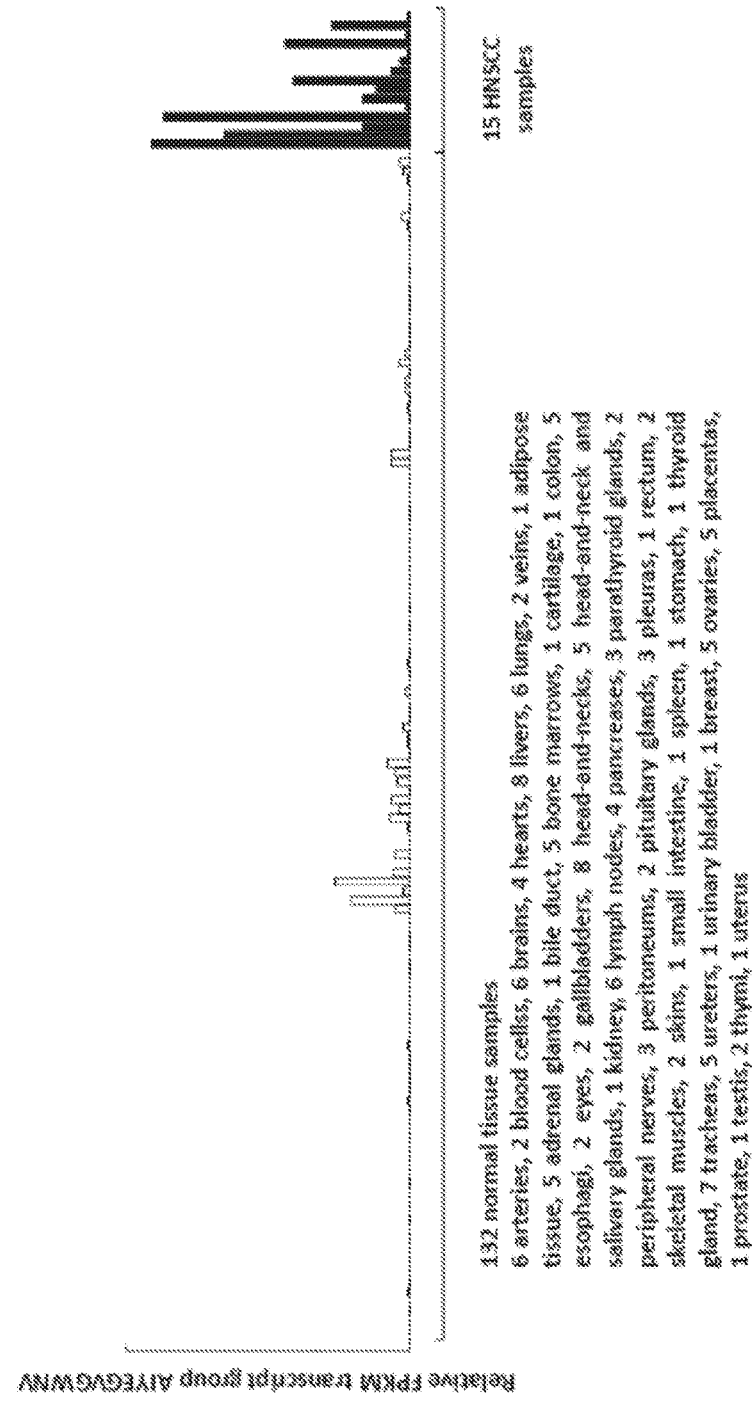
FIGS. 2A through 2C show exemplary expression profiles of source genes of the present invention that are highly over-expressed or exclusively expressed in head and neck squamous cell carcinoma in a panel of normal tissues (white bars) and 15 head and neck squamous cell carcinoma samples (black bars).
Figure 2B:
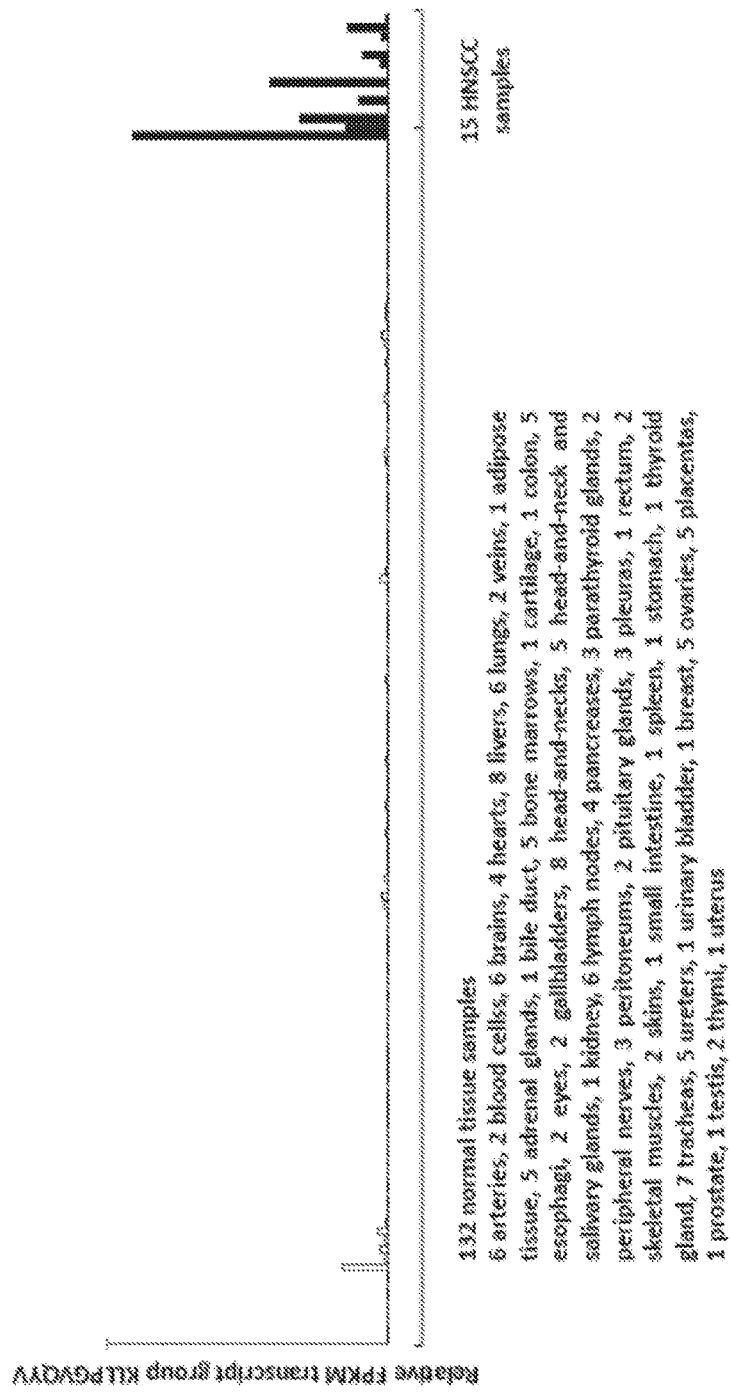
Figure 2C:
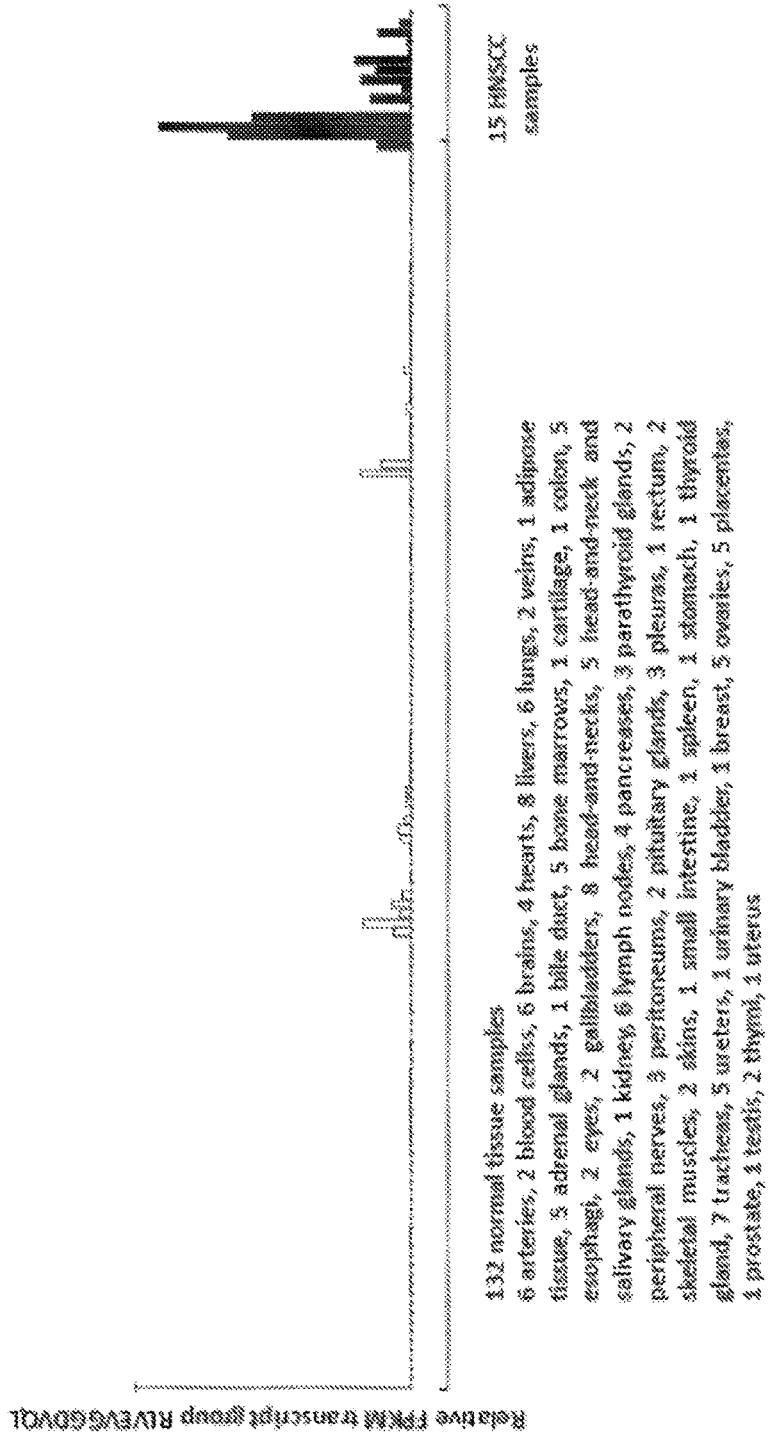

Exemplary expression profiles of source genes of the present invention that are highly over-expressed or exclusively expressed in head and neck squamous cell carcinoma are shown in FIGS. 2A-2C. Expression scores for further exemplary genes are shown in Table 9.

TABLE 9

Expression scores.

| SEQ ID No | Sequence | Gene Expression |
|---|---|---|
| 1 | GLAGGFGGPGFPV | +++ |
| 2 | PVCPPGGIQEV | +++ |
| 3 | SLYGLGGSKRISI | +++ |
| 4 | ILDINDNPPV | +++ |
| 5 | VCPPGGIQEV | +++ |
| 6 | ALYDAELSQM | +++ |
| 7 | ALEEANADLEV | +++ |
| 9 | STASAITPSV | +++ |
| 12 | TLTDEINFL | +++ |
| 14 | RIMEGIPTV | +++ |
| 15 | SMLNNIINL | +++ |
| 19 | ALAKLLPLL | +++ |
| 20 | YLINEIDRIRA | ++ |
| 21 | FLHEPFSSV | +++ |
| 24 | LLIAINPQV | +++ |
| 26 | TLVDENQSWYL | +++ |
| 27 | YLAEPQWAV | + |
| 33 | AIYEGVGWNV | +++ |
| 34 | ALDTFSVQV | ++ |
| 35 | ALVGDVILTV | + |
| 36 | GLWSSIFSL | +++ |
| 38 | KLLPGVQYV | +++ |
| 39 | LLPEDDTRDNV | +++ |
| 40 | LLTPLNLQI | +++ |
| 41 | RLNGEGVGQVNISV | +++ |
| 49 | YLWEAHTNI | + |
| 51 | FLIPSIIFA | +++ |
| 53 | RLVEVGGDVQL | +++ |
| 54 | RLSGEGVGPV | +++ |
| 59 | YLQNEVFGL | +++ |
| 60 | SLGNFKDDLL | +++ |
| 62 | ILSSACYTV | +++ |
| 63 | ALMDEINFMKM | +++ |
| 82 | VLDINDNPPV | +++ |
| 91 | MLFENMGAYTV | ++ |

The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+).
The baseline for this score was calculated from measurements of the following relevant normal tissues: adipose tissue, adrenal gland, artery, bile duct, blood cells, bone marrow, brain, cartilage, colon, esophagus, eye, gallbladder, head-and-neck and salivary gland, heart, kidney, liver, lung, lymph node, pancreas, parathyroid gland, peripheral nerve, peritoneum, pituitary, pleura, rectum, skeletal muscle, skin, small intestine, spleen, stomach, thyroid gland, trachea, ureter, urinary bladder, and vein. In case expression data for several samples of and the same tissue type were available, the arithmetic mean of all respective samples was used for the calculation.

Example 3

In Vitro Immunogenicity for MHC Class I Presented Peptides

In order to obtain information regarding the immunogenicity of the TUMAPs of the present invention, the inventors performed investigations using an in vitro T-cell priming assay based on repeated stimulations of CD8+ T cells with artificial antigen presenting cells (aAPCs) loaded with peptide/MHC complexes and anti-CD28 antibody. This way the inventors could show immunogenicity for HLA-A*0201 restricted TUMAPs of the invention, demonstrating that these peptides are T-cell epitopes against which CD8+ precursor T cells exist in humans (Table 10).

In Vitro Priming of CD8+ T Cells

In order to perform in vitro stimulations by artificial antigen presenting cells loaded with peptide-MHC complex (pMHC) and anti-CD28 antibody, the inventors first isolated CD8+ T cells from fresh HLA-A*02 leukapheresis products via positive selection using CD8 microbeads (Miltenyi Biotech, Bergisch-Gladbach, Germany) of healthy donors obtained from the University clinics Mannheim, Germany, after informed consent.

PBMCs and isolated CD8+ lymphocytes were incubated in T-cell medium (TCM) until use consisting of RPMI-Glutamax (Invitrogen, Karlsruhe, Germany) supplemented with 10% heat inactivated human AB serum (PAN-Biotech, Aidenbach, Germany), 100 U/ml Penicillin/100 µg/ml Streptomycin (Cambrex, Cologne, Germany), 1 mM sodium pyruvate (CC Pro, Oberdorla, Germany), 20 µg/ml Gentamycin (Cambrex). 2.5 ng/ml IL-7 (PromoCell, Heidelberg, Germany) and 10 U/ml IL-2 (Novartis Pharma, Nürnberg, Germany) were also added to the TCM at this step.

Generation of pMHC/anti-CD28 coated beads, T-cell stimulations and readout was performed in a highly defined in vitro system using four different pMHC molecules per stimulation condition and 8 different pMHC molecules per readout condition.

The purified co-stimulatory mouse IgG2a anti human CD28 Ab 9.3 (Jung et al., 1987) was chemically biotinylated using Sulfo-N-hydroxysuccinimidobiotin as recommended by the manufacturer (Perbio, Bonn, Germany). Beads used were 5.6 µm diameter streptavidin coated polystyrene particles (Bangs Laboratories, Illinois, USA).

pMHC used for positive and negative control stimulations were A*0201/MLA-001 (peptide ELAGIGILTV (SEQ ID NO. 157) from modified Melan-A/MART-1) and A*0201/DDX5-001 (YLLPAIVHI from DDX5, SEQ ID NO. 158), respectively.

800.000 beads/200 µl were coated in 96-well plates in the presence of 4×12.5 ng different biotin-pMHC, washed and 600 ng biotin anti-CD28 were added subsequently in a volume of 200 µl. Stimulations were initiated in 96-well plates by co-incubating 1×10$^6$ CD8+ T cells with 2×10$^5$ washed coated beads in 200 µl TCM supplemented with 5 ng/ml IL-12 (PromoCell) for 3 days at 37° C. Half of the medium was then exchanged by fresh TCM supplemented with 80 U/ml IL-2 and incubating was continued for 4 days at 37° C. This stimulation cycle was performed for a total of three times. For the pMHC multimer readout using 8 different pMHC molecules per condition, a two-dimensional combinatorial coding approach was used as previously described (Andersen et al., 2012) with minor modifications encompassing coupling to 5 different fluorochromes. Finally, multimeric analyses were performed by staining the cells with Live/dead near IR dye (Invitrogen, Karlsruhe, Germany), CD8-FITC antibody clone SK1 (BD, Heidelberg, Germany) and fluorescent pMHC multimers. For analysis, a BD LSRII SORP cytometer equipped with appropriate lasers and filters was used. Peptide specific cells were calculated as percentage of total CD8+ cells. Evaluation of multimeric analysis was done using the FlowJo software (Tree Star, Oregon, USA). In vitro priming of specific multimer+CD8+ lymphocytes was detected by comparing to negative control stimulations. Immunogenicity for a given antigen was detected if at least one evaluable in vitro stimulated well of one healthy donor was found to contain a specific CD8+ T-cell line after in vitro stimulation (i.e. this well contained at least 1% of specific multimer+ among CD8+ T-cells and the percentage of specific multimer+ cells was at least 10× the median of the negative control stimulations).

In Vitro Immunogenicity for Head and Neck Squamous Cell Carcinoma Peptides

Figure 3A:
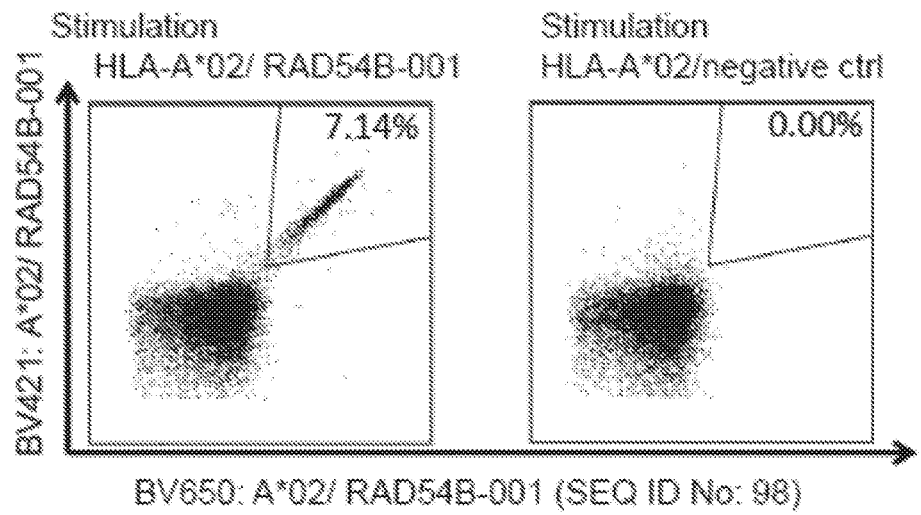
FIGS. 3A and 3B show exemplary immunogenicity data: flow cytometry results after peptide-specific multimer staining.
Figure 3B:
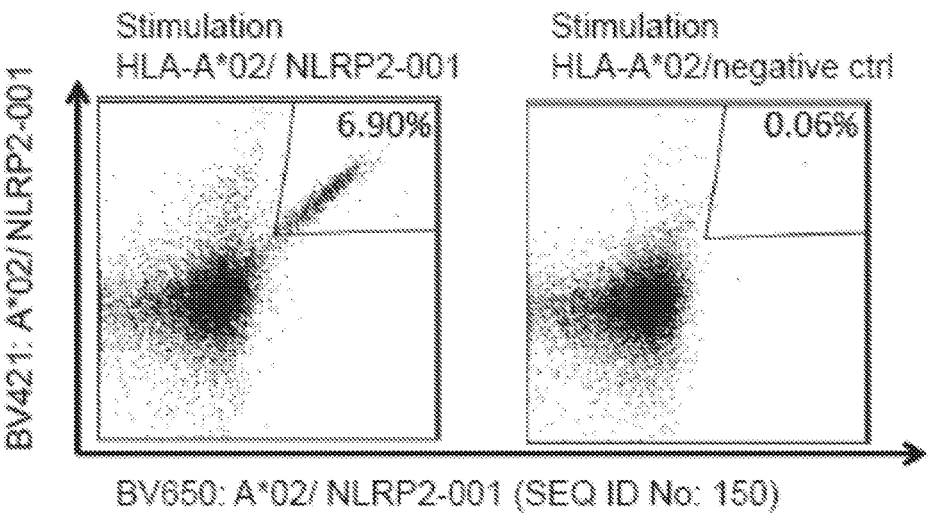
Figure 4A:
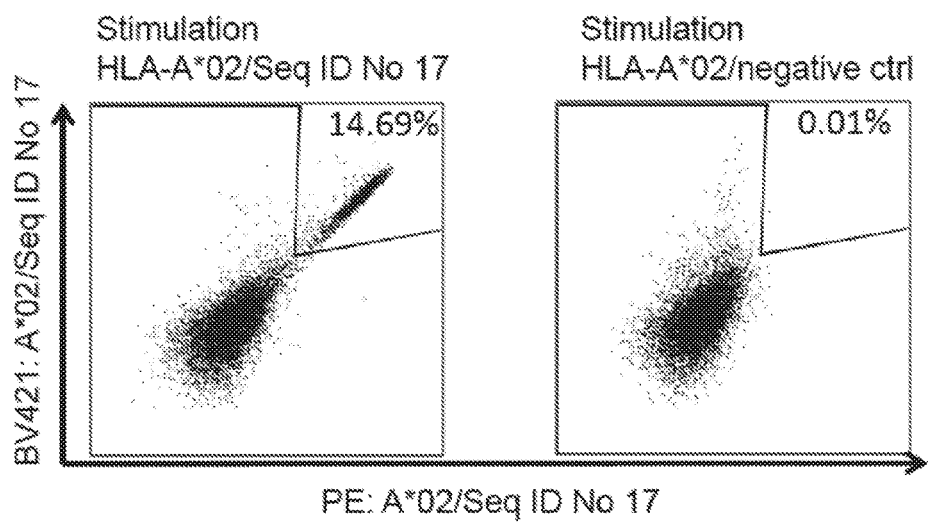
FIGS. 4A-4C show exemplary results of peptide-specific in vitro CD8+ T cell responses of a healthy HLA-A*02+ donor. CD8+ T cells were primed using artificial APCs coated with anti-CD28 mAb and HLA-A*02 in complex with Seq ID NO.: 17 peptide (FIG. 4A, left panel), Seq ID NO.: 28 peptide (FIG. 4B, left panel) and Seq ID NO.: 29 peptide (FIG. 4C, left panel), respectively. After three cycles of stimulation, the detection of peptide-reactive cells was performed by 2D multimer staining with A*02/Seq ID NO.: 17 (FIG. 4A), A*02/Seq ID NO.: 28 (FIG. 4B) or A*02/Seq ID NO.: 29 (FIG. 4C). Right panels (FIGS. 4A, 4B and 4C) show control staining of cells stimulated with irrelevant A*02/peptide complexes. Viable singlet cells were gated for CD8+ lymphocytes. Boolean gates helped excluding false-positive events detected with multimers specific for different peptides. Frequencies of specific multimer+ cells among CD8+ lymphocytes are indicated.
Figure 4B:
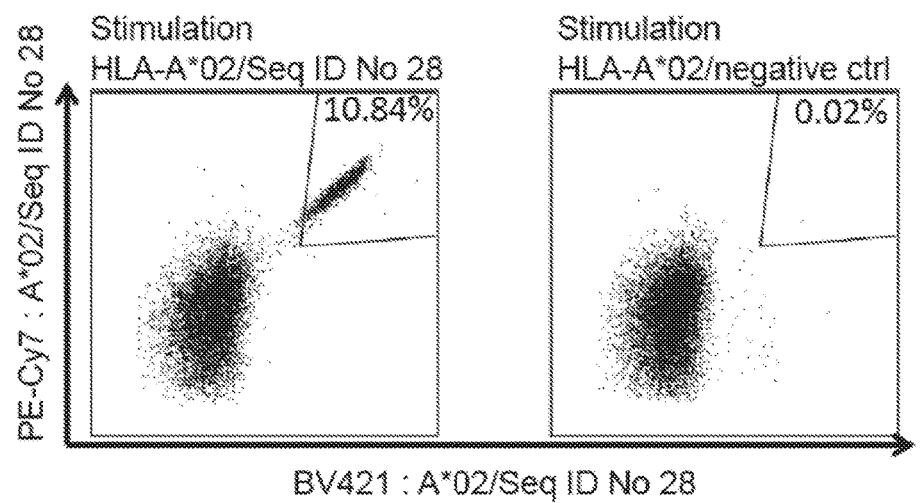
Figure 4C:
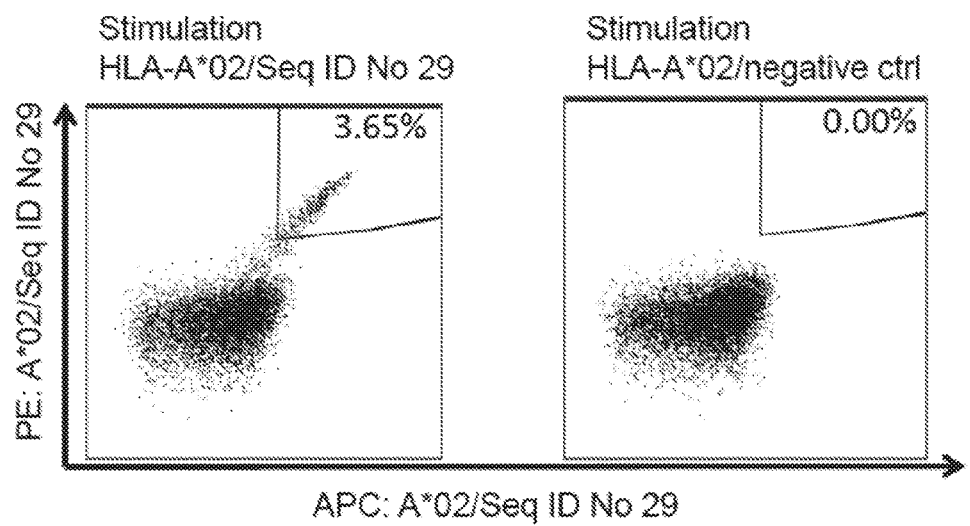

For tested HLA class I peptides, in vitro immunogenicity could be demonstrated by generation of peptide specific T-cell lines. Exemplary flow cytometry results after TUMAP-specific multimer staining for 2 peptides of the invention are shown in FIGS. 3A and 3B together with corresponding negative controls. Additional exemplary flow cytometry results after TUMAP-specific multimer staining for 3 peptides of the invention are shown in FIGS. 4A-4C together with corresponding negative controls. Results for 17 peptides from the invention are summarized in Table 10A. Additional results for 17 peptides from the invention are summarized in Table 10B.

TABLE 10A in vitro immunogenicity of HLA class I peptides of the invention

| Seq ID No | Peptide Code | Sequence | Wells | Donors |
|---|---|---|---|---|
| 98 | RAD54B-001 | SLYKGLLSV | ++ | ++++ |
| 101 | C4orf36-001 | GLLPSAESIKL | + | ++++ |
| 105 | KRT-010 | STYGGGLSV | + | ++++ |
| 108 | KRT5-001 | SLYNLGGSKRISI | + | ++++ |
| 109 | IGF2BP3-001 | KIQEILTQV | + | +++ |
| 113 | PKP1-002 | NLMASQPQL | +++ | ++++ |
| 114 | TP6-001 | VLVPYEPPQV | + | ++++ |
| 118 | KRT-006 | TLLQEQGTKTV | + | ++ |
| 123 | GJB5-001 | LLSGDLIFL | ++ | ++++ |
| 127 | FHL2-001 | SLFGKKYIL | ++ | ++++ |
| 135 | DNMT3B-001 | GLFSQHFNL | + | ++ |
| 137 | LOC-002 | GLAPFLLNAV | + | ++++ |
| 143 | FAP-003 | YVYQNNIYL | + | ++ |
| 145 | TMEM222-001 | LLYGKYVSV | ++ | ++++ |
| 147 | DNMT1-001 | ILMDPSPEYA | +++ | ++++ |
| 150 | NLRP2-001 | ILAEEPIYIRV | +++ | ++++ |
| 154 | BDH1-001 | KMWEELPEVV | + | ++++ |

Exemplary results of in vitro immunogenicity experiments conducted by the applicant for the peptides of the invention. <20% = +; 20%-49% = ++; 50%-69% = +++; >=70% = ++++

TABLE 10B

In vitro immunogenicity of HLA class I peptides of the invention

| SEQ ID No | Sequence | Wells positive [%] |
|---|---|---|
| 1 | GLAGGFGGPGFPV | + |
| 3 | SLYGLGGSKRISI | + |
| 8 | AQLNIGNVLPV | + |
| 10 | TLWPATPPKA | + |
| 11 | VLFSSPPVI | ++ |
| 12 | TLTDEINFL | + |
| 13 | SLVSYLDKV | ++ |
| 16 | ALKDSVQRA | + |
| 17 | SIWPALTQV | ++++ |
| 18 | YLYPDLSRL | + |
| 19 | ALAKLLPLL | ++ |
| 20 | YLINEIDRIRA | + |
| 26 | TLVDENQSWYL | ++ |
| 28 | AVDPVSGSLYV | +++ |
| 29 | RLLPDLDEV | ++ |

TABLE 10B-continued

In vitro immunogenicity of HLA class I peptides of the invention

| SEQ ID No | Sequence | Wells positive [%] |
|---|---|---|
| 30 | TLASLGYAVV | +++ |
| 82 | VLDINDNPPV | + |

Exemplary results of in vitro immunogenicity experiments conducted by the applicant for HLA-A*02 restricted peptides of the invention.
Results of in vitro immunogenicity experiments are indicated.
Percentage of positive wells and donors (among evaluable) are summarized as indicated <20% = +; 20%-49% = ++; 50%-69% = +++; >=70% = ++++

Example 4

Synthesis of Peptides

All peptides were synthesized using standard and well-established solid phase peptide synthesis using the Fmoc-strategy. Identity and purity of each individual peptide have been determined by mass spectrometry and analytical RP-HPLC. The peptides were obtained as white to off-white lyophilizes (trifluoro acetate salt) in purities of >50%. All TUMAPs are preferably administered as trifluoro-acetate salts or acetate salts, other salt-forms are also possible.

Example 5

MHC Binding Assays

Candidate peptides for T cell based therapies according to the present invention were further tested for their MHC binding capacity (affinity). The individual peptide-MHC complexes were produced by UV-ligand exchange, where a UV-sensitive peptide is cleaved upon UV-irradiation, and exchanged with the peptide of interest as analyzed. Only peptide candidates that can effectively bind and stabilize the peptide-receptive MHC molecules prevent dissociation of the MHC complexes. To determine the yield of the exchange reaction, an ELISA was performed based on the detection of the light chain (μ2m) of stabilized MHC complexes. The assay was performed as generally described in Rodenko et al. (Rodenko et al., 2006).

96 well MAXISorp plates (NUNC) were coated over night with 2 ug/ml streptavidin in PBS at room temperature, washed 4× and blocked for 1 h at 37° C. in 2% BSA containing blocking buffer. Refolded HLA-A*02:01/MLA-001 monomers served as standards, covering the range of 15-500 ng/ml. Peptide-MHC monomers of the UV-exchange reaction were diluted 100-fold in blocking buffer. Samples were incubated for 1 h at 37° C., washed four times, incubated with 2 ug/ml HRP conjugated anti-μ2m for 1h at 37° C., washed again and detected with TMB solution that is stopped with $NH_2SO_4$. Absorption was measured at 450 nm. Candidate peptides that show a high exchange yield (preferably higher than 50%, most preferred higher than 75%) are generally preferred for a generation and production of antibodies or fragments thereof, and/or T cell receptors or fragments thereof, as they show sufficient avidity to the MHC molecules and prevent dissociation of the MHC complexes.

TABLE 11

MHC class I binding scores.

| SEQ ID No | Sequence | Peptide exchange |
|---|---|---|
| 1 | GLAGGFGGPGFPV | ++++ |
| 2 | PVCPPGGIQEV | +++ |
| 3 | SLYGLGGSKRISI | +++ |
| 4 | ILDINDNPPV | +++ |
| 5 | VCPPGGIQEV | +++ |
| 6 | ALYDAELSQM | +++ |
| 7 | ALEEANADLEV | +++ |
| 8 | AQLNIGNVLPV | ++++ |
| 9 | STASAITPSV | ++ |
| 10 | TLWPATPPKA | +++ |
| 11 | VLFSSPPVI | ++++ |
| 12 | TLTDEINFL | ++++ |
| 13 | SLVSYLDKV | ++++ |
| 14 | RIMEGIPTV | ++++ |
| 15 | SMLNNIINL | +++ |
| 16 | ALKDSVQRA | +++ |
| 17 | SIWPALTQV | ++++ |
| 18 | YLYPDLSRL | ++++ |
| 19 | ALAKLLPLL | ++++ |
| 20 | YLINEIDRIRA | ++++ |
| 21 | FLHEPFSSV | ++++ |
| 22 | KLPEPCPSTV | +++ |
| 23 | SLPESGLLSV | +++ |
| 24 | LLIAINPQV | ++++ |
| 25 | SLCPPGGIQEV | ++++ |
| 26 | TLVDENQSWYL | +++ |
| 27 | YLAEPQWAV | ++++ |
| 28 | AVDPVSGSLYV | ++++ |
| 29 | RLLPDLDEV | ++++ |
| 30 | TLASLGYAVV | +++ |
| 31 | HLATVKLLV | ++++ |
| 32 | IQDAEGAIHEV | ++++ |
| 33 | AIYEGVGWNV | ++++ |
| 34 | ALDTFSVQV | ++++ |
| 35 | ALVGDVILTV | ++++ |
| 36 | GLWSSIFSL | ++++ |
| 37 | ILLEDVFQL | ++++ |
| 38 | KLLPGVQYV | ++++ |
| 39 | LLPEDDTRDNV | +++ |
| 40 | LLTPLNLQI | +++ |
| 41 | RLNGEGVGQVNISV | ++ |
| 42 | ALYTSGHLL | ++++ |
| 43 | AVLGGKLYV | ++++ |
| 44 | GLGDDSFPI | ++++ |
| 45 | GLIEWLENTV | ++++ |
| 46 | GLISSIEAQL | ++++ |
| 47 | QLLEGELETL | +++ |
| 48 | YLLDYPNNL | +++ |
| 49 | YLWEAHTNI | ++++ |
| 50 | ALSNVVHKV | ++++ |
| 51 | FLIPSIIFA | ++++ |
| 52 | LLFTGLVSGV | +++ |
| 53 | RLVEVGGDVQL | ++++ |
| 54 | RLSGEGVGPV | +++ |
| 55 | VLNVGVAEV | +++ |
| 56 | FLQLETEQV | ++++ |
| 57 | AILGFALSEA | ++++ |
| 58 | SLSDIQPCL | +++ |
| 59 | YLQNEVFGL | +++ |
| 60 | SLGNFKDDLL | +++ |
| 61 | FVAGYIAGV | ++++ |
| 62 | ILSSACYTV | ++++ |
| 63 | ALMDEINFMKM | ++++ |
| 64 | KILEJLFVJL | +++ |
| 65 | ALWGFFPVLL | ++++ |
| 66 | TLLSEIAEL | ++++ |
| 67 | AQLNLIWQL | ++++ |
| 68 | KILEMDDPRA | ++ |
| 69 | YVMESMTYL | ++++ |
| 70 | FLFPAFLTA | ++++ |
| 71 | SLFPYVVLI | ++++ |
| 72 | SLDGNPLAV | ++++ |
| 73 | YIDPYKLLPL | +++ |
| 74 | SLTSFLISL | +++ |
| 75 | ALASAPTSV | ++++ |
| 76 | ILFDEVLTFA | ++++ |
| 77 | SLRAFLMPI | ++ |
| 78 | VLYGDVEEL | +++ |

TABLE 11-continued

MHC class I binding scores.

| SEQ ID No | Sequence | Peptide exchange |
|---|---|---|
| 79 | GLHQDFPSVVL | +++ |
| 80 | GLYGIKDDVFL | ++++ |
| 81 | VLAENPDIFAV | +++ |
| 82 | VLDINDNPPV | +++ |
| 83 | QLLQYVYNL | ++++ |
| 84 | ALMAGCIQEA | ++++ |
| 85 | QLIEKITQV | +++ |
| 86 | SLQERQVFL | +++ |
| 87 | ALPEPSPAA | +++ |
| 88 | LMAPAPSTV | +++ |
| 89 | VLDEGLTSV | ++++ |
| 90 | TLNDGVVVQV | ++++ |
| 91 | MLFENMGAYTV | ++++ |

Binding of HLA-class I restricted peptides to HLA-A*02:01 was ranged by peptide exchange yield: >10% = +; >20% = ++; >50 = +++; >75% = ++++

REFERENCE LIST

Abdel-Ghany, M. et al., J Biol Chem 276 (2001): 25438-25446
Abdelmagid, S. A. et al., J Cell Biochem. 112 (2011): 1084-1092
Adhikary, G. et al., PLoS.One. 8 (2013): e84324
Aguiar, R. C. et al., J Biol Chem 280 (2005): 33756-33765
Ahmed, N. et al., Biol Chem 397 (2016): 1265-1276
Ai, R. et al., Gene Expr. 11 (2003): 35-45
Aisa, Y. et al., Int.J Hematol. 82 (2005): 266-269
Aizawa, S. et al., J Oral Sci. 56 (2014): 209-214
Akbari, M. R. et al., Hum. Genet. 129 (2011): 573-582
Akhtar, Ali M. et al., Proc. Natl. Acad. Sci. U.S.A 112 (2015): 7743-7748
Albergaria, A. et al., Int. J Dev. Biol 55 (2011): 811-822
Allison, J. P. et al., Science 270 (1995): 932-933
Alrawi, S. J. et al., Anticancer Res 26 (2006): 107-119
Ammendola, M. et al., Biomed. Res Int. 2014 (2014): 154702
Andersen, R. S. et al., Nat. Protoc. 7 (2012): 891-902
Andersson, L., Cold Spring Harb.Symp.Quant.Biol 74 (2009): 319-325
Andersson, L. et al., Transcription. 1 (2010): 144-148
Annibaldi, A. et al., PLoS.One. 6 (2011): e29024
Apostolopoulou, M. et al., PLoS.One. 7 (2012): e33289
Appay, V. et al., Eur.J Immunol. 36 (2006): 1805-1814
Arif, Q. et al., Arch.Pathol.Lab Med. 139 (2015): 978-980
Attallah, A. M. et al., Tumour.Biol 36 (2015): 7667-7674
Baak, J. P. et al., J Clin Pathol. 59 (2006): 1017-1028
Bachmann, S. B. et al., Mol Cancer 13 (2014): 125
Baglo, Y. et al., PLoS.One. 8 (2013): e65200
Bailey, C. M. et al., J Cell Physiol 209 (2006): 617-624
Balakrishnan, A. et al., Genes Chromosomes.Cancer 45 (2006): 883-892
Baluchamy, S. et al., In Vitro Cell Dev.Biol Anim 46 (2010): 718-725
Banchereau, J. et al., Cell 106 (2001): 271-274
Bao, L. et al., Cell Biol Toxicol. 32 (2016): 419-435
Bar-Shavit, R. et al., Methods Cell Biol 132 (2016): 341-358
Barach, Y. S. et al., Trends Mol.Med 17 (2011): 47-55
Barilli, A. et al., J Leukoc.Biol 90 (2011): 293-303
Barry, G. S. et al., Oncotarget. 7 (2016): 18953-18964
Bauml, J. M. et al., Ther.Adv.Med.Oncol 8 (2016): 168-175
Bausch, D. et al., Clin Cancer Res 17 (2011): 302-309
Beatty, G. et al., J Immunol 166 (2001): 2276-2282
Beggs, J. D., Nature 275 (1978): 104-109
Benjamini, Y. et al., Journal of the Royal Statistical Society.Series B (Methodological), Vol. 57 (1995): 289-300
Benzon, B. et al., Prostate Cancer Prostatic. Dis. (2016)
Binai, N. A. et al., Endocrine. 44 (2013): 496-503
Blanckaert, V. et al., Int.J Oncol 46 (2015): 2649-2655
Bongiovanni, L. et al., Vet.Dermatol. 25 (2014): 138-140
Bonitsis, N. et al., Exp.Oncol 28 (2006): 187-193
Bottino, C. et al., Front Immunol. 5 (2014): 56
Bouameur, J. E. et al., J Invest Dermatol. 134 (2014): 885-894
Boulter, J. M. et al., Protein Eng 16 (2003): 707-711
Boyero, L. et al., Int.J Med Sci. 10 (2013): 1166-1173
Braumuller, H. et al., Nature (2013)
Brendle, A. et al., Carcinogenesis 29 (2008): 1394-1399
Broderick, P. et al., Cancer Res 69 (2009): 6633-6641
Brosens, R. P. et al., J Pathol. 221 (2010): 411-424
Brossart, P. et al., Blood 90 (1997): 1594-1599
Bruckdorfer, T. et al., Curr. Pharm. Biotechnol. 5 (2004): 29-43
Bruna, F. et al., Stem Cell Res 18 (2017): 5-13
Bryan, R. T., Philos. Trans. R Soc. Lond B Biol Sci. 370 (2015): 20140042
Bryan, R. T. et al., J Urol. 184 (2010): 423-431
Bu, W. et al., Oncogene 30 (2011): 4399-4409
Bustin, S. A. et al., DNA Cell Biol 20 (2001): 331-338
Buttner, S. et al., EMBO J 30 (2011): 2779-2792
Cada, Z. et al., Histol. Histopathol. 24 (2009): 41-48
Camicia, R. et al., J Cell Sci. 126 (2013): 1969-1980
Camicia, R. et al., Mol. Cancer 14 (2015): 207
Campione, E. et al., Drug Des Devel.Ther. 9 (2015): 5843-5850
Camps, J. et al., Cancer Res 73 (2013): 2003-2013
Canto, I. et al., Mini.Rev Med Chem 12 (2012): 804-811
Card, K. F. et al., Cancer Immunol Immunother. 53 (2004): 345-357
Cazier, J. B. et al., Nat Commun. 5 (2014): 3756
Chang, H. H. et al., Cancer 117 (2011): 353-360
Chanock, S. J. et al., Hum. Immunol. 65 (2004): 1211-1223
Chanthammachat, P. et al., Arch. Oral Biol 58 (2013): 1677-1685
Chen, J. et al., Int. J Clin Exp. Pathol. 8 (2015): 2026-2032
Chen, L. et al., Oncotarget. (2016)
Chen, Q. et al., PLoS.One. 9 (2014): e88386
Chien, A. J. et al., Breast Cancer Res Treat. 155 (2016): 521-530
Choi, J. R. et al., Ann. Occup. Environ. Med 28 (2016): 13
Choi, Y. K. et al., Cancer Genomics Proteomics. 10 (2013): 265-275
Chowdhury, R. et al., Nature 510 (2014): 422-426
Chuang, J. J. et al., Toxicol. Appl. Pharmacol. 279 (2014): 322-330
Chung, T. K. et al., Int. J Cancer 137 (2015): 776-783
Cipolat, S. et al., Elife. 3 (2014): e01888
Clark, D. L. et al., J Anim Sci. 93 (2015): 2546-2558
Cohen, C. J. et al., J Mol Recognit. 16 (2003a): 324-332
Cohen, C. J. et al., J Immunol 170 (2003b): 4349-4361
Cohen, S. N. et al., Proc. Natl. Acad. Sci. U.S.A 69 (1972): 2110-2114
Coligan, J. E. et al., Current Protocols in Protein Science (1995)
Colombetti, S. et al., J Immunol. 176 (2006): 2730-2738
Corsaro, A. et al., Oncotarget. 7 (2016): 38638-38657
D'Asti, E. et al., Semin. Thromb. Hemost. 40 (2014): 284-295
Das, M. et al., PLoS. One. 8 (2013): e69607
Das, M. et al., Tumour. Biol 36 (2015): 9987-9994
David, G. et al., Oncogene 25 (2006): 7354-7360

Davies, E. L. et al., Eur. J Cancer 35 (1999): 902-907
Delgado, A. P. et al., Cancer Genomics Proteomics. 11 (2014): 201-213
Deng, M. et al., J Biol Chem 284 (2009): 7875-7888
Deng, W. et al., Cell Physiol Biochem. 35 (2015): 1677-1688
Deng, Y. et al., Cancer Invest 31 (2013): 97-102
Dengjel, J. et al., Clin Cancer Res 12 (2006): 4163-4170
Denkberg, G. et al., J Immunol 171 (2003): 2197-2207
Depianto, D. et al., Nat Genet. 42 (2010): 910-914
Dewar, R. et al., Arch. Pathol. Lab Med 135 (2011): 422-429
do Prado, R. F. et al., Oral Surg. Oral Med Oral Pathol. Oral Radiol. Endod. 104 (2007): e40-e44
Dorn, J. et al., Oncol Lett. 9 (2015): 418-424
Dotlic, S. et al., Appl. Immunohistochem. Mol. Morphol. 22 (2014): 537-542
Dou, N. et al., Am. J Cancer Res 6 (2016): 2641-2650
Drucker, K. L. et al., BMC. Cancer 15 (2015): 565
Du, L. et al., Cancer Res 73 (2013): 2682-2694
Dubash, A. D. et al., J Cell Biol 202 (2013): 653-666
Duggan, M. A., Gan To Kagaku Ryoho 29 Suppl 1 (2002): 176-193
Economopoulou, P. et al., Ann. Transl. Med. 4 (2016): 173
Eichler, T. E. et al., Kidney Int. 90 (2016): 568-579
El-Rifai, W. et al., Cancer Res 62 (2002): 6823-6826
Elste, A. P. et al., J Mol. Histol. 41 (2010): 89-99
Epp, N. et al., J Cell Biol 177 (2007): 173-182
Er, T. K. et al., J Mol. Med. (Berl) (2016)
Esteban-Jurado, C. et al., Eur. J Hum. Genet. 24 (2016): 1501-1505
Ettl, T. et al., Clin Exp. Med (2016)
Evangelista, M. T. et al., J Cutan. Pathol. 42 (2015): 824-831
Falk, K. et al., Nature 351 (1991): 290-296
Fan, J. et al., Clin Cancer Res 17 (2011): 2908-2918
Fang, W. K. et al., Asian Pac. J Cancer Prev. 15 (2014): 871-876
Fang, W. Y. et al., Acta Biochim. Biophys. Sin. (Shanghai) 37 (2005): 541-546
Fauci, J. M. et al., Gynecol. Oncol 127 (2012): 420-425
Fevre-Montange, M. et al., Int. J Oncol 35 (2009): 1395-1407
Fijneman, R. J. et al., Clin Cancer Res 18 (2012): 2613-2624
Fong, L. et al., Proc. Natl. Acad. Sci. U.S.A 98 (2001): 8809-8814
French, J. et al., Histochem. J 34 (2002): 223-231
Frohwitter, G. et al., Oncol Lett. 12 (2016): 107-113
Funakoshi-Tago, M., Yakugaku Zasshi 132 (2012): 1267-1272
Furstenberger, G. et al., Prostaglandins Other Lipid Mediat. 82 (2007): 128-134
Gabrilovich, D. I. et al., Nat Med. 2 (1996): 1096-1103
Galoian, K. et al., Mol. Clin Oncol 3 (2015): 171-178
Gandhi, C. R. et al., Gastroenterology 148 (2015): 379-391
Gao, W. et al., BMC. Cancer 15 (2015): 367
Gao, Y. et al., Di Yi. Jun. Yi. Da. Xue. Xue. Bao. 23 (2003): 885-887
Gao, Y. B. et al., Nat Genet. 46 (2014): 1097-1102
Gattinoni, L. et al., Nat Rev. Immunol 6 (2006): 383-393
Gazda, H. T. et al., Hum. Mutat. 33 (2012): 1037-1044
Ge, W. et al., Nat Chem Biol 8 (2012): 960-962
Gelfand, R. et al., Int.J Oncol 50 (2017): 49-65
Gemmill, R. M. et al., Cancer Lett. 300 (2011): 66-78
Gieseler, F. et al., Cell Commun. Signal. 11 (2013): 86
Giguere, A. et al., Cancer Genet. Cytogenet. 202 (2010): 94-100
Gnjatic, S. et al., Proc Natl Acad. Sci. U.S.A 100 (2003): 8862-8867
Godkin, A. et al., Int. Immunol 9 (1997): 905-911
Gomez-Morales, M. et al., Histopathology 63 (2013): 103-113
Gorski, J. J. et al., Breast Cancer Res Treat. 122 (2010): 721-731
Green, M. R. et al., Molecular Cloning, A Laboratory Manual 4th (2012)
Greenfield, E. A., Antibodies: A Laboratory Manual 2nd (2014)
Grin, A. et al., Hum. Pathol. 46 (2015): 541-548
Grosset, A. A. et al., BMC. Cancer 14 (2014): 801
Grosset, A. A. et al., PLoS. One. 11 (2016): e0166731
Gruber, A. D. et al., Cancer Res 59 (1999): 5488-5491
Gupta, S. K. et al., Innate. Immun. 19 (2013): 86-97
Haass, N. K. et al., Pigment Cell Res 18 (2005): 150-159
Hammam, O. et al., J Egypt. Soc. Parasitol. 44 (2014): 733-740
Harris, T. M. et al., Arch. Pathol. Lab Med. 139 (2015): 494-507
Hatina, J. et al., Neoplasma 59 (2012): 728-736
Hatta, M. et al., J Obstet. Gynaecol. Res 30 (2004): 53-58
Hayes, D. C. et al., Anticancer Res 26 (2006): 1567-1575
He, C. S. et al., Cell Physiol Biochem. 40 (2016): 1221-1229
He, X. et al., Int.J Biol Macromol. 72 (2015): 1081-1089
Heidenreich, B. et al., Curr. Opin. Genet. Dev. 24 (2014): 30-37
Heikinheimo, K. et al., J Dent. Res 86 (2007): 544-549
Heikinheimo, K. et al., J Dent. Res 94 (2015): 101-111
Herold-Mende, C. et al., Cell Tissue Res 306 (2001): 399-408
Higareda-Almaraz, J. C. et al., BMC. Cancer 16 (2016): 680
Hoadley, K. A. et al., PLoS. Med 13 (2016): e1002174
Honrado, E. et al., Crit Rev Oncol Hematol. 59 (2006): 27-39
Horiguchi, K. et al., Oncogene 31 (2012): 3190-3201
Hu, J. et al., Int.J Clin Exp. Pathol. 8 (2015): 9182-9188
Huang, Y. P. et al., Biomedicine. (Taipei) 6 (2016): 3
Huang, Y. Z. et al., Sci. Rep. 4 (2014): 4570
Huber, A. R. et al., BMC. Gastroenterol. 15 (2015): 80
Hwang, M. L. et al., J Immunol. 179 (2007): 5829-5838
Hwang, Y. S. et al., J Cancer Prev. 20 (2015): 121-128
Ida-Yonemochi, H. et al., Mod. Pathol. 25 (2012): 784-794
lino, I. et al., Cancer Sci. 104 (2013): 624-630
Inamura, K. et al., Lung Cancer 103 (2017): 44-51
Ioana, M. et al., J Gastrointestin. Liver Dis. 19 (2010): 155-159
Iorns, E. et al., Breast Cancer Res Treat. 135 (2012): 79-91
Ishii, H. et al., J Biol Chem 289 (2014): 27386-27399
Ishimi, Y. et al., J Biochem. 157 (2015): 561-569
Janakiram, M. et al., Discov Med 14 (2012): 229-236
Janakiram, M. et al., Immunotherapy 8 (2016): 809-819
Jiang, L. et al., PLoS. One. 9 (2014): e94187
Jiang, M. M. et al., Zhongguo Shi Yan. Xue. Ye. Xue. Za Zhi. 21 (2013): 821-829
Jiang, R. et al., J Biol Chem 286 (2011): 9127-9135
Jiang, Y. et al., Oncol Lett. 10 (2015): 3826-3831
Johnson, R. H. et al., Oncotarget. (2015)
Joosse, S. A. et al., Clin Cancer Res 18 (2012): 993-1003
Jung, G. et al., Proc Natl Acad Sci USA 84 (1987): 4611-4615
Jurcic, V. et al., Histol.Histopathol. 30 (2015): 945-953
Juszczynski, P. et al., Mol. Cell Biol 26 (2006): 5348-5359
Kakuda, D. K. et al., Biochim. Biophys. Acta 1414 (1998): 75-84
Kan, T. et al., Oncology 70 (2006): 25-33
Kaplun, A. et al., Crit Rev Eukaryot. Gene Expr. 22 (2012): 249-258

Kasthuri, R. S. et al., J Clin Oncol 27 (2009): 4834-4838
Katada, K. et al., J Proteomics. 75 (2012): 1803-1815
Katoh, M., Int.J Oncol 41 (2012): 1913-1918
Kawakami, K. et al., Int. J Oncol (2015)
Kaz, A. M. et al., Genes Chromosomes. Cancer 51 (2012): 384-393
Kedde, M. et al., Cell Cycle 7 (2008): 899-903
Kettunen, E. et al., Cancer Genet. Cytogenet. 149 (2004): 98-106
Kibbe, A. H., Handbook of Pharmaceutical Excipients rd (2000)
Kim, H. J. et al., Anticancer Res 33 (2013): 1555-1561
Kim, K. et al., Int.J Colorectal Dis. 23 (2008a): 569-580
Kim, K. H. et al., Nucleic Acids Res 43 (2015): 7462-7479
Kim, S. W. et al., Blood 111 (2008b): 1644-1653
Kim, T. W. et al., Oncotarget. (2016)
Kim, Y. H. et al., Ann. Surg. Oncol 18 (2011): 2338-2347
Kinyamu, H. K. et al., Mol. Carcinog 47 (2008): 845-885
Kishikawa, T. et al., Oncotarget. 6 (2015): 8339-8352
Kitchen, M. O. et al., Epigenetics. 11 (2016): 237-246
Klawitter, J. et al., Breast Cancer Res 12 (2010): R16
Knudsen, K. A. et al., J Cell Biochem. 95 (2005): 488-496
Koba, S. et al., Am. J Dermatopathol. 37 (2015): e31-e36
Kobos, R. et al., J Pathol. 229 (2013): 743-754
Koc, E. C. et al., Mitochondrion. 24 (2015): 113-121
Kocaturk, B. et al., Thromb. Res 129 Suppl 1 (2012): S69-S75
Kocaturk, B. et al., J Thromb. Haemost. 11 Suppl 1 (2013): 285-293
Kohn, K. W. et al., PLoS.One. 9 (2014): e99269
Kolin, D. L. et al., Biol Chem 395 (2014): 1087-1093
Koringa, P. G. et al., Vet. Comp Oncol (2013)
Krepischi, A. C. et al., Breast Cancer Res 14 (2012): R24
Krieg, A. M., Nat Rev. Drug Discov. 5 (2006): 471-484
Kwok, H. F. et al., Am. J Cancer Res 5 (2015): 52-71
Kwon, J. et al., Int J Oncol 43 (2013): 1523-1530
Labrie, M. et al., PLoS.One. 10 (2015): e0131307
Labrie, M. et al., Oncotarget. 5 (2014): 7705-7721
Lee, D. J. et al., Cancer Biol Ther. 10 (2010): 689-693
Lee, D. M. et al., Environ. Toxicol. Pharmacol. 34 (2012): 858-868
Lee, J. Y. et al., Carcinogenesis 30 (2009): 1528-1531
Lee, K. Y. et al., J Med. 35 (2004): 141-149
Leiserson, M. D. et al., Genome Biol 16 (2015): 160
Leiserson, M. D. et al., Genome Biol 17 (2016): 168
Leung, F. et al., Cancer Epidemiol. Biomarkers Prev. 25 (2016): 1333-1340
Leung, J. et al., Immune. Netw. 14 (2014): 265-276
Lexander, H. et al., Anal. Quant. Cytol. Histol. 27 (2005): 263-272
Li, J. et al., Chin Med J (Engl.) 122 (2009): 486-495
Li, J. Z. et al., Chin Med. J (Engl.) 121 (2008): 1882-1890
Li, L. et al., Asian Pac. J Cancer Prev. 13 (2012a): 3265-3270
Li, T. et al., Exp. Dermatol. 24 (2015): 342-348
Li, W. Q. et al., Carcinogenesis 34 (2013): 1536-1542
Li, X. et al., Oncogene 23 (2004): 1474-1480
Li, X. et al., Biochem. Biophys. Res Commun. 419 (2012b): 148-153
Li, Y. et al., J Cell Physiol 212 (2007): 675-681
Lian, M. et al., PLoS. One. 8 (2013): e84854
Liddy, N. et al., Nat Med. 18 (2012): 980-987
Lim, L. C. et al., Pathol. Oncol Res 22 (2016): 169-177
Lima, L. G. et al., Biosci. Rep. 33 (2013)
Lin, C. S. et al., Cancer Lett. 368 (2015): 36-45
Lin, H. S. et al., Arch. Otolaryngol. Head Neck Surg. 130 (2004): 311-316
Lion, M. et al., Cell Cycle 12 (2013): 1211-1224
Liu, C. L. et al., Eur. Rev Med Pharmacol. Sci. 20 (2016): 4466-4473
Liu, D. Q. et al., Sci. Rep. 5 (2015): 11955
Liu, J. et al., J Biochem. 148 (2010): 659-667
Liu, Y. et al., Oncol Rep. 18 (2007): 943-951
Ljunggren, H. G. et al., J Exp. Med. 162 (1985): 1745-1759
Llorente, A. et al., J Cell Sci. 117 (2004): 5343-5351
Lo, W. Y. et al., J Proteomics. 77 (2012): 154-166
Lonardo, F. et al., Curr. Pharm. Des 16 (2010): 1877-1881
Longenecker, B. M. et al., Ann N.Y. Acad. Sci. 690 (1993): 276-291
Lonsdale, J., Nat. Genet. 45 (2013): 580-585
Loos, M. et al., Clin Dev. Immunol. 2010 (2010): 683875
Low, K. C. et al., Trends Biochem. Sci. 38 (2013): 426-434
Lu, J. J. et al., Chin J Nat Med. 13 (2015a): 673-679
Lu, Y. et al., BMC. Mol. Biol 16 (2015b): 21
Lu, Y. et al., PLoS.One. 8 (2013): e73866
Lubben, B. et al., J Biol Chem 270 (1995): 11549-11554
Lucito, R. et al., Cancer Biol Ther. 6 (2007): 1592-1599
Lukas, T. J. et al., Proc. Natl. Acad. Sci. U.S.A 78 (1981): 2791-2795
Lundblad, R. L., Chemical Reagents for Protein Modification 3rd (2004)
Luo, D. et al., Biochem. Biophys. Res Commun. (2016)
Maass, N. et al., Acta Oncol 39 (2000): 931-934
Maerki, S. et al., J Cell Biol 187 (2009): 791-800
Man, Y. et al., Tohoku J Exp. Med 234 (2014): 29-40
Mange, A. et al., J Proteomics. 142 (2016): 114-121
Marech, I. et al., World J Gastroenterol. 20 (2014): 8910-8920
Marioni, G. et al., Acta Otolaryngol. 129 (2009): 476-480
Markljung, E. et al., PLoS. Biol 7 (2009): e1000256
Marshall, P. A. et al., J Steroid Biochem. Mol. Biol 132 (2012): 147-159
Martinez, O. et al., PLoS. One. 5 (2010): e10398
Masugi, Y. et al., Lab Invest 95 (2015): 308-319
Matin, S. F. et al., Urol. Oncol 32 (2014): 309-316
Matsumoto, K. et al., Biomed.Res 35 (2014): 201-206
Matsuzaka, K. et al., Bull. Tokyo Dent. Coll. 45 (2004): 229-233
McDoniels-Silvers, A. L. et al., Clin Cancer Res 8 (2002): 1127-1138
Mei, Z. Z. et al., J Biol Chem 291 (2016): 18176-18189
Melaiu, O. et al., Mutat. Res 771 (2015): 6-12
Meschenmoser, K. et al., In Vivo 27 (2013): 431-442
Meslin, F. et al., Cancer Res 67 (2007): 10910-10919
Messina, M. et al., Blood 123 (2014): 2378-2388
Meziere, C. et al., J Immunol 159 (1997): 3230-3237
Min, L. et al., Histopathology 67 (2015): 677-688
Misago, N. et al., J Dermatol. 43 (2016): 439-442
Mitchell, S. M. et al., BMC. Cancer 14 (2014): 54
Mlacki, M. et al., PLoS. One. 9 (2014): e89247
Morgan, P. R. et al., Eur. J Cancer B Oral Oncol 30B (1994): 160-166
Morgan, R. A. et al., Science 314 (2006): 126-129
Mori, M. et al., Transplantation 64 (1997): 1017-1027
Morris, L. G. et al., Nat Genet. 45 (2013): 253-261
Morris, M. R. et al., Oncogene 30 (2011): 1390-1401
Mortara, L. et al., Clin Cancer Res. 12 (2006): 3435-3443
Moskvina, L. V. et al., Arkh. Patol. 72 (2010): 58-61
Mountzios, G. et al., Ann. Oncol 25 (2014): 1889-1900
Mueller, L. N. et al., J Proteome. Res 7 (2008): 51-61
Mueller, L. N. et al., Proteomics. 7 (2007): 3470-3480
Mumberg, D. et al., Proc. Natl. Acad. Sci. U.S.A 96 (1999): 8633-8638
Muramatsu, T. et al., Oral Oncol 39 (2003): 199-203

Mussai, F. et al., Blood 125 (2015): 2386-2396
Myklebust, M. P. et al., Br. J Cancer 106 (2012): 756-762
Naeem, A. S. et al., Cell Death. Differ. 22 (2015): 2123-2132
Nagappan, A. et al., BMC. Biochem. 14 (2013): 24
Nagata, M. et al., PLoS. One. 9 (2014): e93164
Narayanan, B. A., Curr. Cancer Drug Targets. 6 (2006): 711-727
Narisawa, Y. et al., J Dermatol. 42 (2015): 445-452
National Cancer Institute, (5-6-2015), www.cancer.gov
Natsuga, K. et al., J Invest Dermatol. (2015)
Natsuga, K. et al., J Invest Dermatol. 136 (2016): 99-106
Neumann, M. et al., Blood 121 (2013): 4749-4752
North, J. P. et al., Am. J Surg. Pathol. 39 (2015): 1347-1356
Novak, B. et al., Naunyn Schmiedebergs Arch. Pharmacol. 384 (2011): 583-602
Nygren, M. K. et al., Front Biosci. (Elite. Ed) 3 (2011): 989-993
Oehler, V. G. et al., Blood 114 (2009): 3292-3298
Oh, H. R. et al., Cell Oncol (Dordr.) 37 (2014): 455-461
Oi, N. et al., Oncogene 34 (2015): 2660-2671
Oikonomopoulou, K. et al., Biol Chem 391 (2010): 299-310
Ormanns, S. et al., Br. J Cancer 113 (2015): 1460-1466
Otsubo, T. et al., Cancer Med 4 (2015): 415-425
Palacios, J. et al., Pathobiology 75 (2008): 85-94
Papagerakis, S. et al., Hum. Pathol. 34 (2003): 565-572
Paparella, M. L. et al., J Oral Pathol. Med 44 (2015): 801-809
Paredes, J. et al., Breast Cancer Res 9 (2007): 214
Paredes, J. et al., Biochim. Biophys. Acta 1826 (2012): 297-311
Park, J. Y. et al., Oncotarget. 6 (2015a): 5342-5353
Park, Y. H. et al., Int.J Cancer 136 (2015b): 1976-1984
Pereira, P. M. et al., Org. Biomol. Chem. 12 (2014): 1804-1811
Perrin, C. et al., Am. J Dermatopathol. 33 (2011): 131-139
Persson, F. et al., Cancer Lett. 260 (2008): 37-47
Pickering, C. R. et al., Clin Cancer Res 20 (2014): 6582-6592
Pierce, A. et al., Mol. Cell Proteomics. 7 (2008): 853-863
Pigullo, S. et al., Pediatr. Blood Cancer 52 (2009): 376-378
Pinheiro, J. et al., nlme: Linear and Nonlinear Mixed Effects Models (http://CRAN.R-project.org/packe=nlme) (2015)
Piura, B. et al., Harefuah 144 (2005): 261-5, 303, 302
Plebanski, M. et al., Eur.J Immunol 25 (1995): 1783-1787
Poligone, B. et al., J Invest Dermatol. 135 (2015): 869-876
Polotskaia, A. et al., Proc. Natl. Acad. Sci. U.S.A 112 (2015): E1220-E1229
Pondugula, S. et al., Mol. Cell Biol 29 (2009): 4891-4905
Porta, C. et al., Virology 202 (1994): 949-955
Preisz, K. et al., Orv. Hetil. 148 (2007): 979-983
Probst, C. et al., Clin Chim. Acta 410 (2009): 13-18
Qiu, S. et al., Cancer Sci. (2016)
Qu, T. et al., Mol.Med Rep. 14 (2016): 5041-5048
Rafnar, T. et al., Cancer Res 71 (2011): 1356-1361
Ramakrishna, S. et al., PLoS.One. 7 (2012): e37772
Ramakrishna, S. et al., J Biol Chem 286 (2011): 10505-10514
Ramani, D. et al., Clin Nutr. 33 (2014): 14-22
Ramani, V. C. et al., BMC. Cancer 8 (2008): 373
Ramena, G. et al., PLoS.One. 11 (2016): e0147489
Rammensee, H. et al., Immunogenetics 50 (1999): 213-219
Rashid, R. et al., Mol. Cell 21 (2006): 249-260
Rastelli, F. et al., Tumori 96 (2010): 875-888
Ratovitski, E. A., FEBS Lett. 587 (2013): 3581-3586
RefSeq, The NCBI handbook [Internet], Chapter 18, (2002), www.ncbi.nlm.nih.gov/books/NBK21091/Remmelink, M. et al., Histopathology 58 (2011): 543-556
Resende, C. et al., *Helicobacter.* 16 Suppl 1 (2011): 38-44
Reyes, C. et al., Appl. Immunohistochem. Mol. Morphol. 21 (2013): 283-286
Ribeiro, A. S. et al., Front Oncol 4 (2014): 371
Riker, A. I. et al., BMC. Med Genomics 1 (2008): 13
Rini, B. I. et al., Cancer 107 (2006): 67-74
Rock, K. L. et al., Science 249 (1990): 918-921
Rohan, S. et al., Clin Cancer Res 12 (2006): 6937-6945
Rohrbeck, A. et al., PLoS. One. 4 (2009): e7315
Rooney, M. S. et al., Cell 160 (2015): 48-61
Rotmann, A. et al., Biochem. J 395 (2006): 117-123
Rotty, J. D. et al., J Cell Biol 197 (2012): 381-389
Ruf, W., Thromb. Res 130 Suppl 1 (2012): S84-S87
Ruf, W. et al., J Thromb. Haemost. 9 Suppl 1 (2011): 306-315
Rui, X. et al., Int. J Clin Exp. Pathol. 8 (2015): 5435-5442
Saaber, F. et al., Pathol. Res Pract. 211 (2015): 208-213
Sabeti, S. et al., Indian J Dermatol. 58 (2013): 331-336
Safadi, R. A. et al., Oral Surg. Oral Med. Oral Pathol. Oral Radiol. 121 (2016): 402-411
Sager, R. et al., Curr. Top. Microbiol. Immunol. 213 (Pt 1) (1996): 51-64
Saiki, R. K. et al., Science 239 (1988): 487-491
Salas, S. et al., Int.J Cancer 125 (2009): 851-860
Saletta, F. et al., BBA. Clin 1 (2014): 59-77
Sanchez-Palencia, A. et al., Int. J Cancer 129 (2011): 355-364
Sasaki, Y. et al., Cancer Biol Ther. 13 (2012): 1512-1521
Sato, T. et al., Oncogene 33 (2014): 2215-2224
Sauer, H. et al., Free Radic. Biol Med 27 (1999): 1276-1283
Sawada, K. et al., J Oral Sci. 58 (2016): 325-331
Schmitt-Graeff, A. et al., Histopathology 51 (2007): 87-97
Schrader, C. H. et al., Mol. Cancer 14 (2015): 107
Schulten, R. et al., Naunyn Schmiedebergs Arch. Pharmacol. 385 (2012): 969-979
Schumann, H. et al., Br. J Dermatol. 167 (2012): 929-936
Scola, N. et al., Br. J Dermatol. 167 (2012): 591-597
Seal, S. et al., Cancer Res 63 (2003): 8596-8599
Sedda, S. et al., World J Gastroenterol. 20 (2014): 11977-11984
Seeger, F. H. et al., Immunogenetics 49 (1999): 571-576
Seishima, M. et al., Arch. Dermatol. 140 (2004): 1500-1503
Sellheyer, K., J Cutan. Pathol. 42 (2015): 90-101
Sharifi, N. et al., Prostate 67 (2007): 301-311
Shen, M. et al., Environ. Mol. Mutagen 50 (2009): 285-290
Shen, X. et al., Tumour. Biol 36 (2015): 7133-7142
Sheng, S., Front Biosci. 9 (2004): 2733-2745
Sherman, F. et al., Laboratory Course Manual for Methods in Yeast Genetics (1986)
Shi, L. et al., BMC. Cancer 16 (2016): 815
Shim, J. H. et al., Cancer Prev. Res (Phila) 3 (2010): 670-679
Shimbo, T. et al., PLoS. One. 5 (2010): e10566
Shinmura, K. et al., Dis. Markers 2014 (2014): 619273
Shruthi, D. K. et al., J Oral Maxillofac. Pathol. 18 (2014): 365-371
Sidiropoulos, K. G. et al., Mol. Oncol 10 (2016): 993-1007
Silveira, A. C. et al., Cancer Lett. 276 (2009): 32-37
Singh-Jasuja, H. et al., Cancer Immunol. Immunother. 53 (2004): 187-195
Sinha, N. et al., Oral Oncol 49 (2013): 854-862
Sivanathan, L. et al., Prostate 74 (2014): 537-546
Sizemore, G. M. et al., J Biol Chem 289 (2014): 24102-24113
Skipworth, R. J. et al., Int. J Oncol 36 (2010): 973-982
Slaga, T. J. et al., Prog. Clin Biol Res 391 (1995): 1-20
Small, E. J. et al., J Clin Oncol. 24 (2006): 3089-3094

Smith, K. T. et al., Mol. Cell Proteomics. 11 (2012): 1815-1828
Sobolik-Delmaire, T. et al., Cell Commun. Adhes. 14 (2007): 99-109
Solus, J. F. et al., Int. J Surg. Pathol. 24 (2016): 29-36
Somasekharan, S. P. et al., J Cell Biol 208 (2015): 913-929
Song, B. et al., Exp. Ther. Med 12 (2016): 2455-2468
Soreide, K. et al., J Pathol. 209 (2006): 147-156
Southgate, J. et al., Histol. Histopathol. 14 (1999): 657-664
Sturm, M. et al., BMC. Bioinformatics. 9 (2008): 163
Sun, B. C. et al., Zhonghua Yi. Xue. Za Zhi. 86 (2006): 1808-1812
Sun, L. et al., Mol. Med Rep. 12 (2015a): 4266-4272
Sun, N. K. et al., Oncotarget. 6 (2015b): 27065-27082
Sun, S. et al., Gene 584 (2016): 90-96
Suzuki, A. et al., Cancer Sci. 99 (2008): 986-994
Swatler, J. et al., Postepy Hig. Med Dosw. (Online.) 70 (2016): 25-42
Swoboda, R. K. et al., Cancer Res 67 (2007): 3555-3559
Tai, G. et al., PLoS. One. 8 (2013): e81167
Taintor, A. R. et al., J Am. Acad. Dermatol. 56 (2007): S73-S76
Tamir, A. et al., J Ovarian. Res 7 (2014): 109
Tamm-Rosenstein, K. et al., PLoS. One. 8 (2013): e68907
Tang, B. et al., Oncotarget. 6 (2015a): 12723-12739
Tang, H. B. et al., Zhonghua Yi. Xue. Za Zhi. 88 (2008): 1553-1556
Tang, X. H. et al., Oncotarget. 6 (2015b): 24424-24435
Taniguchi, T. et al., Nat Med 9 (2003): 568-574
Taoka, Y. et al., Biomed. Res 36 (2015): 253-261
Tauber, S. et al., Mol. Cancer 9 (2010): 200
Teles, Alves, I et al., Oncogene 34 (2015): 568-577
Tennenbaum, T. et al., J Investig. Dermatol. Symp. Proc. 1 (1996): 157-161
Teo, C. R. et al., Cell Signal. 28 (2016): 1479-1488
Terada, T., Int.J Clin Exp.Pathol. 5 (2012): 596-600
Teufel, R. et al., Cell Mol Life Sci. 62 (2005): 1755-1762
Tian, S. Y. et al., Int.J Clin Exp.Pathol. 7 (2014): 3752-3762
Timar, J. et al., Clin Exp.Metastasis 27 (2010): 371-387
Tomlinson, R. L. et al., Mol.Biol Cell 19 (2008): 3793-3800
Tonoike, Y. et al., BMC.Cell Biol 12 (2011): 41
Tran, E. et al., Science 344 (2014): 641-645
Trojandt, S. et al., Hum.Immunol. 77 (2016): 1223-1231
Tsuji, A. B. et al., Biochem.Biophys.Res Commun. 333 (2005): 1370-1377
Tsutsui, M. et al., Int.J Oncol 47 (2015): 867-874
Ueda, S. et al., Cancer Res 64 (2004): 5672-5676
Vadie, N. et al., RNA.Biol 12 (2015): 893-899
Vakrakou, A. et al., Biol Chem 395 (2014): 1105-1117
Valletta, D. et al., Carcinogenesis 35 (2014): 1407-1415
Vanaja, D. K. et al., Cancer Res 63 (2003): 3877-3882
Vasca, V. et al., Oncol Lett. 8 (2014): 2501-2504
Vieira, A. F. et al., Mol. Cancer 14 (2015): 178
Vigneswaran, N. et al., Oral Maxillofac. Surg. Clin North Am. 26 (2014): 123-141
Vliet-Gregg, P. A. et al., Virology 478 (2015): 50-60
Volkmer, J. P. et al., Proc. Natl. Acad. Sci. U.S.A 109 (2012): 2078-2083
Walia, V. et al., Cancer Res 69 (2009): 6624-6632
Walia, V. et al., Oncogene 31 (2012): 2237-2246
Walter, S. et al., J Immunol 171 (2003): 4974-4978
Walter, S. et al., Nat Med. 18 (2012): 1254-1261
Wang, J. et al., Br. J Dermatol. 153 (2005): 558-564
Wang, L. et al., J Cutan. Pathol. 42 (2015a): 361-367
Wang, L. et al., Int. J Cancer 134 (2014a): 2764-2771
Wang, L. et al., Tumour. Biol 37 (2016a): 14939-14947
Wang, M. et al., Exp. Dermatol. 23 (2014b): 636-638
Wang, S. et al., Cytokine 86 (2016b): 110-118
Wang, X. et al., Oncotarget. 7 (2016c): 22911-22927
Wang, X. et al., Proc. Natl. Acad. Sci. U.S.A 110 (2013): 15997-16002
Wang, X. et al., Mol. Cell Biol 27 (2007): 3098-3108
Wang, X. et al., Eur.J Pharmacol. 768 (2015b): 116-122
Wang, X. et al., Sci. Rep. 6 (2016d): 19006
Wang, X. et al., Int. J Biol Markers 29 (2014c): e150-e159
Wang, Z. S. et al., Oncotarget. 7 (2016e): 44266-44276
Ward, A. M. et al., RNA. Biol 8 (2011): 1173-1186
Watanabe, T. et al., Cancer Cell Int. 10 (2010): 2
Wheler, J. J. et al., BMC. Cancer 15 (2015): 442
Willcox, B. E. et al., Protein Sci. 8 (1999): 2418-2423
Willers, I. M. et al., Biochim. Biophys. Acta 1807 (2011): 543-551
Williams, L. M. et al., Aquat. Toxicol. 180 (2016): 141-154
Willis, S. et al., Meta Gene 4 (2015): 129-141
Winslow, S. et al., Mol. Cancer 12 (2013): 156
Witte, D. et al., J Clin Med 5 (2016)
Wojtalewicz, N. et al., PLoS. One. 9 (2014): e90461
Wojtukiewicz, M. Z. et al., Cancer Metastasis Rev 34 (2015): 775-796
Wong, M. P. et al., Pathology 40 (2008): 611-616
World Health Organization, (2014), www.who.int/en/Wreesmann,
V. B. et al., ORL J Otorhinolaryngol. Relat Spec. 69 (2007): 218-225
Wu, S. et al., Oncotarget. (2016)
Xi, Y. et al., Monoclon. Antib. Immunodiagn. Immunother. 34 (2015): 346-353
Xie, C. et al., Sci. Rep. 6 (2016a): 27528
Xie, X. et al., Obesity. (Silver.Spring) 24 (2016b): 389-397
Xin, Z. et al., Virchows Arch. 465 (2014): 35-47
Xu, C. et al., PLoS. Genet. 9 (2013): e1003169
Xu, X. et al., Proteomics. 10 (2010): 1374-1390
Xue, L. Y. et al., Zhonghua Zhong. Liu Za Zhi. 32 (2010): 838-844
Yadav, R. et al., J Neurochem. 133 (2015): 857-869
Yamaguchi, T. et al., Exp. Dermatol. 22 (2013): 840-842
Yamazaki, K., Ultrastruct. Pathol. 31 (2007): 209-219
Yang, C. et al., Tumour.Biol (2015)
Yang, F. et al., Biomed. Rep. 4 (2016a): 681-686
Yang, H. Y. et al., J Proteomics. 75 (2012a): 3639-3653
Yang, J. et al., Curr. Opin. Oncol 25 (2013): 398-406
Yang, L. et al., Carcinogenesis 33 (2012b): 1863-1870
Yang, L. et al., J Biol Chem 291 (2016b): 3905-3917
Ye, Z. et al., Cell Physiol Biochem. 39 (2016): 1568-1580
Yermachenko, A. et al., Gene 590 (2016): 85-89
Yi, K. H. et al., Immunol. Rev 229 (2009): 145-151
Yi, Y. et al., Mol. Cytogenet. 2 (2009): 18
Yong, A. A. et al., Australas. J Dermatol. 54 (2013): 241-250
Yongjun Zhang, M. M. et al., J Cancer Res Ther. 9 (2013): 660-663
Yu, X. J. et al., EBioMedicine 2 (2015a): 583-590
Yu, Y. et al., ACS Appl. Mater. Interfaces. 7 (2015b): 4401-4405
Yu, Y. et al., PLoS. One. 8 (2013): e83943
Yun, C. W. et al., Anticancer Res 36 (2016): 4449-4458
Zaremba, S. et al., Cancer Res. 57 (1997): 4570-4577
Zdrojewicz, Z. et al., Postepy Hig. Med Dosw. (Online.) 68 (2014): 393-403
Zekri, A. R. et al., Asian Pac. J Cancer Prev. 16 (2015): 3543-3549
Zhang, H. et al., Oncotarget. 6 (2015): 17039-17053
Zhang, Q. et al., Endocrinology 143 (2002): 4788-4796
Zhang, S. et al., J Mol. Histol. 45 (2014a): 283-292
Zhang, W. et al., Tumori 100 (2014b): 338-345

Zhang, Y. et al., PLoS.One. 7 (2012): e30188
Zhao, L. H. et al., Genet. Mol. Res 14 (2015): 5417-5426
Zhao, L. J. et al., Chin Med. J (Engl.) 126 (2013): 4260-4264
Zhao, S. et al., Clin Cancer Res 23 (2017): 311-319
Zheng, G. et al., FEBS J 277 (2010): 4506-4518
Zhou, L. et al., Int. J Cancer 135 (2014): 2329-2337
Zhou, P. et al., Eur. J Cancer Prev. 21 (2012): 231-240
Zhou, X. et al., Oncotarget. 7 (2016): 67196-67211

Zhu, X. et al., J Dermatol. 34 (2007): 503-511
Zhu, Y. et al., Mol. Biol Cell 15 (2004): 81-90
Ziari, K. et al., Biologicals 43 (2015): 181-185
Ziegler, A. et al., Cancer Lett. 326 (2012): 1-7
Zimmermann, J. et al., J Dtsch. Dermatol. Ges. 8 (2010): 598-606
Zubor, P. et al., Mol. Biol. Rep. 42 (2015): 977-988

The invention claimed is:

1. A method of treating head and neck squamous cell carcinoma in a HLA-A*02+ patient, wherein said carcinoma comprises cancer cells that overexpress one or more of KRT6A, KRT6B, and KRT6C and present at their surface in complex with an MHC class I molecule a peptide consisting of SEQ ID NO: 1 and/or a peptide consisting of SEQ ID NO: 3 and/or wherein said carcinoma comprises cancer cells that overexpress ALOX12B and present at their surface in complex with an MHC class I molecule a peptide consisting of SEQ ID NO: 14, said method comprising administering to said patient an effective amount of activated antigen-specific CD8+ cytotoxic T cells to kill the cancer cells, wherein said activated antigen-specific CD8+ cytotoxic T cells are produced by contacting in vitro CD8+ cytotoxic T cells with an antigen presenting cell presenting at its surface in complex with an MHC class I molecule a peptide consisting of SEQ ID NO: 1 and/or a peptide consisting of SEQ ID NO: 3 and/or a peptide consisting of SEQ ID NO: 14.

2. The method of claim 1, wherein the cytotoxic T cells produced by contacting CD8+ cytotoxic T cells with said antigen presenting cell are cytotoxic T cells autologous to the patient.

3. The method of claim 1, wherein the cytotoxic T cells produced by contacting CD8+ cytotoxic T cells with said antigen presenting cell are cytotoxic T cells obtained from a healthy donor.

4. The method of claim 1, wherein the cytotoxic T cells produced by contacting CD8+ cytotoxic T cells with said antigen presenting cell are cytotoxic T cells isolated from tumor infiltrating lymphocytes or peripheral blood mononuclear cells.

5. The method of claim 1, wherein the cytotoxic T cells produced by contacting CD8+ cytotoxic T cells with said antigen presenting cell are expanded in vitro before being administered to the patient.

6. The method of claim 5, wherein the cytotoxic T cells are expanded in vitro in the presence of an anti-CD28 antibody and IL-12.

7. The method of claim 1, wherein the effective amount of activated antigen-specific CD8+ cytotoxic T cells to kill the cancer cells are administered in the form of a composition.

8. The method of claim 7, wherein said composition further comprises an adjuvant.

9. The method of claim 8, wherein said adjuvant is selected from agonistic anti-CD40 antibody, imiquimod, resiquimod, GM-CSF, cyclophosphamide, sunitinib, interferon-alpha, interferon-beta, CpG oligonucleotides, poly-(I:C), RNA, sildenafil, particulate formulations with poly (lactide-co-glycolide) (PLG), virosomes, interleukin (IL)-1, IL-2, IL-4, IL-7, IL-12, IL-13, IL-15, IL-21, and IL-23.

10. The method of claim 8, wherein the adjuvant comprises IL-2.

11. The method of claim 8, wherein the adjuvant comprises IL-21.

12. The method of claim 1, wherein the antigen presenting cell is a dendritic cell or a macrophage.

13. The method of claim 1, wherein the antigen presenting cell is infected with a recombinant virus expressing at least one amino acid sequence selected from the group consisting of SEQ ID NO: 1, 3, and 14.

14. The method of claim 1, wherein the antigen presenting cell is an artificial antigen presenting cell (aAPC) comprising an anti-CD28 antibody coupled to its surface.

15. The method of claim 1, wherein the cancer cells overexpress one or more of KRT6A, KRT6B, and KRT6C and present at their surface in complex with an MHC class I molecule a peptide consisting of SEQ ID NO: 1 and wherein said activated antigen-specific CD8+ cytotoxic T cells are produced by contacting in vitro CD8+ cytotoxic T cells with an antigen presenting cell presenting at its surface in complex with an MHC class I molecule a peptide consisting of SEQ ID NO: 1.

16. The method of claim 1, wherein the cancer cells overexpress one or more of KRT6A, KRT6B, and KRT6C and present at their surface in complex with an MHC class I molecule a peptide consisting of SEQ ID NO: 3 and wherein said activated antigen-specific CD8+ cytotoxic T cells are produced by contacting in vitro CD8+ cytotoxic T cells with an antigen presenting cell presenting at its surface in complex with an MHC class I molecule a peptide consisting of SEQ ID NO: 3.

17. The method of claim 1, wherein the cancer cells overexpress ALOX12B and present at their surface in complex with an MHC class I molecule a peptide consisting of SEQ ID NO: 14 and wherein said activated antigen-specific CD8+ cytotoxic T cells are produced by contacting in vitro CD8+ cytotoxic T cells with an antigen presenting cell presenting at its surface in complex with an MHC class I molecule a peptide consisting of SEQ ID NO: 14.

* * * * *

SEQUENCE LISTING

```
<160> NUMBER OF SEQ ID NOS: 158

<210> SEQ ID NO 1
<211> LENGTH: 13
<212> TYPE: PRT
<213> ORGANISM: Homo sapiens

<400> SEQUENCE: 1

Gly Leu Ala Gly Gly Phe Gly Gly Pro Gly Phe Pro Val
1               5                   10

<210> SEQ ID NO 2
<211> LENGTH: 11
<212> TYPE: PRT
<213> ORGANISM: Homo sapiens

<400> SEQUENCE: 2

Pro Val Cys Pro Pro Gly Gly Ile Gln Glu Val
1               5                   10

<210> SEQ ID NO 3
<211> LENGTH: 13
<212> TYPE: PRT
<213> ORGANISM: Homo sapiens

<400> SEQUENCE: 3

Ser Leu Tyr Gly Leu Gly Gly Ser Lys Arg Ile Ser Ile
1               5                   10

<210> SEQ ID NO 4
<211> LENGTH: 10
<212> TYPE: PRT
<213> ORGANISM: Homo sapiens

<400> SEQUENCE: 4

Ile Leu Asp Ile Asn Asp Asn Pro Pro Val
1               5                   10

<210> SEQ ID NO 5
<211> LENGTH: 10
<212> TYPE: PRT
<213> ORGANISM: Homo sapiens

<400> SEQUENCE: 5

Val Cys Pro Pro Gly Gly Ile Gln Glu Val
1               5                   10

<210> SEQ ID NO 6
<211> LENGTH: 10
<212> TYPE: PRT
<213> ORGANISM: Homo sapiens

<400> SEQUENCE: 6

Ala Leu Tyr Asp Ala Glu Leu Ser Gln Met
1               5                   10
```

```
<210> SEQ ID NO 7
<211> LENGTH: 11
<212> TYPE: PRT
<213> ORGANISM: Homo sapiens

<400> SEQUENCE: 7

Ala Leu Glu Glu Ala Asn Ala Asp Leu Glu Val
1               5                   10

<210> SEQ ID NO 8
<211> LENGTH: 11
<212> TYPE: PRT
<213> ORGANISM: Homo sapiens

<400> SEQUENCE: 8

Ala Gln Leu Asn Ile Gly Asn Val Leu Pro Val
1               5                   10

<210> SEQ ID NO 9
<211> LENGTH: 10
<212> TYPE: PRT
<213> ORGANISM: Homo sapiens

<400> SEQUENCE: 9

Ser Thr Ala Ser Ala Ile Thr Pro Ser Val
1               5                   10

<210> SEQ ID NO 10
<211> LENGTH: 10
<212> TYPE: PRT
<213> ORGANISM: Homo sapiens

<400> SEQUENCE: 10

Thr Leu Trp Pro Ala Thr Pro Pro Lys Ala
1               5                   10

<210> SEQ ID NO 11
<211> LENGTH: 9
<212> TYPE: PRT
<213> ORGANISM: Homo sapiens

<400> SEQUENCE: 11

Val Leu Phe Ser Ser Pro Pro Val Ile
1               5

<210> SEQ ID NO 12
<211> LENGTH: 9
<212> TYPE: PRT
<213> ORGANISM: Homo sapiens

<400> SEQUENCE: 12

Thr Leu Thr Asp Glu Ile Asn Phe Leu
1               5

<210> SEQ ID NO 13
<211> LENGTH: 9
<212> TYPE: PRT
<213> ORGANISM: Homo sapiens

<400> SEQUENCE: 13

Ser Leu Val Ser Tyr Leu Asp Lys Val
1               5

<210> SEQ ID NO 14
```

```
<211> LENGTH: 9
<212> TYPE: PRT
<213> ORGANISM: Homo sapiens

<400> SEQUENCE: 14

Arg Ile Met Glu Gly Ile Pro Thr Val
1               5

<210> SEQ ID NO 15
<211> LENGTH: 9
<212> TYPE: PRT
<213> ORGANISM: Homo sapiens

<400> SEQUENCE: 15

Ser Met Leu Asn Asn Ile Ile Asn Leu
1               5

<210> SEQ ID NO 16
<211> LENGTH: 9
<212> TYPE: PRT
<213> ORGANISM: Homo sapiens

<400> SEQUENCE: 16

Ala Leu Lys Asp Ser Val Gln Arg Ala
1               5

<210> SEQ ID NO 17
<211> LENGTH: 9
<212> TYPE: PRT
<213> ORGANISM: Homo sapiens

<400> SEQUENCE: 17

Ser Ile Trp Pro Ala Leu Thr Gln Val
1               5

<210> SEQ ID NO 18
<211> LENGTH: 9
<212> TYPE: PRT
<213> ORGANISM: Homo sapiens

<400> SEQUENCE: 18

Tyr Leu Tyr Pro Asp Leu Ser Arg Leu
1               5

<210> SEQ ID NO 19
<211> LENGTH: 9
<212> TYPE: PRT
<213> ORGANISM: Homo sapiens

<400> SEQUENCE: 19

Ala Leu Ala Lys Leu Leu Pro Leu Leu
1               5

<210> SEQ ID NO 20
<211> LENGTH: 11
<212> TYPE: PRT
<213> ORGANISM: Homo sapiens

<400> SEQUENCE: 20

Tyr Leu Ile Asn Glu Ile Asp Arg Ile Arg Ala
1               5                   10

<210> SEQ ID NO 21
<211> LENGTH: 9
<212> TYPE: PRT
```

```
<213> ORGANISM: Homo sapiens

<400> SEQUENCE: 21

Phe Leu His Glu Pro Phe Ser Ser Val
1               5

<210> SEQ ID NO 22
<211> LENGTH: 10
<212> TYPE: PRT
<213> ORGANISM: Homo sapiens

<400> SEQUENCE: 22

Lys Leu Pro Glu Pro Cys Pro Ser Thr Val
1               5                   10

<210> SEQ ID NO 23
<211> LENGTH: 10
<212> TYPE: PRT
<213> ORGANISM: Homo sapiens

<400> SEQUENCE: 23

Ser Leu Pro Glu Ser Gly Leu Leu Ser Val
1               5                   10

<210> SEQ ID NO 24
<211> LENGTH: 9
<212> TYPE: PRT
<213> ORGANISM: Homo sapiens

<400> SEQUENCE: 24

Leu Leu Ile Ala Ile Asn Pro Gln Val
1               5

<210> SEQ ID NO 25
<211> LENGTH: 11
<212> TYPE: PRT
<213> ORGANISM: Homo sapiens

<400> SEQUENCE: 25

Ser Leu Cys Pro Pro Gly Gly Ile Gln Glu Val
1               5                   10

<210> SEQ ID NO 26
<211> LENGTH: 11
<212> TYPE: PRT
<213> ORGANISM: Homo sapiens

<400> SEQUENCE: 26

Thr Leu Val Asp Glu Asn Gln Ser Trp Tyr Leu
1               5                   10

<210> SEQ ID NO 27
<211> LENGTH: 9
<212> TYPE: PRT
<213> ORGANISM: Homo sapiens

<400> SEQUENCE: 27

Tyr Leu Ala Glu Pro Gln Trp Ala Val
1               5

<210> SEQ ID NO 28
<211> LENGTH: 11
<212> TYPE: PRT
<213> ORGANISM: Homo sapiens
```

```
<400> SEQUENCE: 28

Ala Val Asp Pro Val Ser Gly Ser Leu Tyr Val
1               5                   10

<210> SEQ ID NO 29
<211> LENGTH: 9
<212> TYPE: PRT
<213> ORGANISM: Homo sapiens

<400> SEQUENCE: 29

Arg Leu Leu Pro Asp Leu Asp Glu Val
1               5

<210> SEQ ID NO 30
<211> LENGTH: 10
<212> TYPE: PRT
<213> ORGANISM: Homo sapiens

<400> SEQUENCE: 30

Thr Leu Ala Ser Leu Gly Tyr Ala Val Val
1               5                   10

<210> SEQ ID NO 31
<211> LENGTH: 9
<212> TYPE: PRT
<213> ORGANISM: Homo sapiens

<400> SEQUENCE: 31

His Leu Ala Thr Val Lys Leu Leu Val
1               5

<210> SEQ ID NO 32
<211> LENGTH: 11
<212> TYPE: PRT
<213> ORGANISM: Homo sapiens

<400> SEQUENCE: 32

Ile Gln Asp Ala Glu Gly Ala Ile His Glu Val
1               5                   10

<210> SEQ ID NO 33
<211> LENGTH: 10
<212> TYPE: PRT
<213> ORGANISM: Homo sapiens

<400> SEQUENCE: 33

Ala Ile Tyr Glu Gly Val Gly Trp Asn Val
1               5                   10

<210> SEQ ID NO 34
<211> LENGTH: 9
<212> TYPE: PRT
<213> ORGANISM: Homo sapiens

<400> SEQUENCE: 34

Ala Leu Asp Thr Phe Ser Val Gln Val
1               5

<210> SEQ ID NO 35
<211> LENGTH: 10
<212> TYPE: PRT
<213> ORGANISM: Homo sapiens

<400> SEQUENCE: 35
```

```
Ala Leu Val Gly Asp Val Ile Leu Thr Val
1               5                   10

<210> SEQ ID NO 36
<211> LENGTH: 9
<212> TYPE: PRT
<213> ORGANISM: Homo sapiens

<400> SEQUENCE: 36

Gly Leu Trp Ser Ser Ile Phe Ser Leu
1               5

<210> SEQ ID NO 37
<211> LENGTH: 9
<212> TYPE: PRT
<213> ORGANISM: Homo sapiens

<400> SEQUENCE: 37

Ile Leu Leu Glu Asp Val Phe Gln Leu
1               5

<210> SEQ ID NO 38
<211> LENGTH: 9
<212> TYPE: PRT
<213> ORGANISM: Homo sapiens

<400> SEQUENCE: 38

Lys Leu Leu Pro Gly Val Gln Tyr Val
1               5

<210> SEQ ID NO 39
<211> LENGTH: 11
<212> TYPE: PRT
<213> ORGANISM: Homo sapiens

<400> SEQUENCE: 39

Leu Leu Pro Glu Asp Asp Thr Arg Asp Asn Val
1               5                   10

<210> SEQ ID NO 40
<211> LENGTH: 9
<212> TYPE: PRT
<213> ORGANISM: Homo sapiens

<400> SEQUENCE: 40

Leu Leu Thr Pro Leu Asn Leu Gln Ile
1               5

<210> SEQ ID NO 41
<211> LENGTH: 14
<212> TYPE: PRT
<213> ORGANISM: Homo sapiens

<400> SEQUENCE: 41

Arg Leu Asn Gly Glu Gly Val Gly Gln Val Asn Ile Ser Val
1               5                   10

<210> SEQ ID NO 42
<211> LENGTH: 9
<212> TYPE: PRT
<213> ORGANISM: Homo sapiens

<400> SEQUENCE: 42

Ala Leu Tyr Thr Ser Gly His Leu Leu
1               5
```

```
<210> SEQ ID NO 43
<211> LENGTH: 9
<212> TYPE: PRT
<213> ORGANISM: Homo sapiens

<400> SEQUENCE: 43

Ala Val Leu Gly Gly Lys Leu Tyr Val
1               5

<210> SEQ ID NO 44
<211> LENGTH: 9
<212> TYPE: PRT
<213> ORGANISM: Homo sapiens

<400> SEQUENCE: 44

Gly Leu Gly Asp Asp Ser Phe Pro Ile
1               5

<210> SEQ ID NO 45
<211> LENGTH: 10
<212> TYPE: PRT
<213> ORGANISM: Homo sapiens

<400> SEQUENCE: 45

Gly Leu Ile Glu Trp Leu Glu Asn Thr Val
1               5                   10

<210> SEQ ID NO 46
<211> LENGTH: 10
<212> TYPE: PRT
<213> ORGANISM: Homo sapiens

<400> SEQUENCE: 46

Gly Leu Ile Ser Ser Ile Glu Ala Gln Leu
1               5                   10

<210> SEQ ID NO 47
<211> LENGTH: 10
<212> TYPE: PRT
<213> ORGANISM: Homo sapiens

<400> SEQUENCE: 47

Gln Leu Leu Glu Gly Glu Leu Glu Thr Leu
1               5                   10

<210> SEQ ID NO 48
<211> LENGTH: 9
<212> TYPE: PRT
<213> ORGANISM: Homo sapiens

<400> SEQUENCE: 48

Tyr Leu Leu Asp Tyr Pro Asn Asn Leu
1               5

<210> SEQ ID NO 49
<211> LENGTH: 9
<212> TYPE: PRT
<213> ORGANISM: Homo sapiens

<400> SEQUENCE: 49

Tyr Leu Trp Glu Ala His Thr Asn Ile
1               5
```

-continued

```
<210> SEQ ID NO 50
<211> LENGTH: 9
<212> TYPE: PRT
<213> ORGANISM: Homo sapiens

<400> SEQUENCE: 50

Ala Leu Ser Asn Val Val His Lys Val
1               5

<210> SEQ ID NO 51
<211> LENGTH: 9
<212> TYPE: PRT
<213> ORGANISM: Homo sapiens

<400> SEQUENCE: 51

Phe Leu Ile Pro Ser Ile Ile Phe Ala
1               5

<210> SEQ ID NO 52
<211> LENGTH: 10
<212> TYPE: PRT
<213> ORGANISM: Homo sapiens

<400> SEQUENCE: 52

Leu Leu Phe Thr Gly Leu Val Ser Gly Val
1               5                   10

<210> SEQ ID NO 53
<211> LENGTH: 11
<212> TYPE: PRT
<213> ORGANISM: Homo sapiens

<400> SEQUENCE: 53

Arg Leu Val Glu Val Gly Gly Asp Val Gln Leu
1               5                   10

<210> SEQ ID NO 54
<211> LENGTH: 10
<212> TYPE: PRT
<213> ORGANISM: Homo sapiens

<400> SEQUENCE: 54

Arg Leu Ser Gly Glu Gly Val Gly Pro Val
1               5                   10

<210> SEQ ID NO 55
<211> LENGTH: 9
<212> TYPE: PRT
<213> ORGANISM: Homo sapiens

<400> SEQUENCE: 55

Val Leu Asn Val Gly Val Ala Glu Val
1               5

<210> SEQ ID NO 56
<211> LENGTH: 9
<212> TYPE: PRT
<213> ORGANISM: Homo sapiens

<400> SEQUENCE: 56

Phe Leu Gln Leu Glu Thr Glu Gln Val
1               5

<210> SEQ ID NO 57
<211> LENGTH: 10
```

```
<212> TYPE: PRT
<213> ORGANISM: Homo sapiens

<400> SEQUENCE: 57

Ala Ile Leu Gly Phe Ala Leu Ser Glu Ala
1               5                   10

<210> SEQ ID NO 58
<211> LENGTH: 9
<212> TYPE: PRT
<213> ORGANISM: Homo sapiens

<400> SEQUENCE: 58

Ser Leu Ser Asp Ile Gln Pro Cys Leu
1               5

<210> SEQ ID NO 59
<211> LENGTH: 9
<212> TYPE: PRT
<213> ORGANISM: Homo sapiens

<400> SEQUENCE: 59

Tyr Leu Gln Asn Glu Val Phe Gly Leu
1               5

<210> SEQ ID NO 60
<211> LENGTH: 10
<212> TYPE: PRT
<213> ORGANISM: Homo sapiens

<400> SEQUENCE: 60

Ser Leu Gly Asn Phe Lys Asp Asp Leu Leu
1               5                   10

<210> SEQ ID NO 61
<211> LENGTH: 9
<212> TYPE: PRT
<213> ORGANISM: Homo sapiens

<400> SEQUENCE: 61

Phe Val Ala Gly Tyr Ile Ala Gly Val
1               5

<210> SEQ ID NO 62
<211> LENGTH: 9
<212> TYPE: PRT
<213> ORGANISM: Homo sapiens

<400> SEQUENCE: 62

Ile Leu Ser Ser Ala Cys Tyr Thr Val
1               5

<210> SEQ ID NO 63
<211> LENGTH: 11
<212> TYPE: PRT
<213> ORGANISM: Homo sapiens

<400> SEQUENCE: 63

Ala Leu Met Asp Glu Ile Asn Phe Met Lys Met
1               5                   10

<210> SEQ ID NO 64
<211> LENGTH: 10
<212> TYPE: PRT
<213> ORGANISM: Homo sapiens
```

<400> SEQUENCE: 64

Lys Ile Leu Glu Ser Leu Phe Val Ser Leu
1               5                   10

<210> SEQ ID NO 65
<211> LENGTH: 10
<212> TYPE: PRT
<213> ORGANISM: Homo sapiens

<400> SEQUENCE: 65

Ala Leu Trp Gly Phe Phe Pro Val Leu Leu
1               5                   10

<210> SEQ ID NO 66
<211> LENGTH: 9
<212> TYPE: PRT
<213> ORGANISM: Homo sapiens

<400> SEQUENCE: 66

Thr Leu Leu Ser Glu Ile Ala Glu Leu
1               5

<210> SEQ ID NO 67
<211> LENGTH: 9
<212> TYPE: PRT
<213> ORGANISM: Homo sapiens

<400> SEQUENCE: 67

Ala Gln Leu Asn Leu Ile Trp Gln Leu
1               5

<210> SEQ ID NO 68
<211> LENGTH: 10
<212> TYPE: PRT
<213> ORGANISM: Homo sapiens

<400> SEQUENCE: 68

Lys Ile Leu Glu Met Asp Asp Pro Arg Ala
1               5                   10

<210> SEQ ID NO 69
<211> LENGTH: 9
<212> TYPE: PRT
<213> ORGANISM: Homo sapiens

<400> SEQUENCE: 69

Tyr Val Met Glu Ser Met Thr Tyr Leu
1               5

<210> SEQ ID NO 70
<211> LENGTH: 9
<212> TYPE: PRT
<213> ORGANISM: Homo sapiens

<400> SEQUENCE: 70

Phe Leu Phe Pro Ala Phe Leu Thr Ala
1               5

<210> SEQ ID NO 71
<211> LENGTH: 9
<212> TYPE: PRT
<213> ORGANISM: Homo sapiens

<400> SEQUENCE: 71

Ser Leu Phe Pro Tyr Val Val Leu Ile
1               5

<210> SEQ ID NO 72
<211> LENGTH: 9
<212> TYPE: PRT
<213> ORGANISM: Homo sapiens

<400> SEQUENCE: 72

Ser Leu Asp Gly Asn Pro Leu Ala Val
1               5

<210> SEQ ID NO 73
<211> LENGTH: 10
<212> TYPE: PRT
<213> ORGANISM: Homo sapiens

<400> SEQUENCE: 73

Tyr Ile Asp Pro Tyr Lys Leu Leu Pro Leu
1               5                   10

<210> SEQ ID NO 74
<211> LENGTH: 9
<212> TYPE: PRT
<213> ORGANISM: Homo sapiens

<400> SEQUENCE: 74

Ser Leu Thr Ser Phe Leu Ile Ser Leu
1               5

<210> SEQ ID NO 75
<211> LENGTH: 9
<212> TYPE: PRT
<213> ORGANISM: Homo sapiens

<400> SEQUENCE: 75

Ala Leu Ala Ser Ala Pro Thr Ser Val
1               5

<210> SEQ ID NO 76
<211> LENGTH: 10
<212> TYPE: PRT
<213> ORGANISM: Homo sapiens

<400> SEQUENCE: 76

Ile Leu Phe Asp Glu Val Leu Thr Phe Ala
1               5                   10

<210> SEQ ID NO 77
<211> LENGTH: 9
<212> TYPE: PRT
<213> ORGANISM: Homo sapiens

<400> SEQUENCE: 77

Ser Leu Arg Ala Phe Leu Met Pro Ile
1               5

<210> SEQ ID NO 78
<211> LENGTH: 9
<212> TYPE: PRT
<213> ORGANISM: Homo sapiens

<400> SEQUENCE: 78

Val Leu Tyr Gly Asp Val Glu Glu Leu

-continued

```
<210> SEQ ID NO 79
<211> LENGTH: 11
<212> TYPE: PRT
<213> ORGANISM: Homo sapiens

<400> SEQUENCE: 79

Gly Leu His Gln Asp Phe Pro Ser Val Val Leu
1               5                   10

<210> SEQ ID NO 80
<211> LENGTH: 11
<212> TYPE: PRT
<213> ORGANISM: Homo sapiens

<400> SEQUENCE: 80

Gly Leu Tyr Gly Ile Lys Asp Asp Val Phe Leu
1               5                   10

<210> SEQ ID NO 81
<211> LENGTH: 11
<212> TYPE: PRT
<213> ORGANISM: Homo sapiens

<400> SEQUENCE: 81

Val Leu Ala Glu Asn Pro Asp Ile Phe Ala Val
1               5                   10

<210> SEQ ID NO 82
<211> LENGTH: 10
<212> TYPE: PRT
<213> ORGANISM: Homo sapiens

<400> SEQUENCE: 82

Val Leu Asp Ile Asn Asp Asn Pro Pro Val
1               5                   10

<210> SEQ ID NO 83
<211> LENGTH: 9
<212> TYPE: PRT
<213> ORGANISM: Homo sapiens

<400> SEQUENCE: 83

Gln Leu Leu Gln Tyr Val Tyr Asn Leu
1               5

<210> SEQ ID NO 84
<211> LENGTH: 10
<212> TYPE: PRT
<213> ORGANISM: Homo sapiens

<400> SEQUENCE: 84

Ala Leu Met Ala Gly Cys Ile Gln Glu Ala
1               5                   10

<210> SEQ ID NO 85
<211> LENGTH: 9
<212> TYPE: PRT
<213> ORGANISM: Homo sapiens

<400> SEQUENCE: 85

Gln Leu Ile Glu Lys Ile Thr Gln Val
1               5
```

```
<210> SEQ ID NO 86
<211> LENGTH: 9
<212> TYPE: PRT
<213> ORGANISM: Homo sapiens

<400> SEQUENCE: 86

Ser Leu Gln Glu Arg Gln Val Phe Leu
1               5

<210> SEQ ID NO 87
<211> LENGTH: 9
<212> TYPE: PRT
<213> ORGANISM: Homo sapiens

<400> SEQUENCE: 87

Ala Leu Pro Glu Pro Ser Pro Ala Ala
1               5

<210> SEQ ID NO 88
<211> LENGTH: 9
<212> TYPE: PRT
<213> ORGANISM: Homo sapiens

<400> SEQUENCE: 88

Leu Met Ala Pro Ala Pro Ser Thr Val
1               5

<210> SEQ ID NO 89
<211> LENGTH: 9
<212> TYPE: PRT
<213> ORGANISM: Homo sapiens

<400> SEQUENCE: 89

Val Leu Asp Glu Gly Leu Thr Ser Val
1               5

<210> SEQ ID NO 90
<211> LENGTH: 10
<212> TYPE: PRT
<213> ORGANISM: Homo sapiens

<400> SEQUENCE: 90

Thr Leu Asn Asp Gly Val Val Val Gln Val
1               5                   10

<210> SEQ ID NO 91
<211> LENGTH: 11
<212> TYPE: PRT
<213> ORGANISM: Homo sapiens

<400> SEQUENCE: 91

Met Leu Phe Glu Asn Met Gly Ala Tyr Thr Val
1               5                   10

<210> SEQ ID NO 92
<211> LENGTH: 9
<212> TYPE: PRT
<213> ORGANISM: Homo sapiens

<400> SEQUENCE: 92

Ile Leu Leu Asp Val Lys Thr Arg Leu
1               5

<210> SEQ ID NO 93
```

```
<211> LENGTH: 9
<212> TYPE: PRT
<213> ORGANISM: Homo sapiens

<400> SEQUENCE: 93

Ala Leu Ser Asn Val Ile His Lys Val
1               5

<210> SEQ ID NO 94
<211> LENGTH: 10
<212> TYPE: PRT
<213> ORGANISM: Homo sapiens

<400> SEQUENCE: 94

Ser Ile Phe Glu Gly Leu Leu Ser Gly Val
1               5                   10

<210> SEQ ID NO 95
<211> LENGTH: 10
<212> TYPE: PRT
<213> ORGANISM: Homo sapiens

<400> SEQUENCE: 95

Ser Leu Asp Glu Asn Ser Asp Gln Gln Val
1               5                   10

<210> SEQ ID NO 96
<211> LENGTH: 13
<212> TYPE: PRT
<213> ORGANISM: Homo sapiens

<400> SEQUENCE: 96

Phe Gln Leu Asp Pro Ser Ser Gly Val Leu Val Thr Val
1               5                   10

<210> SEQ ID NO 97
<211> LENGTH: 9
<212> TYPE: PRT
<213> ORGANISM: Homo sapiens

<400> SEQUENCE: 97

Leu Ile Leu Glu Ser Ile Pro Val Val
1               5

<210> SEQ ID NO 98
<211> LENGTH: 9
<212> TYPE: PRT
<213> ORGANISM: Homo sapiens

<400> SEQUENCE: 98

Ser Leu Tyr Lys Gly Leu Leu Ser Val
1               5

<210> SEQ ID NO 99
<211> LENGTH: 9
<212> TYPE: PRT
<213> ORGANISM: Homo sapiens

<400> SEQUENCE: 99

Thr Ala Ser Ala Ile Thr Pro Ser Val
1               5

<210> SEQ ID NO 100
<211> LENGTH: 10
<212> TYPE: PRT
```

```
<213> ORGANISM: Homo sapiens

<400> SEQUENCE: 100

Val Leu Val Ser Asp Gly Val His Ser Val
1               5                   10

<210> SEQ ID NO 101
<211> LENGTH: 11
<212> TYPE: PRT
<213> ORGANISM: Homo sapiens

<400> SEQUENCE: 101

Gly Leu Leu Pro Ser Ala Glu Ser Ile Lys Leu
1               5                   10

<210> SEQ ID NO 102
<211> LENGTH: 11
<212> TYPE: PRT
<213> ORGANISM: Homo sapiens

<400> SEQUENCE: 102

Thr Leu Ala Glu Leu Gln Pro Pro Val Gln Leu
1               5                   10

<210> SEQ ID NO 103
<211> LENGTH: 9
<212> TYPE: PRT
<213> ORGANISM: Homo sapiens

<400> SEQUENCE: 103

Val Leu Ala Glu Gly Gly Glu Gly Val
1               5

<210> SEQ ID NO 104
<211> LENGTH: 9
<212> TYPE: PRT
<213> ORGANISM: Homo sapiens

<400> SEQUENCE: 104

Ser Leu Ser Pro Val Ile Leu Gly Val
1               5

<210> SEQ ID NO 105
<211> LENGTH: 9
<212> TYPE: PRT
<213> ORGANISM: Homo sapiens

<400> SEQUENCE: 105

Ser Thr Tyr Gly Gly Gly Leu Ser Val
1               5

<210> SEQ ID NO 106
<211> LENGTH: 9
<212> TYPE: PRT
<213> ORGANISM: Homo sapiens

<400> SEQUENCE: 106

Val Leu Val Asp Gln Ser Trp Val Leu
1               5

<210> SEQ ID NO 107
<211> LENGTH: 9
<212> TYPE: PRT
<213> ORGANISM: Homo sapiens
```

```
<400> SEQUENCE: 107

Tyr Leu Glu Glu Asp Val Tyr Gln Leu
1               5

<210> SEQ ID NO 108
<211> LENGTH: 13
<212> TYPE: PRT
<213> ORGANISM: Homo sapiens

<400> SEQUENCE: 108

Ser Leu Tyr Asn Leu Gly Gly Ser Lys Arg Ile Ser Ile
1               5                   10

<210> SEQ ID NO 109
<211> LENGTH: 9
<212> TYPE: PRT
<213> ORGANISM: Homo sapiens

<400> SEQUENCE: 109

Lys Ile Gln Glu Ile Leu Thr Gln Val
1               5

<210> SEQ ID NO 110
<211> LENGTH: 9
<212> TYPE: PRT
<213> ORGANISM: Homo sapiens

<400> SEQUENCE: 110

Leu Leu Pro Pro Pro Pro Pro Pro Ala
1               5

<210> SEQ ID NO 111
<211> LENGTH: 11
<212> TYPE: PRT
<213> ORGANISM: Homo sapiens

<400> SEQUENCE: 111

Ser Leu Ala Pro Gly Asp Val Val Arg Gln Val
1               5                   10

<210> SEQ ID NO 112
<211> LENGTH: 13
<212> TYPE: PRT
<213> ORGANISM: Homo sapiens

<400> SEQUENCE: 112

Ala Leu Leu Asp Gly Gly Ser Glu Ala Tyr Trp Arg Val
1               5                   10

<210> SEQ ID NO 113
<211> LENGTH: 9
<212> TYPE: PRT
<213> ORGANISM: Homo sapiens

<400> SEQUENCE: 113

Asn Leu Met Ala Ser Gln Pro Gln Leu
1               5

<210> SEQ ID NO 114
<211> LENGTH: 10
<212> TYPE: PRT
<213> ORGANISM: Homo sapiens

<400> SEQUENCE: 114
```

```
Val Leu Val Pro Tyr Glu Pro Pro Gln Val
1               5                   10
```

<210> SEQ ID NO 115
<211> LENGTH: 11
<212> TYPE: PRT
<213> ORGANISM: Homo sapiens

<400> SEQUENCE: 115

```
Val Thr Ala Ala Tyr Met Asp Thr Val Ser Leu
1               5                   10
```

<210> SEQ ID NO 116
<211> LENGTH: 9
<212> TYPE: PRT
<213> ORGANISM: Homo sapiens

<400> SEQUENCE: 116

```
Ser Leu Trp Pro Ser Pro Glu Gln Leu
1               5
```

<210> SEQ ID NO 117
<211> LENGTH: 9
<212> TYPE: PRT
<213> ORGANISM: Homo sapiens

<400> SEQUENCE: 117

```
Gly Leu Ala Phe Ser Leu Tyr Gln Ala
1               5
```

<210> SEQ ID NO 118
<211> LENGTH: 11
<212> TYPE: PRT
<213> ORGANISM: Homo sapiens

<400> SEQUENCE: 118

```
Thr Leu Leu Gln Glu Gln Gly Thr Lys Thr Val
1               5                   10
```

<210> SEQ ID NO 119
<211> LENGTH: 10
<212> TYPE: PRT
<213> ORGANISM: Homo sapiens

<400> SEQUENCE: 119

```
Gly Leu Leu Asp Pro Ser Val Phe His Val
1               5                   10
```

<210> SEQ ID NO 120
<211> LENGTH: 9
<212> TYPE: PRT
<213> ORGANISM: Homo sapiens

<400> SEQUENCE: 120

```
Tyr Leu Val Ala Lys Leu Val Glu Val
1               5
```

<210> SEQ ID NO 121
<211> LENGTH: 9
<212> TYPE: PRT
<213> ORGANISM: Homo sapiens

<400> SEQUENCE: 121

```
Ser Leu Tyr Gly Tyr Leu Arg Gly Ala
1               5
```

<210> SEQ ID NO 122
<211> LENGTH: 11
<212> TYPE: PRT
<213> ORGANISM: Homo sapiens

<400> SEQUENCE: 122

Ile Leu Asp Glu Ala Gly Val Lys Tyr Phe Leu
1               5                   10

<210> SEQ ID NO 123
<211> LENGTH: 9
<212> TYPE: PRT
<213> ORGANISM: Homo sapiens

<400> SEQUENCE: 123

Leu Leu Ser Gly Asp Leu Ile Phe Leu
1               5

<210> SEQ ID NO 124
<211> LENGTH: 9
<212> TYPE: PRT
<213> ORGANISM: Homo sapiens

<400> SEQUENCE: 124

Tyr Met Leu Asp Ile Phe His Glu Val
1               5

<210> SEQ ID NO 125
<211> LENGTH: 9
<212> TYPE: PRT
<213> ORGANISM: Homo sapiens

<400> SEQUENCE: 125

Ala Leu Asn Pro Glu Ile Val Ser Val
1               5

<210> SEQ ID NO 126
<211> LENGTH: 9
<212> TYPE: PRT
<213> ORGANISM: Homo sapiens

<400> SEQUENCE: 126

Ile Leu Val Asp Trp Leu Val Glu Val
1               5

<210> SEQ ID NO 127
<211> LENGTH: 9
<212> TYPE: PRT
<213> ORGANISM: Homo sapiens

<400> SEQUENCE: 127

Ser Leu Phe Gly Lys Lys Tyr Ile Leu
1               5

<210> SEQ ID NO 128
<211> LENGTH: 9
<212> TYPE: PRT
<213> ORGANISM: Homo sapiens

<400> SEQUENCE: 128

Thr Leu His Arg Glu Thr Phe Tyr Leu
1               5

```
<210> SEQ ID NO 129
<211> LENGTH: 11
<212> TYPE: PRT
<213> ORGANISM: Homo sapiens

<400> SEQUENCE: 129

Ser Leu Ser Gly Glu Ile Ile Leu His Ser Val
1               5                   10

<210> SEQ ID NO 130
<211> LENGTH: 10
<212> TYPE: PRT
<213> ORGANISM: Homo sapiens

<400> SEQUENCE: 130

Thr Leu Asp Gly Ala Ala Val Asn Gln Val
1               5                   10

<210> SEQ ID NO 131
<211> LENGTH: 9
<212> TYPE: PRT
<213> ORGANISM: Homo sapiens

<400> SEQUENCE: 131

Leu Gln Leu Asp Lys Glu Phe Gln Leu
1               5

<210> SEQ ID NO 132
<211> LENGTH: 10
<212> TYPE: PRT
<213> ORGANISM: Homo sapiens

<400> SEQUENCE: 132

Thr Leu Tyr Pro Gly Arg Phe Asp Tyr Val
1               5                   10

<210> SEQ ID NO 133
<211> LENGTH: 9
<212> TYPE: PRT
<213> ORGANISM: Homo sapiens

<400> SEQUENCE: 133

Leu Leu Leu Pro Leu Gln Ile Leu Leu
1               5

<210> SEQ ID NO 134
<211> LENGTH: 9
<212> TYPE: PRT
<213> ORGANISM: Homo sapiens

<400> SEQUENCE: 134

Ile Leu Ile Gly Glu Thr Ile Lys Ile
1               5

<210> SEQ ID NO 135
<211> LENGTH: 9
<212> TYPE: PRT
<213> ORGANISM: Homo sapiens

<400> SEQUENCE: 135

Gly Leu Phe Ser Gln His Phe Asn Leu
1               5

<210> SEQ ID NO 136
<211> LENGTH: 11
```

```
<212> TYPE: PRT
<213> ORGANISM: Homo sapiens

<400> SEQUENCE: 136

Ser Leu Met Glu Pro Pro Ala Val Leu Leu Leu
1               5                   10

<210> SEQ ID NO 137
<211> LENGTH: 10
<212> TYPE: PRT
<213> ORGANISM: Homo sapiens

<400> SEQUENCE: 137

Gly Leu Ala Pro Phe Leu Leu Asn Ala Val
1               5                   10

<210> SEQ ID NO 138
<211> LENGTH: 10
<212> TYPE: PRT
<213> ORGANISM: Homo sapiens

<400> SEQUENCE: 138

Ala Leu Leu Thr Gly Ile Ile Ser Lys Ala
1               5                   10

<210> SEQ ID NO 139
<211> LENGTH: 9
<212> TYPE: PRT
<213> ORGANISM: Homo sapiens

<400> SEQUENCE: 139

Gln Leu Gly Pro Val Pro Val Thr Ile
1               5

<210> SEQ ID NO 140
<211> LENGTH: 9
<212> TYPE: PRT
<213> ORGANISM: Homo sapiens

<400> SEQUENCE: 140

Tyr Leu Phe Glu Asn Ile Ser Gln Leu
1               5

<210> SEQ ID NO 141
<211> LENGTH: 10
<212> TYPE: PRT
<213> ORGANISM: Homo sapiens

<400> SEQUENCE: 141

Phe Leu Asn Pro Asp Glu Val His Ala Ile
1               5                   10

<210> SEQ ID NO 142
<211> LENGTH: 10
<212> TYPE: PRT
<213> ORGANISM: Homo sapiens

<400> SEQUENCE: 142

Ser Leu Val Ser Glu Gln Leu Glu Pro Ala
1               5                   10

<210> SEQ ID NO 143
<211> LENGTH: 9
<212> TYPE: PRT
<213> ORGANISM: Homo sapiens
```

<400> SEQUENCE: 143

Tyr Val Tyr Gln Asn Asn Ile Tyr Leu
1               5

<210> SEQ ID NO 144
<211> LENGTH: 9
<212> TYPE: PRT
<213> ORGANISM: Homo sapiens

<400> SEQUENCE: 144

Lys Ile Ser Thr Ile Thr Pro Gln Ile
1               5

<210> SEQ ID NO 145
<211> LENGTH: 9
<212> TYPE: PRT
<213> ORGANISM: Homo sapiens

<400> SEQUENCE: 145

Leu Leu Tyr Gly Lys Tyr Val Ser Val
1               5

<210> SEQ ID NO 146
<211> LENGTH: 9
<212> TYPE: PRT
<213> ORGANISM: Homo sapiens

<400> SEQUENCE: 146

Gly Leu Leu Glu Glu Leu Val Thr Val
1               5

<210> SEQ ID NO 147
<211> LENGTH: 10
<212> TYPE: PRT
<213> ORGANISM: Homo sapiens

<400> SEQUENCE: 147

Ile Leu Met Asp Pro Ser Pro Glu Tyr Ala
1               5                   10

<210> SEQ ID NO 148
<211> LENGTH: 10
<212> TYPE: PRT
<213> ORGANISM: Homo sapiens

<400> SEQUENCE: 148

Leu Leu Phe Asp Ala Pro Asp Leu Arg Leu
1               5                   10

<210> SEQ ID NO 149
<211> LENGTH: 10
<212> TYPE: PRT
<213> ORGANISM: Homo sapiens

<400> SEQUENCE: 149

Val Leu Leu Asn Ile Asn Gly Ile Asp Leu
1               5                   10

<210> SEQ ID NO 150
<211> LENGTH: 11
<212> TYPE: PRT
<213> ORGANISM: Homo sapiens

<400> SEQUENCE: 150

```
Ile Leu Ala Glu Glu Pro Ile Tyr Ile Arg Val
1               5                   10

<210> SEQ ID NO 151
<211> LENGTH: 9
<212> TYPE: PRT
<213> ORGANISM: Homo sapiens

<400> SEQUENCE: 151

Gln Leu Cys Asp Leu Asn Ala Glu Leu
1               5

<210> SEQ ID NO 152
<211> LENGTH: 9
<212> TYPE: PRT
<213> ORGANISM: Homo sapiens

<400> SEQUENCE: 152

Ser Leu Trp Gln Asp Ile Pro Asp Val
1               5

<210> SEQ ID NO 153
<211> LENGTH: 9
<212> TYPE: PRT
<213> ORGANISM: Homo sapiens

<400> SEQUENCE: 153

Val Leu Phe Leu Gly Lys Leu Leu Val
1               5

<210> SEQ ID NO 154
<211> LENGTH: 10
<212> TYPE: PRT
<213> ORGANISM: Homo sapiens

<400> SEQUENCE: 154

Lys Met Trp Glu Glu Leu Pro Glu Val Val
1               5                   10

<210> SEQ ID NO 155
<211> LENGTH: 10
<212> TYPE: PRT
<213> ORGANISM: Homo sapiens

<400> SEQUENCE: 155

Gly Leu Leu Asp Asn Pro Glu Leu Arg Val
1               5                   10

<210> SEQ ID NO 156
<211> LENGTH: 13
<212> TYPE: PRT
<213> ORGANISM: Homo sapiens

<400> SEQUENCE: 156

Ala Leu Ile Asn Asp Ile Leu Gly Glu Leu Val Lys Leu
1               5                   10

<210> SEQ ID NO 157
<211> LENGTH: 10
<212> TYPE: PRT
<213> ORGANISM: Homo sapiens

<400> SEQUENCE: 157

Glu Leu Ala Gly Ile Gly Ile Leu Thr Val
```

```
-continued
1               5               10

<210> SEQ ID NO 158
<211> LENGTH: 9
<212> TYPE: PRT
<213> ORGANISM: Homo sapiens

<400> SEQUENCE: 158

Tyr Leu Leu Pro Ala Ile Val His Ile
1               5
```